US011506671B2

(12) United States Patent
Ohta et al.

(10) Patent No.: US 11,506,671 B2
(45) Date of Patent: Nov. 22, 2022

(54) METHOD AND SYSTEM FOR ANALYZING N-LINKED SUGAR CHAINS OF GLYCOPROTEIN

(71) Applicant: Public University Corporation Yokohama City University, Yokohama (JP)

(72) Inventors: Yuki Ohta, Yokohama (JP); Nana Kawasaki, Yokohama (JP); Daisuke Takakura, Yokohama (JP)

(73) Assignee: PUBLIC UNIVERSITY CORPORATION YOKOHAMA CITY UNIVERSITY, Yokohama (JP)

( * ) Notice: Subject to any disclaimer, the term of this patent is extended or adjusted under 35 U.S.C. 154(b) by 802 days.

(21) Appl. No.: 16/326,634

(22) PCT Filed: Aug. 18, 2017

(86) PCT No.: PCT/JP2017/029658
§ 371 (c)(1),
(2) Date: Jul. 11, 2019

(87) PCT Pub. No.: WO2018/034346
PCT Pub. Date: Feb. 22, 2018

(65) Prior Publication Data
US 2020/0378982 A1 Dec. 3, 2020

(30) Foreign Application Priority Data
Aug. 19, 2016 (JP) .............................. JP2016-161118

(51) Int. Cl.
*G01N 33/68* (2006.01)
*C07K 16/00* (2006.01)
(Continued)

(52) U.S. Cl.
CPC ......... *G01N 33/6848* (2013.01); *C07K 16/00* (2013.01); *C12Q 1/44* (2013.01);
(Continued)

(58) Field of Classification Search
None
See application file for complete search history.

(56) References Cited

U.S. PATENT DOCUMENTS

2008/0048110 A1    2/2008  Deguchi et al.

FOREIGN PATENT DOCUMENTS

EP    3 088 531 A1    11/2016
JP    2008-309501 A    12/2008
(Continued)

OTHER PUBLICATIONS

Cao et al., "N-Glycosylation Site Analysis of Proteins from *Saccharomyces cerivisiae* by Using Hydrophilic Interaction Liquid Chromatography-Based Enrichment, Parallel Deglycosylation, and Mass Spectometry," J. Proteome Res. (Feb. 1, 2014), pp. A-I (XP055104562).
Extended European Search Report dated May 19, 2020, in European Patent Application No. 17841567.5.
Hagglund et al., "A New Strategy for Identification of N-Glycosylated Proteins and Unambiguous Assignment of their Glycosylation Sites Using HILIC Enrichment and Partial Deglycosylation," J. Proteome Res. (2004), vol. 3, pp. 556-566.
(Continued)

*Primary Examiner* — Xiaoyun R Xu
(74) *Attorney, Agent, or Firm* — Birch, Stewart, Kolasch & Birch, LLP

(57) ABSTRACT

Disclosed is a novel means for accurate qualitative and quantitative analyses for each N-glycosylation site. The method of analyzing N-linked sugar chain(s) of glycoprotein according to the present invention comprises: treating a part of a glycopeptide-containing sample to be analyzed with endo-β-N-acetylglucosaminidases to cleave off sugar chains while leaving one GlcNAc of the chitobiose core on the Asn at the N-glycosylation site; subjecting the obtained sugar chain-cleaved sample to preliminary liquid chromatography/mass spectrometry; predicting the retention time of the
(Continued)

glycopeptide of interest and the mass-to-charge ratio (m/z) of the precursor ion in main analysis based on the results of the preliminary liquid chromatography/mass spectrometry; and carrying out the main analysis. By this method, the binding sites and structures of N-linked sugar chains in a glycoprotein can be analyzed. By using the sugar chain-cleaved sample as an internal standard in the main analysis, quantitative analysis of sugar chains at each glycosylation site also becomes possible.

10 Claims, 46 Drawing Sheets

Specification includes a Sequence Listing.

(51) Int. Cl.
  *C12Q 1/44*   (2006.01)
  *G01N 30/72*  (2006.01)
  *G01N 30/86*  (2006.01)
  *H01J 49/00*  (2006.01)
  *G01N 30/02*  (2006.01)
(52) U.S. Cl.
  CPC ..... *G01N 30/7233* (2013.01); *G01N 30/8696* (2013.01); *H01J 49/004* (2013.01); *H01J 49/0031* (2013.01); *C07K 2317/41* (2013.01); *G01N 2030/027* (2013.01); *G01N 2400/00* (2013.01); *G01N 2440/38* (2013.01)

(56) References Cited

FOREIGN PATENT DOCUMENTS

| | | | |
|---|---|---|---|
| JP | 2009-145169 A | 7/2009 |
| JP | 2010-256101 A | 11/2010 |
| JP | 2015-142555 A | 8/2015 |
| JP | 2015/145840 A | 8/2015 |
| WO | WO 2009/080278 A1 | 7/2009 |
| WO | WO 2015/152135 A | 10/2015 |

OTHER PUBLICATIONS

Kurogochi et al., "Relative Quantitation of Glycopeptides Based on Stable Isotope Labeling Using MALDI-TOF MS," Molecules (2014), vol. 19, pp. 9944-9961.

Segu et al., "Assigning N-Glycosylation Sites of Glycoproteins using LC/MSMS in Conjuction with Endo-M/Exoglycosidase Mixture," J. Proteome Res. (2010), vol. 9, pp. 3598-3607.

Thaysen-Andersen et al., "Maturing Glycoproteomics Technologies Provide Unique Strutural Insights into the N-glycoproteome and its Regulation in Health and Disease," Molecular and Cellular Proteomics (2016), vol. 15, pp. 1773-1790.

International Search Report dated Nov. 14, 2017, in PCT/JP2017/029658.

Kaji et al., "Lectin affinity capture, isotope-coded tagging and mass spectrometry to identify N-linked glycoproteins," Nature Biotechnology (Jun. 2003), vol. 21, No. 6, pp. 667-672.

Maehara et al., "Quantitation method for glycoforms of monoclonal antibodies using a novel internal standard," Dai 65 Kai Annual Conference on Mass Spectometry (2017) Koen Yoshishu,(May 1, 2017), p. 160, 2P-47 (with abstract).

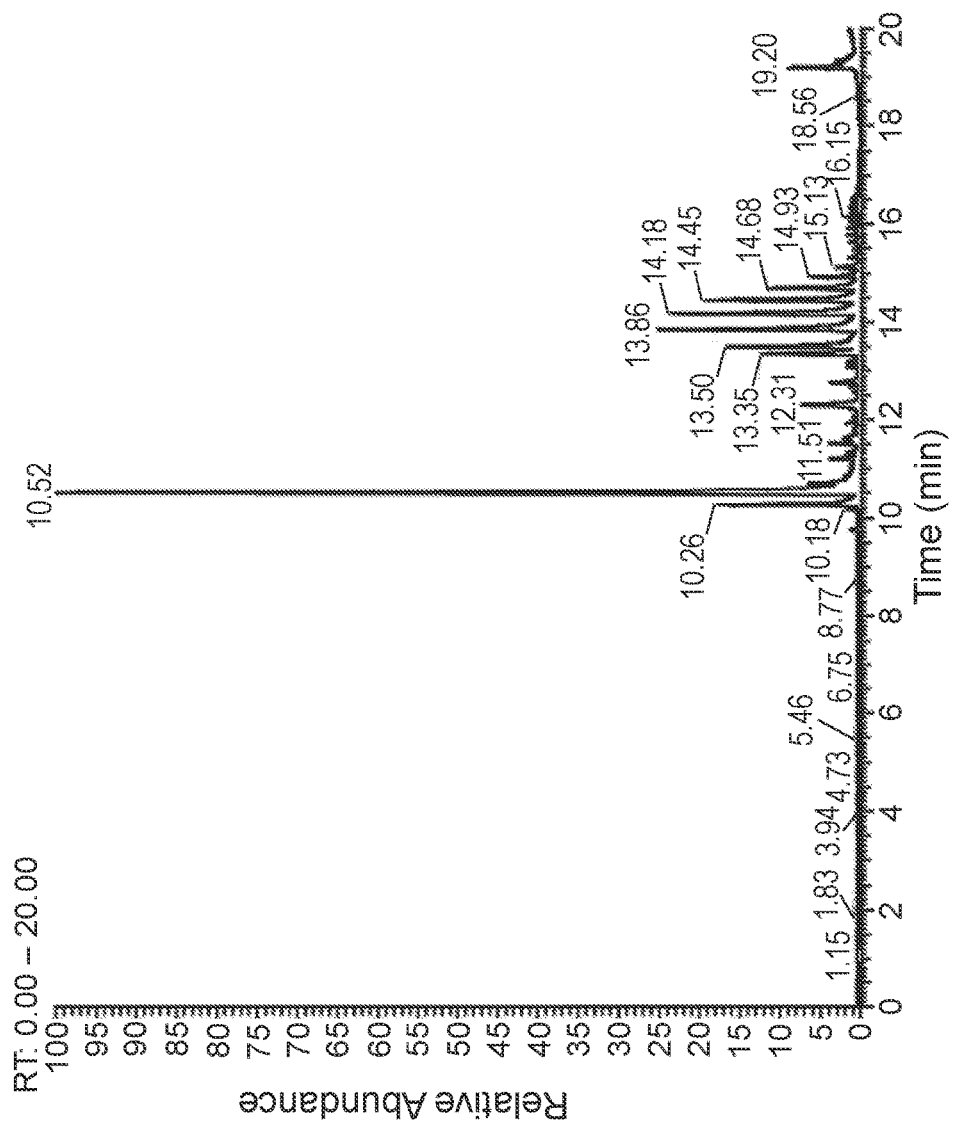
Fig. 9A A Base peak chromatogram of the peptides whose sugar chains were cleaved off while leaving GlcNAc thereon, prepared from IgG1 antibody A  Relative intensity of sugar chains of a certain mAb relative to the internal standard B  Relative intensity of sugar chains of a human myeloma-derived IgG1 relative to the internal standard

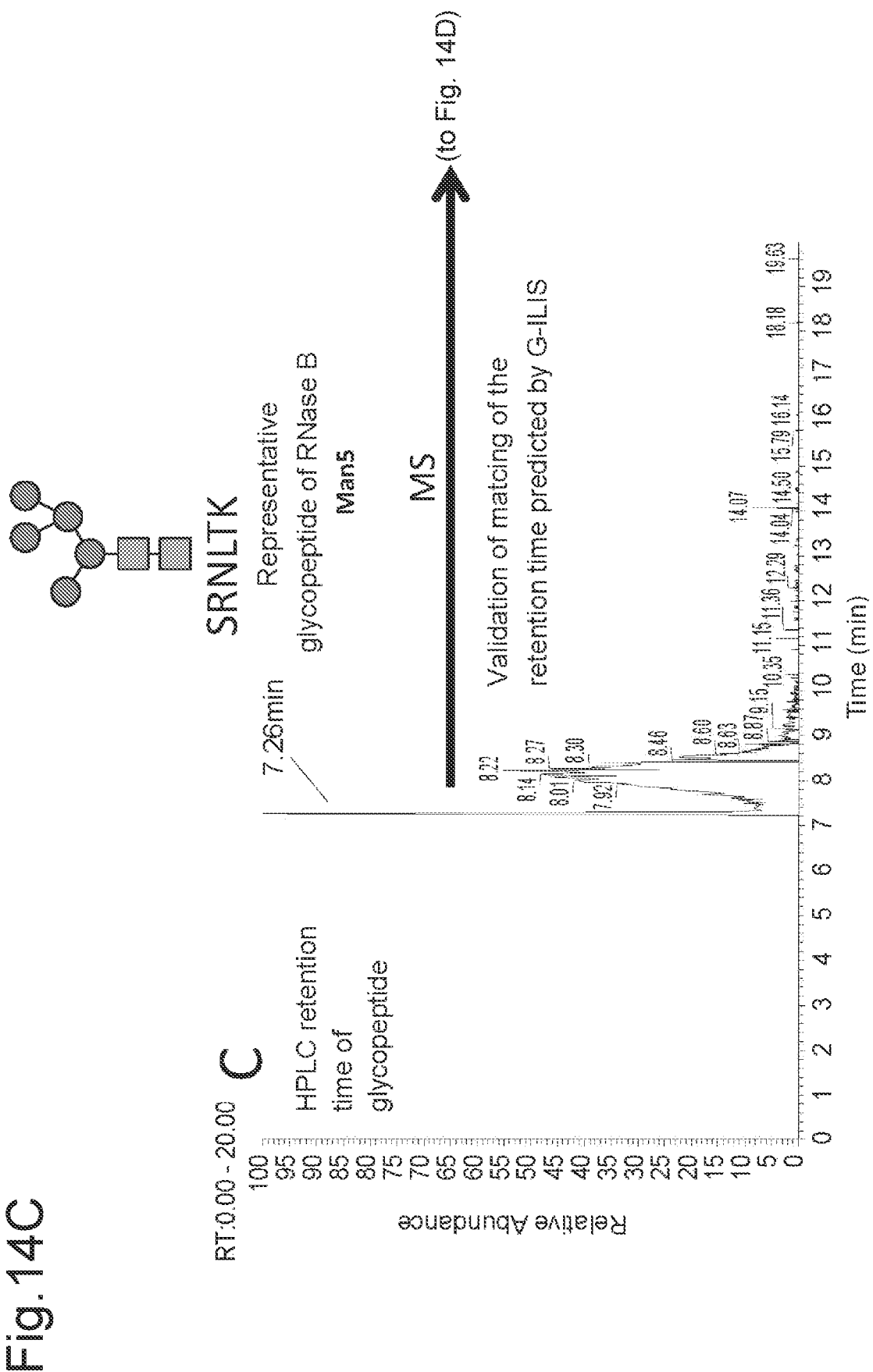

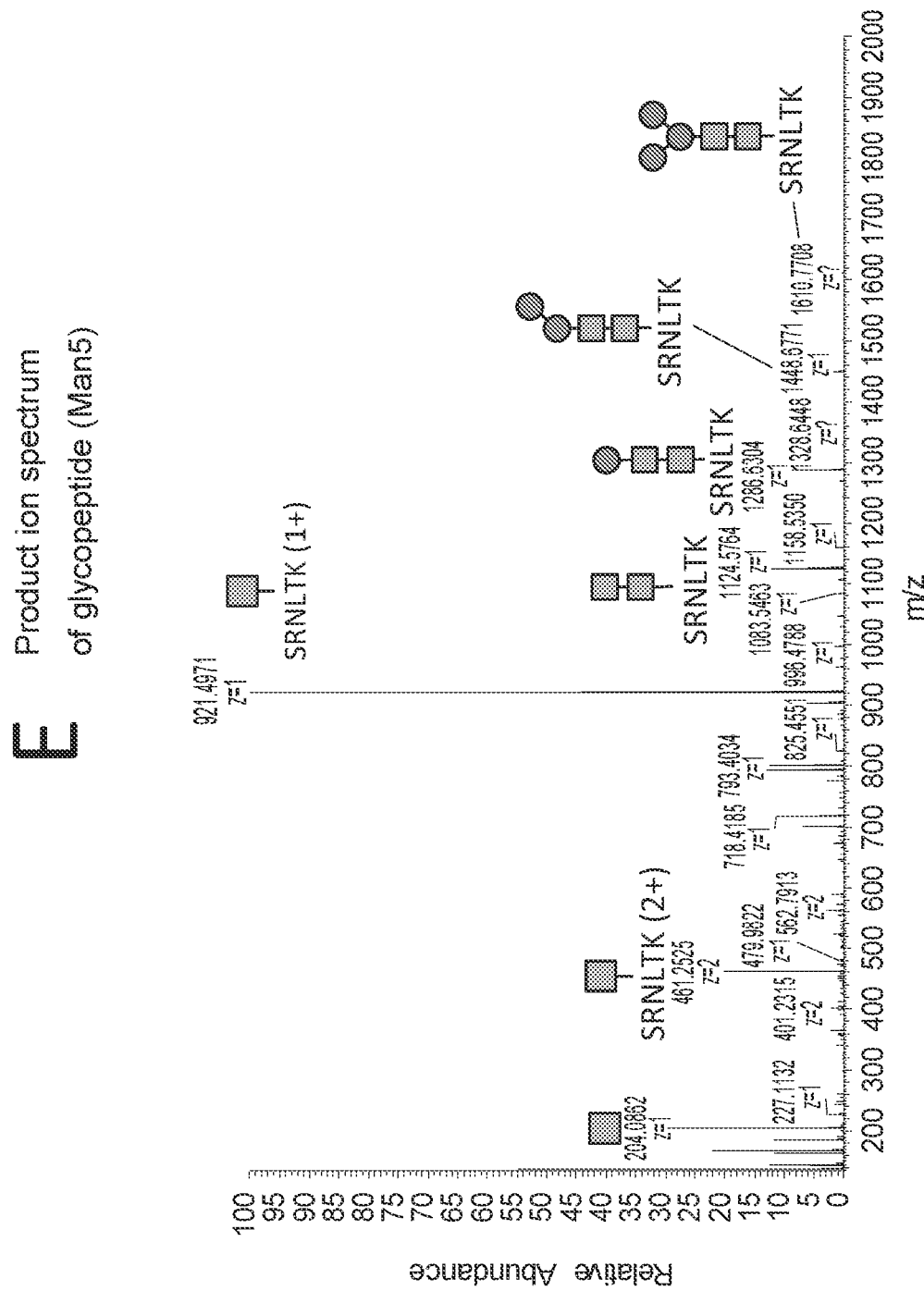

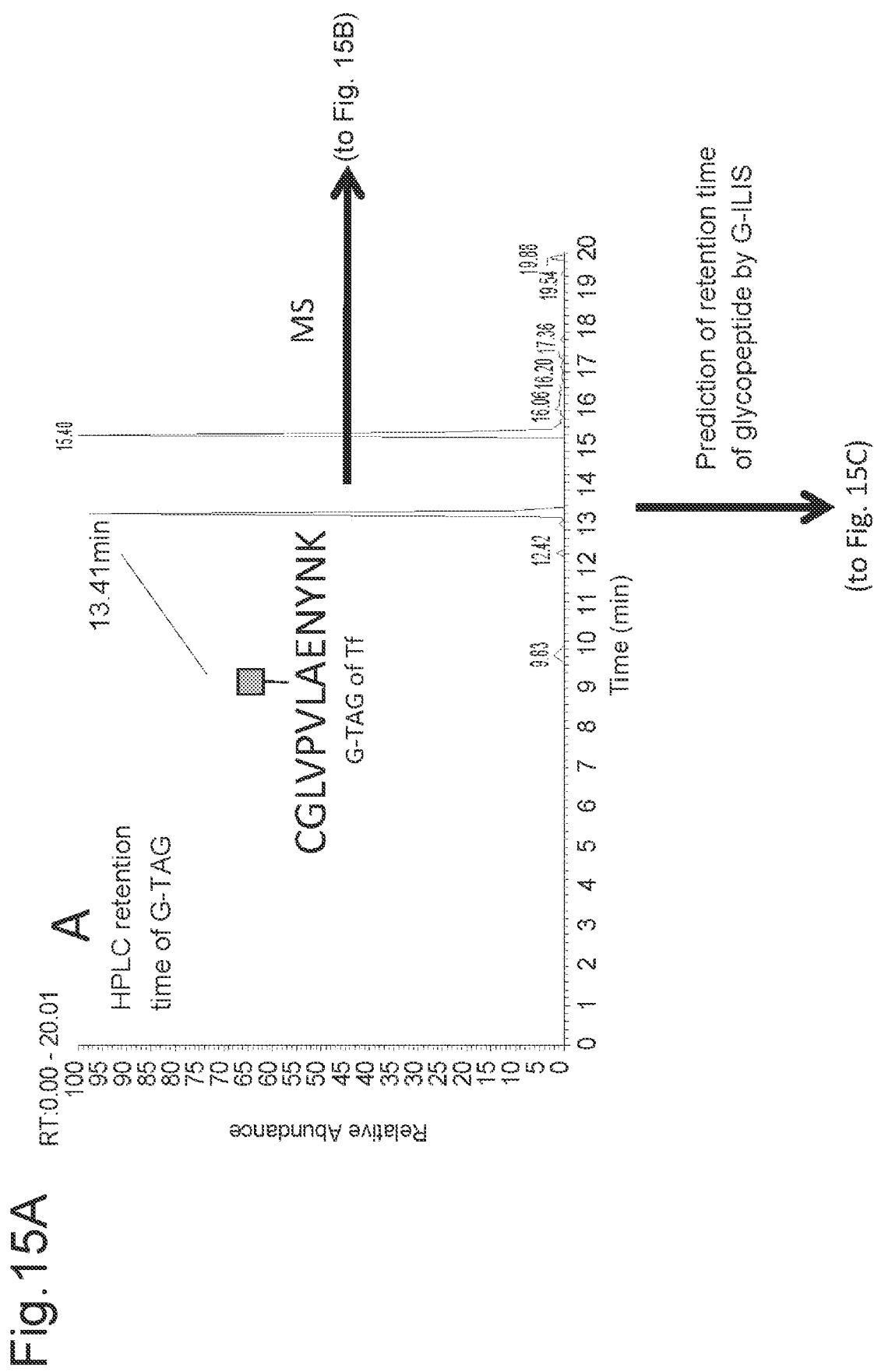

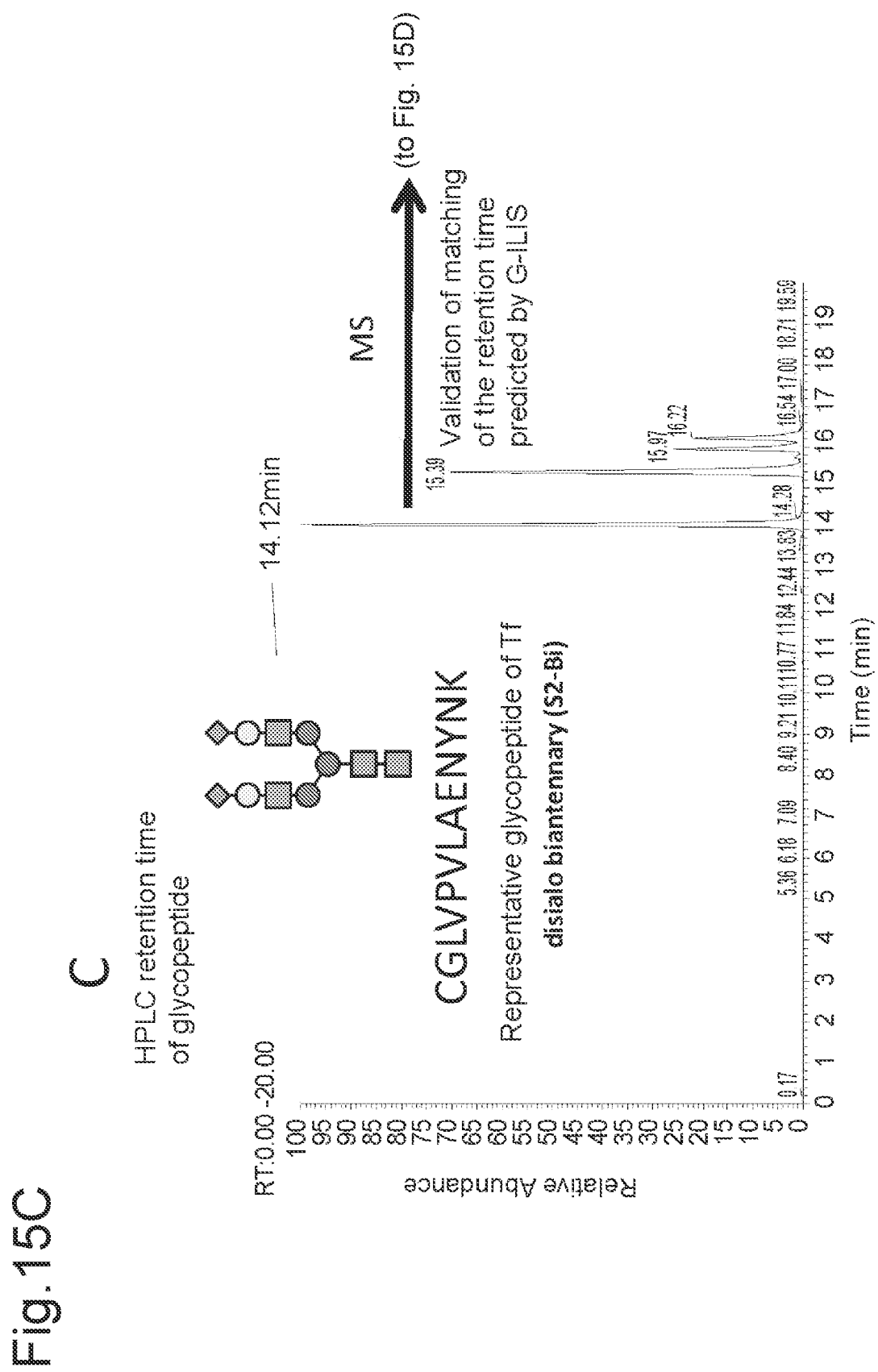

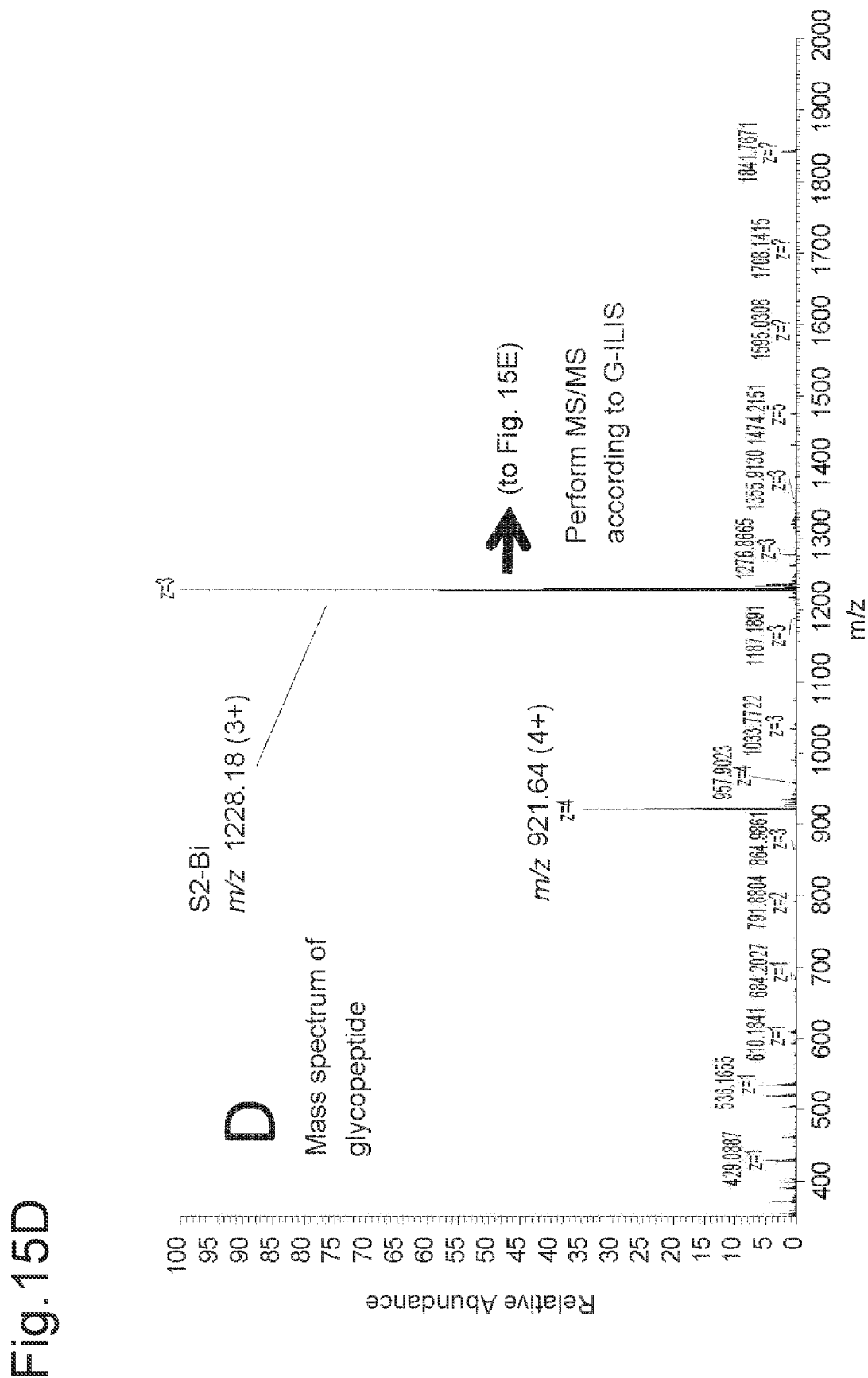

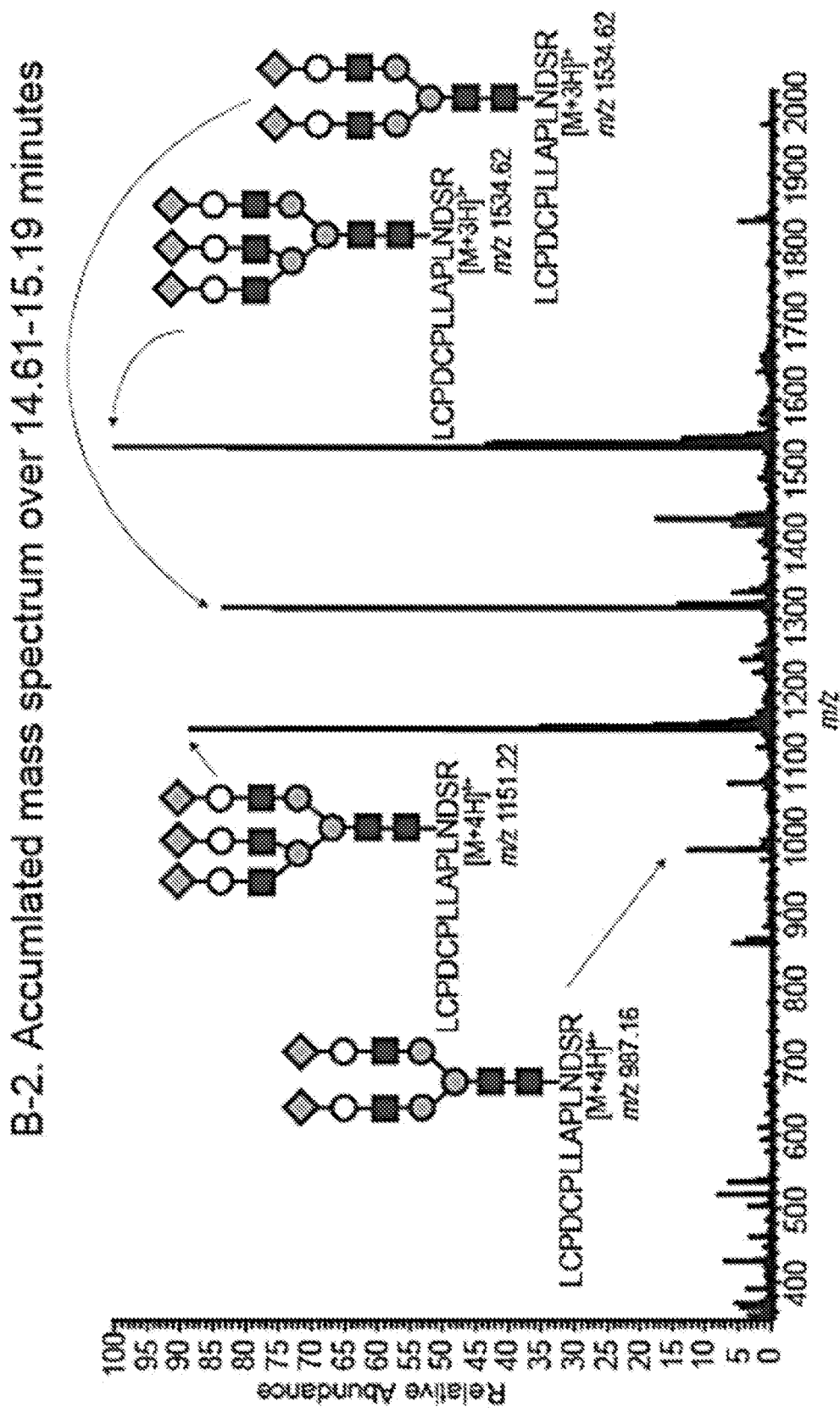

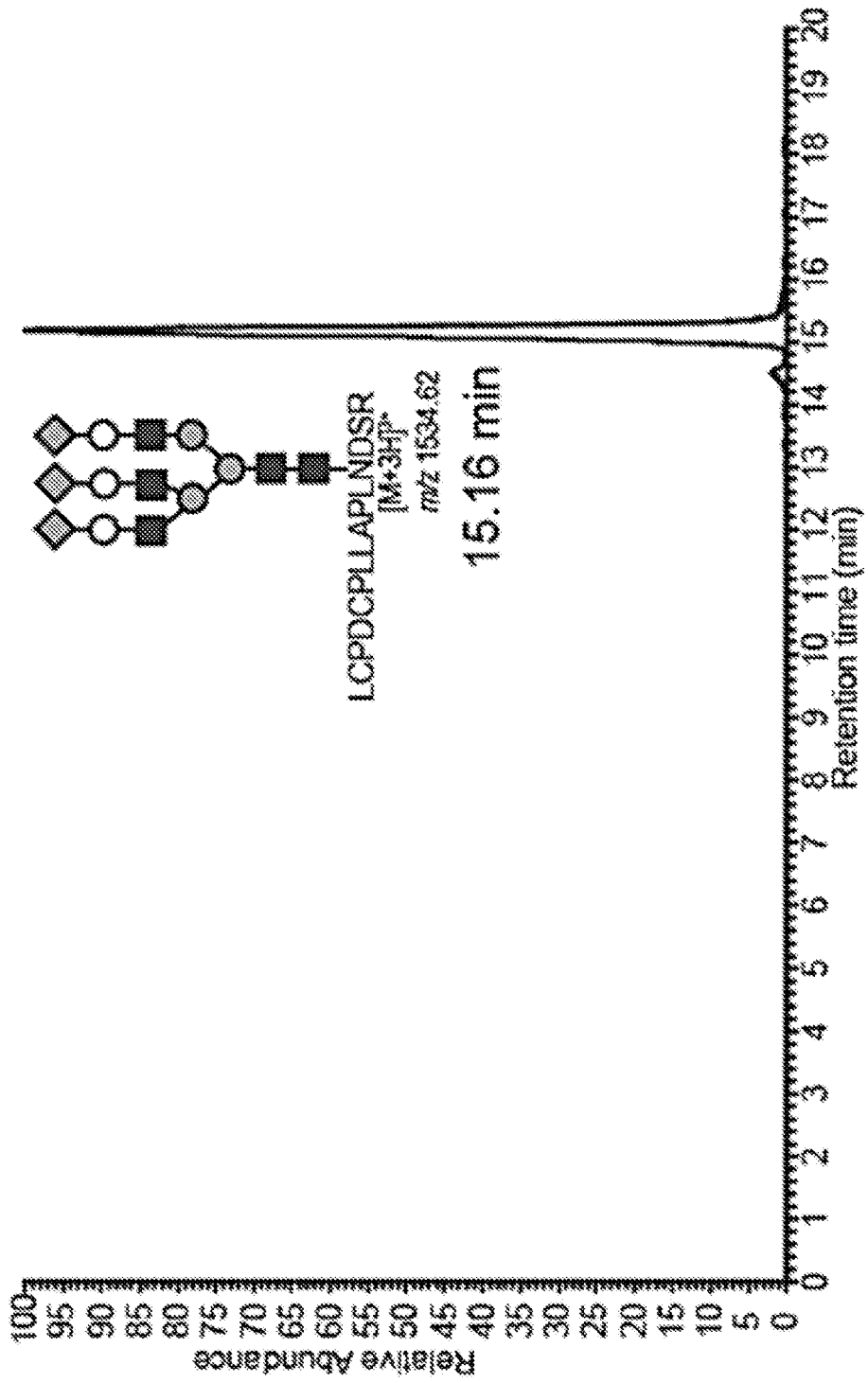

```
                         SEQUENCE LISTING

<160> NUMBER OF SEQ ID NOS: 9

<210> SEQ ID NO 1
<211> LENGTH: 9
<212> TYPE: PRT
<213> ORGANISM: Homo sapiens

<400> SEQUENCE: 1

Glu Glu Gln Tyr Asn Ser Thr Tyr Arg
1               5

<210> SEQ ID NO 2
<211> LENGTH: 9
<212> TYPE: PRT
<213> ORGANISM: Homo sapiens

<400> SEQUENCE: 2

Glu Glu Gln Phe Asn Ser Thr Phe Arg
1               5

<210> SEQ ID NO 3
<211> LENGTH: 9
<212> TYPE: PRT
<213> ORGANISM: Homo sapiens

<400> SEQUENCE: 3

Glu Glu Gln Tyr Asn Ser Thr Phe Arg
1               5

<210> SEQ ID NO 4
<211> LENGTH: 9
<212> TYPE: PRT
<213> ORGANISM: Homo sapiens

<400> SEQUENCE: 4

Glu Glu Gln Phe Asn Ser Thr Tyr Arg
1               5

<210> SEQ ID NO 5
<211> LENGTH: 9
<212> TYPE: PRT
<213> ORGANISM: Artificial Sequence
<220> FEATURE:
<223> OTHER INFORMATION: IgG1 glycopeptide in which Asn is converted to
      Asp

<400> SEQUENCE: 5

Glu Glu Gln Tyr Asp Ser Thr Tyr Arg
1               5

<210> SEQ ID NO 6
<211> LENGTH: 6
```

```
<212> TYPE: PRT
<213> ORGANISM: Bovine

<400> SEQUENCE: 6

Ser Arg Asn Leu Thr Lys
1               5

<210> SEQ ID NO 7
<211> LENGTH: 13
<212> TYPE: PRT
<213> ORGANISM: Homo sapiens

<400> SEQUENCE: 7

Cys Gly Leu Val Pro Val Leu Ala Glu Asn Tyr Asn Lys
1               5                   10

<210> SEQ ID NO 8
<211> LENGTH: 15
<212> TYPE: PRT
<213> ORGANISM: Bovine

<400> SEQUENCE: 8

Leu Cys Pro Asp Cys Pro Leu Leu Ala Pro Leu Asn Asp Ser Arg
1               5                   10                  15

<210> SEQ ID NO 9
<211> LENGTH: 16
<212> TYPE: PRT
<213> ORGANISM: Homo sapiens

<400> SEQUENCE: 9

Ser Val Gln Glu Ile Gln Ala Thr Phe Phe Tyr Phe Thr Pro Asn Lys
1               5                   10                  15
```

METHOD AND SYSTEM FOR ANALYZING N-LINKED SUGAR CHAINS OF GLYCOPROTEIN

TECHNICAL FIELD

The present invention relates to a method and system for analyzing N-linked sugar chains using liquid chromatography/mass spectrometry.

BACKGROUND ART

Sugar chains are important post-translational modifications of proteins. In recent years, analyses of their structures and functions have been rapidly advanced. As methods for such analysis of glycoproteins and glycopeptides, a method using liquid chromatography/mass spectrometry has been widely used. One of the most common techniques for analyzing the structures of N-linked glycoproteins and glycopeptides using liquid chromatography/mass spectrometry is to cleave sugar chains off with peptide-N-glycanase (PNGase F), change the asparagine (Asn) to which an N-linked sugar chain is bound into aspartic acid (Asp), and detect this change, thereby determining a position where the N-linked sugar chain is bound (see, for example, Patent Document 1 and Non-patent Document 1).

However, the methods of observing the change of Asn present in an N-glycosylation site to Asp using PNGase F have two problems: one is that it can not be determined whether the change to Asp is due to deamidation of Asn or due to treatment with PNGase F; and the other is that misidentification tends to frequently occur due to the change in mass from Asn to Asp being as small as +1 Da.

These problems have been handled, for example, by a method in which sugar chain cleavage is carried out in stable isotopically labeled $H_2^{18}O$ to label the hydroxy group of the carboxyl group of Asp with $^{18}O$ during conversion of Asn at the glycosylation site into Asp. According to this method, the change in mass becomes +3 Da, which makes it possible to discriminate the conversion of Asn from deamidation of Asn, thereby reducing misidentification due to mistakes in monoisotopic peak picking (see, for example, Non-Patent Document 1).

As for quantitative analysis of sugar chains released from glycoproteins or glycopeptides, a method in which all N-linked sugar chains are cleaved off and released from proteins with PNGase F, labeled, and then measured using liquid chromatography or the like is well known (see, for example, Patent Document 2).

PRIOR ART REFERENCE(S)

Patent Document(S)

Patent Document 1: JP 2015-142555 A
Patent Document 2: JP 2009-145169 A

NON-PATENT DOCUMENT(S)

Non-Patent Document 1: Kaji, H. et al. (2003) Lectin affinity capture, isotope-coded tagging and mass spectrometry to identify N-linked glycoproteins. Nat Biotechnol, 21, 667-672

SUMMARY OF THE INVENTION

Problems to be Solved by the Invention

However, there are problems, for example, the following three problems, in the qualitative and quantitative analyses of sugar chains of glycoproteins and glycopeptides.

The first problem is that when Asn in the N-glycosylation site is changed to Asp with PNGase F, the mass change is only +1 Da. Even though a mass change becomes +3 Da when stable isotope labeling with $^{18}O$ is carried out, the mass change by +3 Da is also hardly considered to be sufficiently distinguishable in mass spectrometry. For proper distinction in mass spectrometry, a mass change by +5 Da or more is desirable, and only +3 Da change tends to cause misidentification.

The second problem is caused from the facts that glycosylation occurs in a large variety of proteins, and that a plurality of glycosylation may often occur in one protein. When all sugar chains are cleaved off and released from a glycoprotein or glycopeptide with PNGase F, it is impossible to determine which sugar chain has been bonded to which Asn, and thus it is impossible to quantitatively analyze sugar chains at each of the glycosylation sites individually and separately from one glycosylation site another. In order to quantitatively analyze sugar chains at each of the glycosylation sites individually and separately from one glycosylation site another, analysis must be performed on glycoprotein or glycopeptide without cleaving off sugar chains with PNGase F.

The third problem is that ionization efficiency in mass spectrometry of glycoproteins and glycopeptides is poor compared to proteins and peptides, and thus, it is difficult to acquire data using a glycoprotein or glycopeptide as a precursor ion in data dependent $MS^n$ analysis.

The present invention has been made in view of the above-described circumstances, and aims at providing a means for enabling accurate qualitative and quantitative analyses of N-linked sugar chains at each glycosylation site.

Means for Solving the Problems

The present inventors have intensively studied to find that the above-described problems can be solved by: treating a part of a glycopeptide-containing sample to be analyzed with endo-β-N-acetylglucosaminidases to cleave off sugar chains while leaving one N-acetylglucosamine (GlcNAc) of the chitobiose core on the Asn at the N-glycosylation site; subjecting the obtained sugar chain-cleaved sample to preliminary liquid chromatography/mass spectrometry; predicting the retention time of the glycopeptide of interest and the mass-to-charge ratio (m/z) of the precursor ion in main analysis based on the results of the preliminary liquid chromatography/mass spectrometry; and carrying out the main analysis, thereby completing the following invention.

(1) A method of analyzing N-linked sugar chain(s) of glycoprotein, comprising:

a glycoprotein fragmentation step of fragmenting glycoprotein having N-linked sugar chain(s) to obtain a glycopeptide-containing sample;

a sugar chain cleavage step of allowing a part of the glycopeptide-containing sample to react with an endo-β-N-acetylglucosaminidase(s) and cleaving the β-1,4 linkage in chitobiose present at a junction between each sugar chain and an asparagine (Asn) residue, thereby cleaving off the sugar chain(s) while leaving one N-acetylglucosamine (GlcNAc) residue (optionally, one fucose (Fuc) residue is bound to said GlcNAc) on the peptide;

a preliminary liquid chromatography/mass spectrometry step of subjecting a sugar chain-cleaved peptide sample obtained in the sugar chain cleavage step to liquid chromatography/mass spectrometry to obtain chromatogram, mass spectrum and product ion spectrum;

a glycosylation site determination step of performing MS/MS ion search or de novo sequencing taking into account the GlcNAc or GlcNAc-Fuc modification on the Asn residue to determine the glycosylation site in the glycopeptide;

a retention time and m/z estimation step of estimating the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing; and a main analysis step of subjecting the remainder of the glycopeptide-containing sample to liquid chromatography/mass spectrometry, selecting the precursor ion peak(s) to be analyzed based on the results of estimation of the retention time and m/z, and performing precursor ion-selected mass spectrometry for the selected peak(s) to determine the sugar chain structure of the glycopeptide.

(2) The method according to (1), wherein the endo-β-N-acetylglucosaminidase(s) comprise(s) one or two or more selected from Endo F1, Endo F2, Endo F3, Endo M, Endo H and Endo S.

(3) The method according to (1) or (2), wherein a sample in which glycopeptides are concentrated by removing peptides to which no sugar chains are bound is used as the glycopeptide sample.

(4) The method according to any one of (1) to (3), further comprising adding, as an internal standard, the sugar chain-cleaved peptide sample obtained in the sugar chain cleavage step to the remainder of the glycopeptide-containing sample, and performing the main analysis step to relatively quantify sugar chains present on the glycosylation site.

(5) The method according to (4), wherein a sugar chain-cleaved peptide sample from which glycopeptides whose sugar chains are not cleaved off are removed is used as the internal standard.

(6) The method according to (5), wherein removal of glycopeptides whose sugar chains are not cleaved off is carried out by a method of adding cold acetone to a sugar chain-cleaved peptide sample and precipitating the glycopeptides whose sugar chains are not cleaved off to separate them, or by adsorbing and removing the glycopeptides whose sugar chains are not cleaved off by hydrophilic interaction chromatography.

(7) A system for analyzing N-linked sugar chain(s) of glycoprotein, comprising:

a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one GlcNAc residue (optionally, one Fuc residue is bound to said GlcNAc) on the Asn residue of the peptide by reaction with an endo-β-N-acetylglucosaminidase(s);

a glycosylation site determination unit that performs MS/MS ion search or de novo sequencing taking into account the GlcNAc or GlcNAc-Fuc modification on the Asn residue to determine the glycosylation site in the glycopeptide;

a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;

a main analysis unit that performs main analysis on a main analysis sample, which is the glycopeptide-containing sample before the sugar chain cleavage; and an output unit that outputs analysis results, wherein said main analysis unit comprises:

a unit for acquisition of liquid chromatography/mass spectrometry data of the main analysis sample that acquires chromatogram of the main analysis sample and mass spectrum of a fraction at the estimated retention time;

a target peak selection unit that selects a precursor ion peak(s) to be analyzed from said mass spectrum of the fraction at the estimated retention time based on the m/z estimation result; and a sugar chain structure determination unit that acquires precursor ion-selected mass spectrometry data for the selected target peak(s) and determines the sugar chain structure of the glycopeptide.

(8) A system for analyzing N-linked sugar chain(s) of glycoprotein, comprising:

a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one GlcNAc residue (optionally, one Fuc residue is bound to said GlcNAc) on the Asn residue of the peptide by reaction with an endo-β-N-acetylglucosaminidase(s);

a glycosylation site determination unit that performs MS/MS ion search or de novo sequencing taking into account the GlcNAc or GlcNAc-Fuc modification on the Asn residue to determine the glycosylation site in the glycopeptide;

a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;

a main analysis unit that performs main analysis on a main analysis sample, which is the glycopeptide-containing sample before the sugar chain cleavage; and an output unit that outputs analysis results, wherein said main analysis unit comprises:

a unit for acquisition of liquid chromatography/mass spectrometry data of the main analysis sample that acquires chromatogram of the main analysis sample to which the sugar chain-cleaved peptide sample is added as an internal standard, and mass spectrum of a fraction at the estimated retention time;

a target peak selection unit that selects a precursor ion peak(s) to be analyzed from said mass spectrum of the fraction at the estimated retention time based on the m/z estimation result;

a sugar chain structure determination unit that acquires precursor ion-selected mass spectrometry data for the selected target peak(s) and determines the sugar chain structure of the glycopeptide; and a sugar chain quantification unit that relatively quantifies sugar chains present on the glycosylation site by obtaining extracted ion chromatograms of the internal standard and each glycopeptide and calculating the relative intensity of each glycopeptide relative to the internal standard.

(9) A program(s) for analyzing N-linked sugar chain(s) of glycoprotein, said program(s) causing one or more computers to function as:

a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one GlcNAc residue (optionally, one Fuc residue is bound to said GlcNAc) on the Asn residue of the peptide by reaction with an endo-β-N-acetylglucosaminidase(s);

a glycosylation site determination unit that performs MS/MS ion search or de novo sequencing taking into account the GlcNAc or GlcNAc-Fuc modification on the Asn residue to determine the glycosylation site in the glycopeptide;

a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;

a main analysis unit that performs main analysis on a main analysis sample, which is the glycopeptide-containing sample not subjected to sugar chain cleavage treatment with an endo-β-N-acetylglucosaminidase(s); and an output unit that outputs analysis results, wherein said main analysis unit comprises:

a unit for acquisition of liquid chromatography/mass spectrometry data of the main analysis sample that acquires chromatogram of the main analysis sample and mass spectrum of a fraction at the estimated retention time;

a target peak selection unit that selects a precursor ion peak(s) to be analyzed from said mass spectrum of the fraction at the estimated retention time based on the m/z estimation result; and a sugar chain structure determination unit that acquires precursor ion-selected mass spectrometry data for the selected target peak(s) and determines the sugar chain structure of the glycopeptide.

(10) A program(s) for analyzing N-linked sugar chain(s) of glycoprotein, said program(s) causing one or more computers to function as:

a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one GlcNAc residue (optionally, one Fuc residue is bound to said GlcNAc) on the Asn residue of the peptide by reaction with an endo-β-N-acetylglucosaminidase(s);

a glycosylation site determination unit that performs MS/MS ion search or de novo sequencing taking into account the GlcNAc or GlcNAc-Fuc modification on the Asn residue to determine the glycosylation site in the glycopeptide;

a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;

a main analysis unit that performs main analysis on a main analysis sample, which is the glycopeptide-containing sample before the sugar chain cleavage; and an output unit that outputs analysis results, wherein said main analysis unit comprises:

a unit for acquisition of liquid chromatography/mass spectrometry data of the main analysis sample that acquires chromatogram of the main analysis sample to which the sugar chain-cleaved peptide sample is added as an internal standard, and mass spectrum of a fraction at the estimated retention time;

a target peak selection unit that selects a precursor ion peak(s) to be analyzed from said mass spectrum of the fraction at the estimated retention time based on the m/z estimation result;

a sugar chain structure determination unit that acquires precursor ion-selected mass spectrometry data for the selected target peak(s) and determines the sugar chain structure of the glycopeptide; and a sugar chain quantification unit that relatively quantifies sugar chains present on the glycosylation site by obtaining extracted ion chromatograms of the internal standard and each glycopeptide and calculating the relative intensity of each glycopeptide relative to the internal standard.

(11) An internal standard peptide for use in quantitative analysis of glycopeptide contained in a tryptic digest of IgG antibody, composed of a peptide consisting of the amino acid sequence of EEQYNSTYR, EEQFNSTFR, EEQYNSTFR, or EEQFNSTYR, wherein one GlcNAc residue, or one GlcNAc residue with one Fuc residue bound thereto, is bound to the asparagine residue of the peptide.

(12) A method of producing an internal standard for use in quantitative analysis of a sugar chain(s) on an IgG antibody, the method comprising fragmenting an IgG antibody to obtain a peptide mixture, separating and recovering glycopeptides from the peptide mixture, allowing the glycopeptides to react with an endo-β-N-acetylglucosaminidase(s), and then removing glycopeptides whose sugar chains are not cleaved off.

Effect of the Invention

According to the present invention, the binding sites and structures of N-linked sugar chains (qualitative analysis) and the ratio of each sugar chain bound to the respective binding sites (quantitative analysis) in a glycoprotein can be analyzed. In the present invention, N-linked sugar chains are cleaved off while leaving one GlcNAc residue (one Fuc residue may be bound to the GlcNAc) on Asn of a peptide, which leads to a large mass change by +203 Da (when Fuc is bound, the change is +349 Da), thereby enabling proper detection of mass changes in mass spectrometry and thus prevention of false detection. Further, unlike conventional techniques in which Asn is converted into Asp, the present invention does not cause any charge change in the peptides, and therefore change in the chromatography retention time is unlikely to occur between before and after sugar chain cleavage. Thus, based on the results of preliminary analysis of the sugar chain-cleaved peptide on which one GlcNAc residue is left, the chromatography retention time of a sample to be subjected to main analysis from which sugar chains are not cleaved off can be predicted with a high accuracy. Based on the preliminary analysis results, the liquid chromatography retention time and the m/z of precursor ions which will be obtained when the main analysis of the glycopeptide sample before the sugar chain cleavage is carried out are predicted, which allows for proper selection of peaks to be analyzed, and thus efficient sugar chain analysis becomes possible. In addition, the glycopeptide from which sugar chains have been cleaved off while leaving one GlcNAc residue thereon, which is used in the preliminary analysis, may be used as an internal standard in the main analysis, by which quantitative analysis for relative quantification of sugar chains at each of the glycosylation sites becomes possible.

BRIEF DESCRIPTION OF THE DRAWINGS

FIGS. 9A and 9B show the base peak chromatogram and the mass spectrum of an internal standard substance for use in the second embodiment, prepared from a human myeloma-derived IgG1. In this internal standard substance, sugar chains have been cleaved off, with GlcNAc or GlcNAc-Fuc left on the peptide, and this internal standard does not contain undeglycosylated impurities.

FIG. 13A; A base peak chromatogram of the peptide (hereinafter referred to as G-TAG) prepared by cleaving off sugar chains from glycopeptides obtained by trypsin digestion of IgG1 while leaving GlcNAc, Fuc on the peptide. The retention time of G-TAG was 11.53 min. FIG. 13B; A mass spectrum of G-TAG derived from IgG1. From this result, estimates of the m/z of glycopeptides before the sugar chain cleavage were calculated and listed. FIG. 13C; A product ion spectrum of G-TAG derived from IgG1. From this result, glycosylation sites of the IgG1 were determined. FIG. 13D; A base peak chromatogram of IgG1-derived glycopeptides before the sugar chain cleavage. A glycopeptide peak was observed at a retention time (11.37 min) very close to that of G-TAG. FIG. 13E; A mass spectrum of a fraction with the retention time around 11.37 min. Ions derived from the IgG1-derived glycopeptides were detected. From the results of the G-TAG analysis, it was confirmed that m/z of glycopeptides could be predicted. FIG. 13F; As an example of product ion spectrum obtained by G-ILIS (Glycopeptide-inclusion list data-dependent acquisition MS) list-dependent MS/MS, a product ion spectrum and fragment assignments for glycopeptides to which G2F, a representative sugar chain of IgG1, was bound were shown.

FIGS. 14A, 14B, 14C, 14D, and 14E show results of Analysis Example 2 in which sugar chains of RNase B, as one example of high-mannose glycosylated proteins, were analyzed according to the method of the present invention. FIG. 14A; An extracted ion chromatogram of the peptide (hereinafter referred to as G-TAG) prepared by cleaving off sugar chains from glycopeptides obtained by trypsin digestion of RNase B while leaving GlcNAc on the peptide. The retention time of G-TAG was 7.02 min. FIG. 14B; A mass spectrum of G-TAG derived from RNase B. From this result, estimates of the m/z of glycopeptides before the sugar chain cleavage were calculated and listed. FIG. 14C; An extracted ion chromatogram of glycopeptide to which Man5, a representative sugar chain contained in RNase B, was bound (a glycopeptide in which a sugar chain as shown (circles indicate mannose) was bound to N in SRNLTK). A glycopeptide peak was observed at a retention time (7.26 min) very close to that of G-TAG. FIG. 14D; A mass spectrum of a fraction with the retention time around 7.26 min. From the results of the G-TAG analysis, it was confirmed that m/z of glycopeptides could be predicted. FIG. 14E; As an example of product ion spectrum obtained by G-ILIS list-dependent MS/MS, a product ion spectrum and fragment assignments for glycopeptides to which Man5 was bound were shown.

FIGS. 15A, 15B, 15C, 15D, and 15E show results of Analysis Example 3 in which sugar chains of transferrin (Tf), as one example of sialylated complex biantennary glycosylated proteins, were analyzed according to the method of the present invention. FIG. 15A; An extracted ion chromatogram of the peptide (hereinafter referred to as G-TAG) prepared by cleaving off sugar chains, while leaving GlcNAc thereon, from glycopeptides having the sequence CGLVPVLAENYNK which were obtained by trypsin digestion of a reduced carbamidomethylated product of Tf. The retention time of G-TAG was 13.41 min. FIG. 15B; A mass spectrum of G-TAG derived from Tf. From this result, estimates of the m/z of glycopeptides before the sugar chain cleavage were calculated and listed. FIG. 15C; An extracted ion chromatogram of glycopeptide to which a disialyl biantennary sugar chain (S2-Bi), a representative sugar chain contained in Tf, was bound (a glycopeptide in which a sugar chain as shown was bound to the 10th N in CGLVPVLAENYNK). A glycopeptide peak was observed at a retention time (14.12 min) very close to that of G-TAG. FIG. 15D; A mass spectrum of a fraction with the retention time around 7.26 min. From the results of the G-TAG analysis, it was confirmed that m/z of glycopeptides could be predicted. FIG. 15E; As an example of product ion spectrum obtained by G-ILIS list-dependent MS/MS, a product ion spectrum and fragment assignments for glycopeptides to which S2-Bi was bound were shown.

FIGS. 16A-1, 16A-2, 16A-3, 16B-1, 16B-2, 16B-3, and 16B-4 show results of Analysis Example 4 in which sugar chains of fetuin, as one example of sialylated complex triantennary glycosylated proteins, were analyzed according to the method of the present invention. FIG. 16A-1; An extracted ion chromatogram of the peptide (hereinafter referred to as G-TAG) prepared by cleaving off sugar chains, while leaving GlcNAc thereon, from glycopeptides having the sequence LCPDCPLLAPLNDSR which were obtained by trypsin digestion of a reduced carbamidomethylated product of fetuin. The retention time of G-TAG was 13.85 min. FIG. 16A-2; A mass spectrum of G-TAG derived from fetuin. From this result, estimates of the m/z of glycopeptides before the sugar chain cleavage were calculated and listed. FIG. 16A-3; A product ion spectrum of G-TAG. FIG. 16B-1; A total ion current chromatogram of fetuin-derived glycopeptides before the sugar chain cleavage. Glycopeptides having the sequence LCPDCPLLAPLNDSR were predicted to be eluted within 2.5 min before and 2.5 min after the retention time of G-TAG. FIG. 16B-2; A mass spectrum of a fraction with a retention time from 14.61 to 15.19 min. Ion peaks of glycopeptides having the sequence LCPDCPLLAPLNDSR were detected. From the results of the G-TAG analysis, it was confirmed that m/z of glycopeptides could also be predicted. FIG. 16B-3; An extracted ion chromatogram of glycopeptide in which trisialyl triantennary sugar chain, a representative sugar chain contained in fetuin, was bound to the N residue in the sequence LCPDCPLLAPLNDSR (m/z 1534.62; a glycopeptide to which a sugar chain as shown was bound). FIG. 16B-4; A product ion spectrum obtained from a glycopeptide of m/z 1534.62 as a precursor ion, and assignments of main fragments.

FIGS. 17A-1 17A-2, 17A-3, 17B-1, 17B-2, 17B-3, and 17B-4 show results of Analysis Example 5 in which sugar chains of α1-acid glycoprotein, as one example of sialylated complex tetraantennary glycosylated proteins, were analyzed according to the method of the present invention. FIG. 17A-1; An extracted ion chromatogram of the peptide (hereinafter referred to as G-TAG) prepared by cleaving off sugar chains, while leaving GlcNAc thereon, from glycopeptides having the sequence SVQEIQATFFYFTPNK which were obtained by trypsin digestion of α1-acid glycoprotein. The retention time of G-TAG was 15.32 min. FIG. 17A-2; A mass spectrum of G-TAG derived from α1-acid glycoprotein. From this result, estimates of the m/z of glycopeptides before the sugar chain cleavage were calculated and listed. FIG. 17A-3; A product ion spectrum of G-TAG. FIG. 17B-1; A total ion current chromatogram of α1-acid glycoprotein-derived glycopeptides before the sugar chain cleavage. Glycopeptides having the sequence SVQEIQATFFYFTPNK were predicted to be eluted within 2.5 min before and 2.5 min after the retention time of G-TAG. FIG. 17B-2; A mass spectrum of a fraction with a retention time from 15.83 to 17.75 min. Ion peaks of glycopeptides having the sequence SVQEIQATFFYFTPNK were detected. From the results of the G-TAG analysis, it was confirmed that m/z of glycopeptides could also be predicted. FIG. 17B-3; An extracted ion chromatogram of glycopeptide in which a tetrasialyl tetraantennary sugar chain, a representative sugar chain contained in α1-acid glycoprotein, was bound to the N residue in the sequence SVQEIQATFFYFTPNK (m/z 1813.07; a glycopeptide to which a sugar chain as shown was bound). FIG. 17B-4; A product ion spectrum obtained from a glycopeptide with a peak at m/z 1813.07 as a precursor ion, and assignments of main fragments.

MODE FOR CARRYING OUT THE INVENTION

Figure 1:
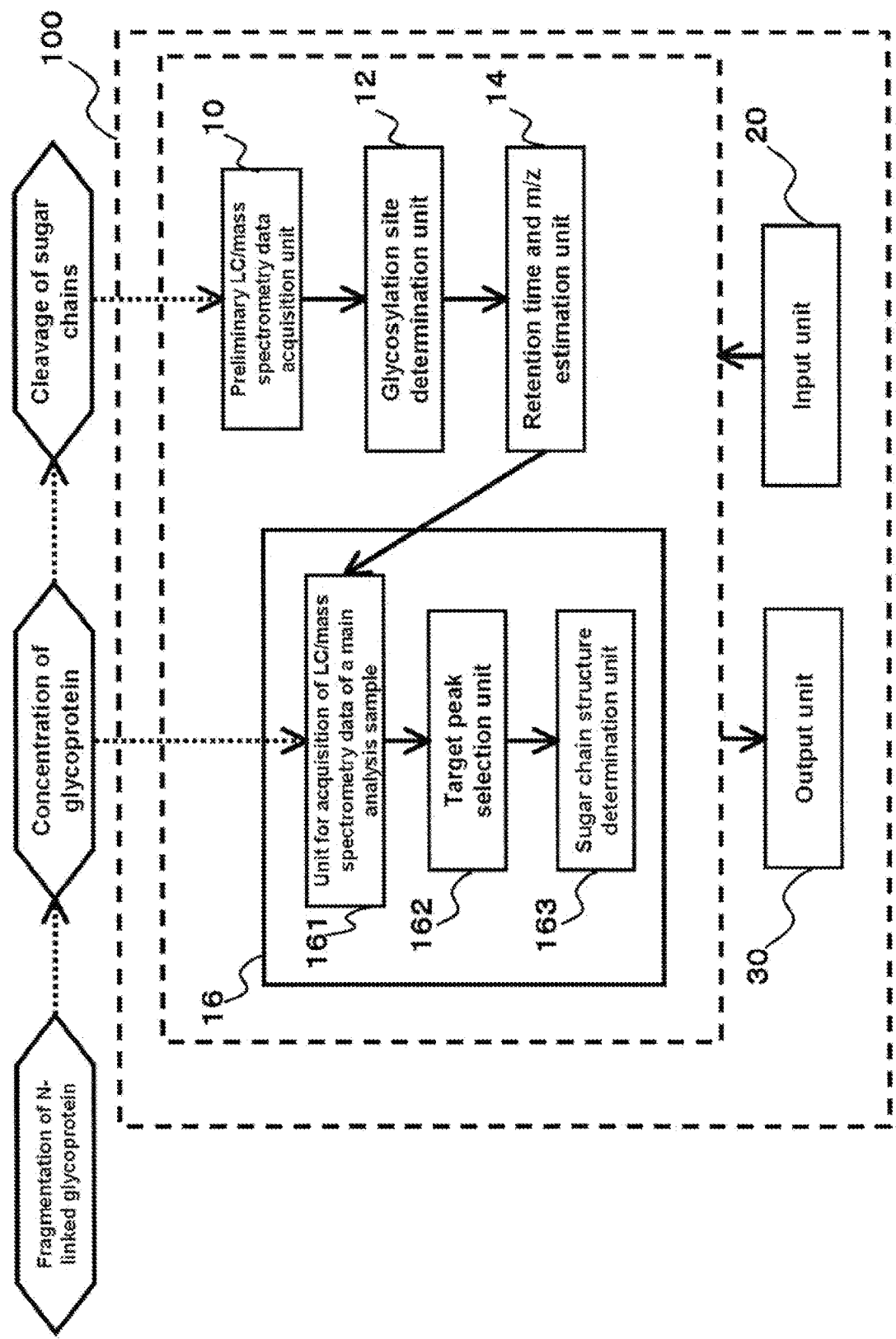
FIG. 1 is a block diagram illustrating an example of a configuration of the system for analyzing N-linked sugar chains according to the first embodiment of the present invention.

Glycoproteins to be analyzed by the present invention are not restricted as long as they have N-linked sugar chain(s). Glycoproteins having both N- and O-linked sugar chains may also be analyzed by the present invention.

Methods of analyzing N-linked sugar chains according to the present invention include the following two embodiments. In the first embodiment, a qualitative analysis is carried out, in which the structure of glycoprotein or glycopeptide (the binding site(s) of N-linked sugar chain(s) in a glycoprotein or glycopeptide molecule and the structure(s) of the N-linked sugar chain(s) bound thereto) is determined. In the second embodiment, the structures and the ratios of N-linked sugar chains are relatively quantified at each of the glycosylation sites individually and separately from one glycosylation site another.

Hereinafter, the steps that are common between the first and the second embodiments will be first described, and then the steps characteristic of the second embodiment will be described.

The method of analyzing N-linked sugar chain(s) of the present invention comprises: a glycoprotein fragmentation step; a sugar chain cleavage step; a preliminary liquid chromatography/mass spectrometry step; a glycosylation site determination step; a retention time and m/z estimation step; and a main analysis step.

In the glycoprotein fragmentation step, a glycoprotein having N-linked sugar chain(s) is fragmented to obtain a glycopeptide-containing sample. Enzymes that specifically cleave peptides at specific sequence sites, such as trypsin and Asp-N, can be used. However, any known fragmentation method can be used without limitation. In general, glycoproteins are reduced and alkylated prior to fragmentation.

The glycopeptide-containing sample obtained in this step is a mixture of peptides with a sugar chain(s) bound thereto (glycopeptide) and peptides without a sugar chain(s) bound thereto. Optionally, the peptides without a sugar chain(s) bound thereto may be removed to concentrate the glycopeptides. In that case, a glycopeptide-containing sample may be obtained by separating and recovering glycopeptides by a conventional method, such as a method comprising adding cold acetone and recovering the precipitated glycopeptides, or hydrophilic interaction chromatography with cellulose.

The glycopeptide-containing sample obtained in the glycoprotein fragmentation step is partly subjected to the sugar chain cleavage step to obtain a preliminary analysis sample, and a remainder (all or a part of the remainder) is used as a main analysis sample.

In the sugar chain cleavage step, a part of the glycopeptide-containing sample obtained in the glycoprotein fragmentation step is allowed to react with an endo-β-N-acetylglucosaminidase(s) to cleave the β-1,4 linkage in chitobiose present at a junction between each sugar chain and an asparagine (Asn) residue, thereby cleaving off the sugar chain(s) while leaving one GlcNAc residue on the peptide. One Fuc residue may be bound to the GlcNAc left on the peptide.

Any class of endo-β-N-acetylglucosaminidases can be used. Specific examples of endo-β-N-acetylglucosaminidases that can be used include Endo F1, Endo F2, Endo F3, Endo M, Endo H and Endo S. One, or two or more, for example, three or more, four or more, five or more selected from, or all of such endo-β-N-acetylglucosaminidases can be used. Even three enzymes, Endo F1, Endo F2, and Endo F3, or Endo M alone can cover many glycoproteins. However, as many endo-β-N-acetylglucosaminidases as possible may be used so that all N-linked sugar chains contained in the fragmented glycoprotein sample can be cleaved off. When the glycopeptide-containing sample is treated with a plurality of endo-β-N-acetylglucosaminidases, all of the enzymes may be allowed to react with the sample simultaneously or sequentially. Further, before the treatment with endo-β-N-acetylglucosaminidase(s), the glycopeptide-containing sample may be treated with other sugar chain cleaving enzymes (e.g., neuraminidase, β-galactosidase).

In the preliminary liquid chromatography/mass spectrometry step, the sugar chain-cleaved peptide sample obtained in the sugar chain cleavage step is subjected to liquid chromatography/mass spectrometry to obtain chromatogram, mass spectrum and product ion spectrum. The liquid chromatography/mass spectrometry itself can be carried out according to conventional methods. For the mass spectrometry, a mass spectrometer such as electrostatic field ion trap mass spectrometer (Orbitrap type) with collision-induced dissociation (CID) or quadrupole ion trap mass spectrometer can be used. In mass spectrometry using CID, peptides comprising a GlcNAc are sequentially measured through product ion scans by MS$^n$ (n is an integer of 2 or more) by repeating a series of operations comprising ion cleavage and mass spectrometry with a detector.

In the glycosylation site determination step, the glycosylation site(s) in each glycopeptide is/are determined by MS/MS ion search or de novo sequencing, taking into account the GlcNAc or GlcNAc-Fuc modification on the Asn residue in the glycopeptide (i.e., on condition that GlcNAc or GlcNAc-Fuc is added to Asn). For the MS/MS ion search or de novo sequencing, any known algorithms and softwares can be used.

When the original glycoprotein has N-linked sugar chains at a plurality of positions in the molecule, the sugar chain-cleaved peptides comprise a plurality of varieties of GlcNAc- or GlcNAc-Fuc-binding peptides having different peptide sequences. Therefore, the glycosylation site may be determined by performing MS/MS ion search or de novo sequencing taking into account the GlcNAc or GlcNAc-Fuc modification, for each of the plurality of varieties of GlcNAc- or GlcNAc-Fuc-binding peptides.

In the retention time and m/z estimation step, the liquid chromatography retention time and the mass-to-charge ratio (m/z) of the precursor ion in the main analysis of the glycopeptide-containing sample before the sugar chain cleavage are estimated based on the results of the preliminary liquid chromatography/mass spectrometry and MS/MS ion search or de novo sequencing described above.

The liquid chromatography retention time of the main analysis sample ($Rt_{Glycosylated}$) may be estimated by adding the difference Δt to or subtracting it from $Rt_{Peptide+GlcNAc}$, a liquid chromatography retention time obtained in the preliminary analysis for the sugar chain-cleaved peptide sample, as shown in the following Formula 1. This gives estimation of the numerical range of $Rt_{Glycosylated}$.

$$Rt_{Glycosylated} = Rt_{Peptide+GlcNAc} + \Delta t \quad \text{Formula 1}$$

The Δt value, which is any suitable value arbitrarily input by an analyst, is generally about 3 minutes or less when general analysis conditions are used in liquid chromatography/mass spectrometry in the main analysis, and may be, for example, 2 minutes or less, or 1 minute or less. In the present invention, unlike the conventional method in which Asn is converted into Asp, sugar chain cleavage does not cause electric charge change in the peptide. Thus, the chromatography retention time is unlikely to change before and after the sugar chain cleavage, and sugar chain-cleaved peptides are eluted at about the same position as the glycopeptide before the sugar chain cleavage. Therefore, the Δt value can be as small as about 3 minutes or less.

For m/z estimation, the monoisotopic mass of a sugar chain-cleaved peptide is calculated based on the results from MS/MS ion search or de novo sequencing performed in the glycosylation site determination step. Then, the mass of an appropriate sugar chain is added to the monoisotopic mass to estimate the monoisotopic mass of a glycopeptide in the main analysis sample. Specifically, a method in which possible monoisotopic masses of sugar chains consisting of monosaccharides such as hexose, N-acetylhexosamine, fucose, sialic acid, and the like are comprehensively covered; and a method in which monoisotopic masses of sugar chains that can be attached as an N-linked sugar chain are comprehensively considered from a sugar chain database such as GlycomeDB (http://glycome-db.org), can be used.

The former method in which possible monoisotopic mass of sugar chains consisting of monosaccharides are comprehensively covered can be carried out as follows. When assuming, for example, hexose (at least 3 up to 12, monoisotopic mass: 162.0528), N-acetylhexosamine (at least 1 up to 9, monoisotopic mass: 203.0794), fucose (at least 0 up to 4, monoisotopic mass: 146.0579), and N-acetylneuraminic acid (at least 0 up to 4, monoisotopic mass: 291.0954), the number of kinds of the the monoisotopic masses of all possible sugar chains is:

(12−3+1)×(9−1+1)×(4−0+1)×(4−+1)=2250.

All of them can be calculated on a computer, and added to the monoisotopic masses of the peptides from which sugar chains are cleaved off while leaving GlcNAc (or GlcNAc-Fuc) on each peptide, thereby covering all the monoisotopic masses of the possible glycopeptides. The number of each monosaccharide constituting an N-linked sugar chain is definite to some extent depending on the organism species. For example, in human, the number of hexose (mannose, glucose, and galactose) basically ranges from 3 to 12 in total as described above, due to the mechanism of the N-linked sugar chain biosynthetic pathway. The following table shows the possible number of each monosaccharide in N-linked sugar chains of human glycoproteins.

TABLE 1

| Monosaccharide name | Monoisotopic mass | Possible number |
|---|---|---|
| N-acetylglucosamine | 203.0794 | 1-9 |
| N-acetylgalactosamine | | |
| mannose | 162.0528 | 3-12 |
| glucose | | |
| galactose | | |
| fucose | 146.0579 | 0-4 |
| N-acetylneuraminic acid | 291.0954 | 0-4 |

When the original glycoprotein has N-linked sugar chains at a plurality of positions in the molecule, the retention time and m/z may be estimated for each of the plurality of varieties of GlcNAc- or GlcNAc-Fuc-binding peptides.

In the main analysis step, the structure of the sugar chain on the glycopeptide is determined by subjecting a remainder of the glycopeptide-containing sample obtained in the glycoprotein fragmentation step to liquid chromatography/mass spectrometry, selecting a mass spectrum peak(s) to be analyzed based on the estimation results for the retention time and m/z which are estimated above, and carrying out precursor ion-selected mass spectrometry for the selected peak(s).

The liquid chromatography/mass spectrometry analysis in the main analysis step is performed under the same conditions as the liquid chromatography/mass spectrometry analysis in the preliminary analysis. In the liquid chromatography/mass spectrometry analysis of the main analysis, a fraction at the above-estimated retention time (this fraction comprises the glycopeptide to be analyzed) is subjected to mass spectrometry. From the obtained mass spectrum, a peak with the above-estimated m/z is selected and subjected to precursor ion-selected mass spectrometry (mainly product ion scan). Known scoring algorithms such as Sequest, MASCOT, and X!Tandem may be used to determine the glycopeptide structure.

When the original glycoprotein has sugar chains at a plurality of positions, each glycopeptide having a peptide moiety with different amino acid sequence may be subjected to liquid chromatography/mass spectrometry and precursor ion-selected mass spectrometry using the estimation results for the retention time and m/z, to determine the structure of sugar chain on each of the glycopeptides.

For the quantitative analysis of sugar chains of the second embodiment, the sugar chain-cleaved peptide sample obtained in the sugar chain cleavage step is added to the remainder of the glycopeptide-containing sample as an internal standard, and then the main analysis step is performed. It is preferred to use as an internal standard a sugar chain-cleaved peptide sample from which glycopeptides whose sugar chains are not cleaved off are removed. Removal of such sugar chain-noncleaved glycopeptides can be performed, for example, by a method in which sugar chain-noncleaved glycopeptides are precipitated by adding cold acetone and then separated, or a method in which sugar chain-noncleaved glycopeptides are adsorbed and removed using hydrophilic interaction chromatography.

In the sugar chain quantification step, sugar chains present on the glycosylation site are relatively quantified by obtaining mass spectrum of a fraction at the estimated retention time, generating extracted ion chromatograms of the internal standard and each glycopeptide (each of the glycopeptides composed of the same peptide sequence and various sugar chains), and calculating the relative intensity of each glycopeptide relative to the internal standard. For example, a peak area in each of the extracted ion chromatograms may be calculated, and a value may be calculated by dividing the peak area of each glycopeptide by the peak area of the internal standard, as shown in the following Formula 2, and then the obtained values (×100 is optionally carried out) may be compared.

Peak area of each glycopeptide/peak area of internal standard×100  Formula 2

When the original glycoprotein has N-linked sugar chains at a plurality of positions, the internal standard peptide is prepared for each glycosylation site. For example, when the original glycoprotein has N-linked sugar chains at three positions in one molecule, preparation of a glycopeptide sample by fragmenting the glycoprotein may provide three glycopeptides having different peptide sequences. Relative quantification of sugar chains bound to these three glycosylation sites can be made for each of the sites by preparing internal standards for each of these three glycopeptides and performing the main analysis for each glycopeptide.

In the case of analysis of IgG antibodies as a glycoprotein, IgG antibodies whose corresponding antigens are different from each other have the same peptide sequence around their glycosylation sites as long as they belong to the same subtype. For example, when a human IgG antibody against an antigenic protein A and a human IgG antibody against an antigenic protein B are digested with trypsin, and deglycosylated with one GlcNAc or GlcNAc-Fuc residue left on the Asn residue of the peptides by treatment with an endo-β-N-acetylglucosaminidase(s), both of the antibodies provide a peptide in which GlcNAc or GlcNAc-Fuc is bound to N (Asn) in a peptide with the sequence EEQYNSTYR (SEQ ID NO: 1). When a human IgG 2 antibody is digested with trypsin, and deglycosylated with one GlcNAc or GlcNAc-Fuc residue left on the Asn residue of the peptides by treatment with an endo-β-N-acetylglucosaminidase(s), a peptide in which GlcNAc or GlcNAc-Fuc is bound to N in a peptide consisting of EEQFNSTFR (SEQ ID NO: 2) is obtained. When a human IgG 3 antibody is digested with trypsin, and deglycosylated with one GlcNAc or GlcNAc-Fuc residue left on the Asn residue of the peptide by treatment with an endo-β-N-acetylglucosaminidase(s), a peptide in which GlcNAc or GlcNAc-Fuc is bound to N in a peptide consisting of EEQYNSTFR (SEQ ID NO: 3) is obtained. When a human IgG 4 antibody is digested with trypsin, and deglycosylated with one GlcNAc or GlcNAc-Fuc residue left on the Asn residue of the peptide by treatment with an endo-β-N-acetylglucosaminidase(s), a peptide in which GlcNAc or GlcNAc-Fuc is bound to N in a peptide consisting of EEQFNSTYR (SEQ ID NO: 4) is obtained. These do not only apply only to antibodies derived from the same species; antibodies derived from different species may also have the same peptide sequence around their glycosilation sites. Therefore, when the quantitative analysis according to the present invention is performed on an N-linked sugar chain of an IgG antibody, an internal standard prepared from an IgG antibody different from the IgG antibody to be analyzed (subtype must be the same) can be used as long as the same enzyme is used for glycoprotein fragmentation. In such a case, relative quantitative analysis of sugar chains can be made using the same internal standard for different glycoprotein samples, which also enables comparative quantitative evaluation of sugar chains between samples. In a sugar chain analysis of IgG1 antibody, a peptide in which one GlcNAc or GlcNAc-Fuc residue is bound to N in a peptide composed of EEQYNSTYR (SEQ ID NO: 1) may be used as an internal standard peptide. In a sugar chain analysis of IgG2 antibody, a peptide in which one GlcNAc or GlcNAc-Fuc residue is bound to N in a peptide composed of EEQFNSTFR (SEQ ID NO: 2) may be used as an internal standard peptide. In a sugar chain analysis of IgG3 antibody, a peptide in which one GlcNAc or GlcNAc-Fuc residue is bound to N in a peptide composed of EEQYNSTFR (SEQ ID NO: 3) may be used as an internal standard peptide. In a sugar chain analysis of IgG4 antibody, a peptide in which one GlcNAc or GlcNAc-Fuc residue is bound to N in a peptide composed of EEQFNSTYR (SEQ ID NO: 4) may be used as an internal standard peptide. It is well known in the art that the peptide sequence of the glycosylation site in each subtype of IgG antibody is as described above (see, for example, Harazono A, Kawasaki N, Itoh S, Hashii N, Matsuishi-Nakajima Y, Kawanishi T, Yamaguchi T: Simultaneous glycosylation analysis of human serum glycoproteins by high-performance liquid chromatography/tandem mass spectrometry. J. Chromatogr. B. 868, 20-30 (2008)).

Figure 2:
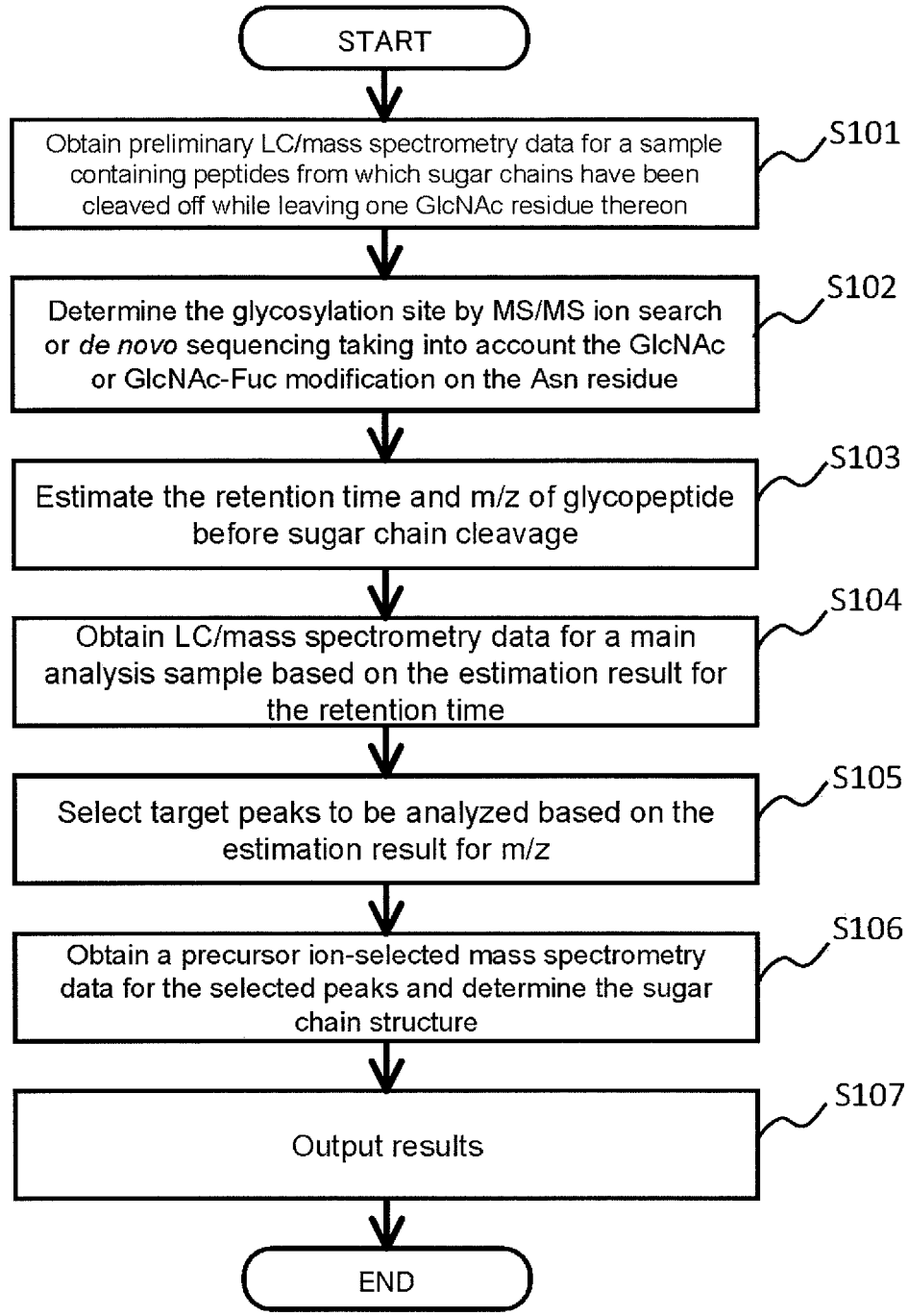
FIG. 2 is a flow chart illustrating one example of a process performed by the system for analyzing N-linked sugar chains according to the first embodiment of the present invention.
Figure 3:
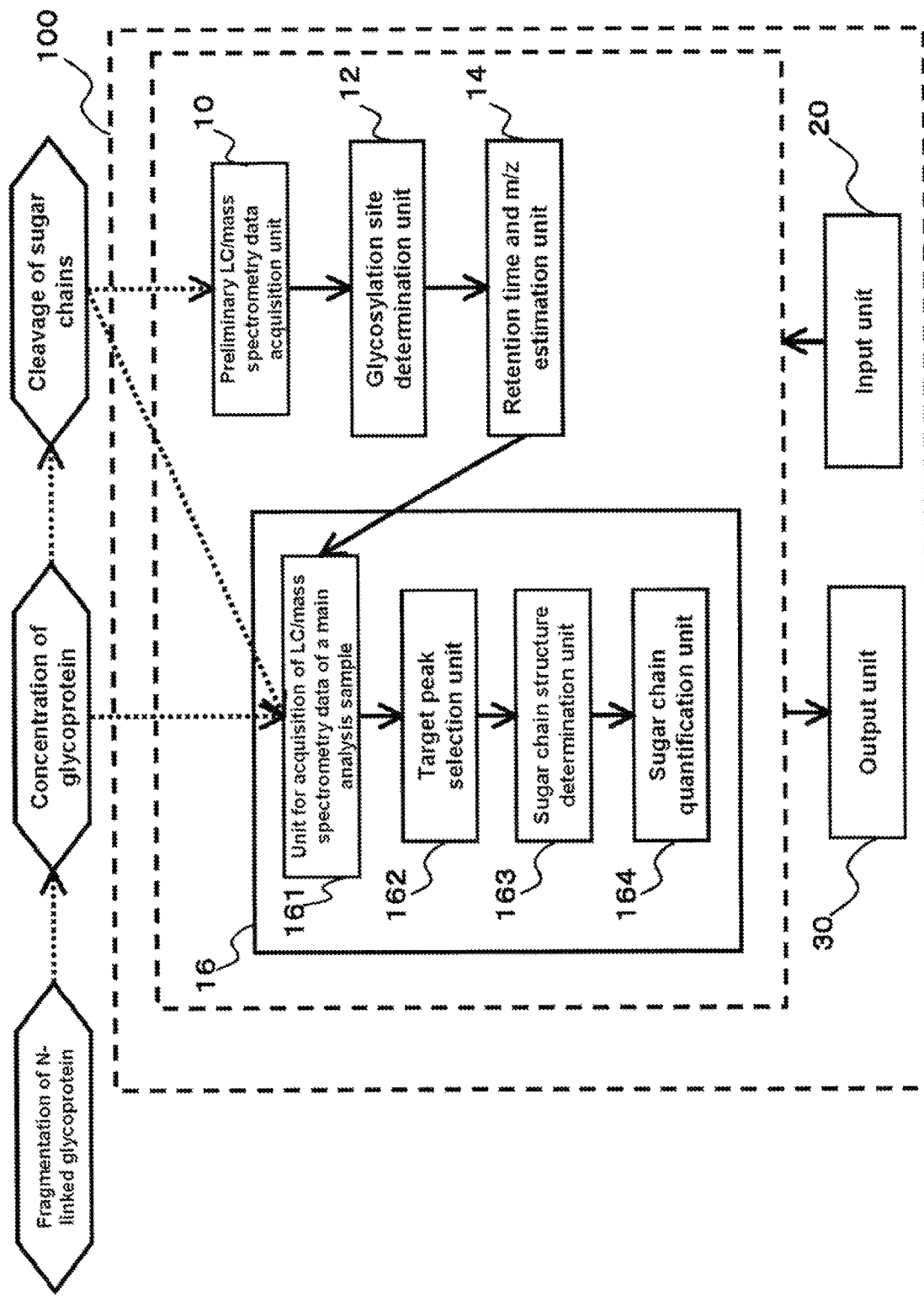
FIG. 3 is a block diagram illustrating an example of a configuration of the system for quantitative analysis of N-linked sugar chains according to the second embodiment of the present invention.
Figure 4:
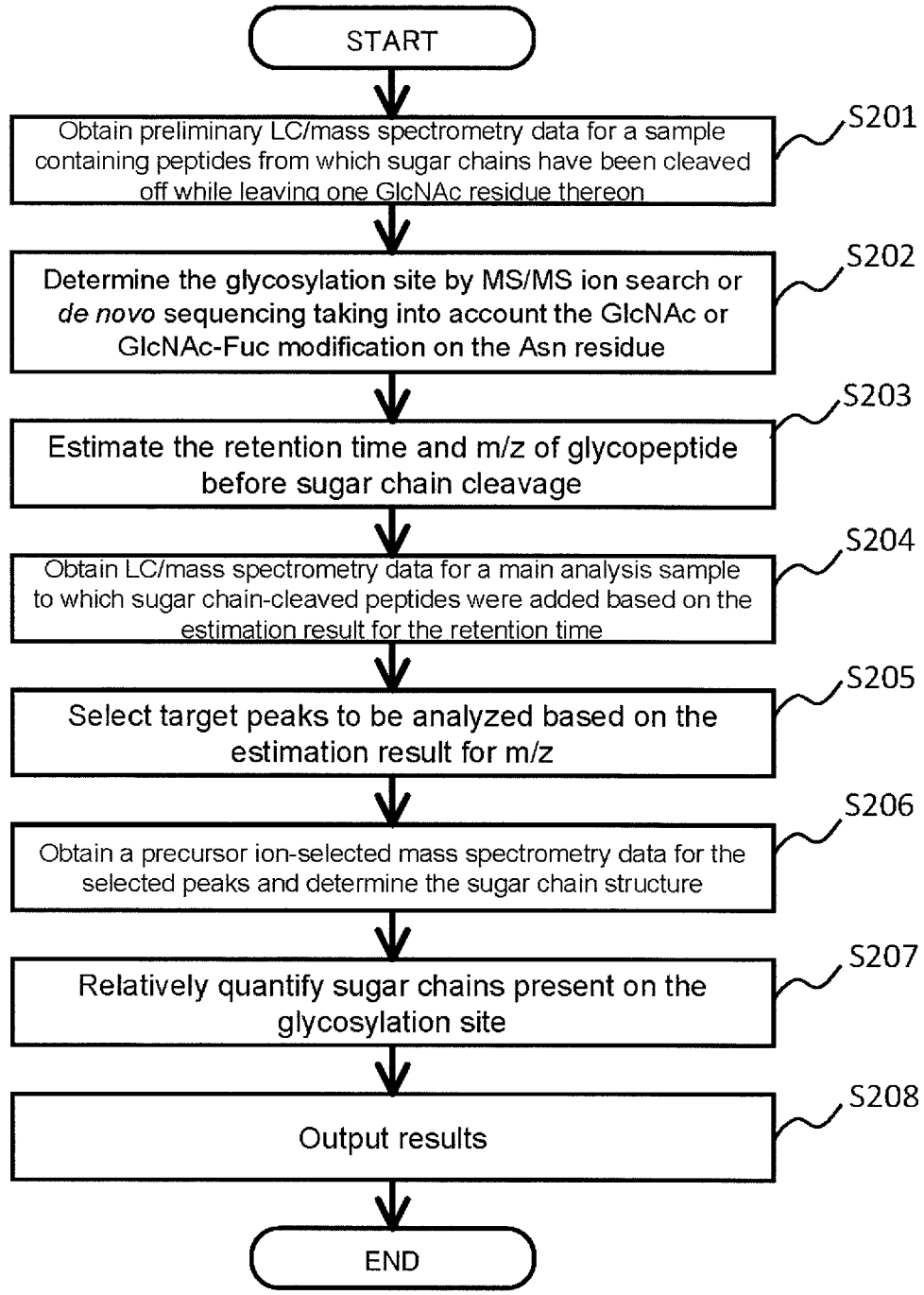
FIG. 4 is a flow chart illustrating one example of a process performed by the system for quantitative analysis of N-linked sugar chains according to the second embodiment of the present invention.
Figure 5:
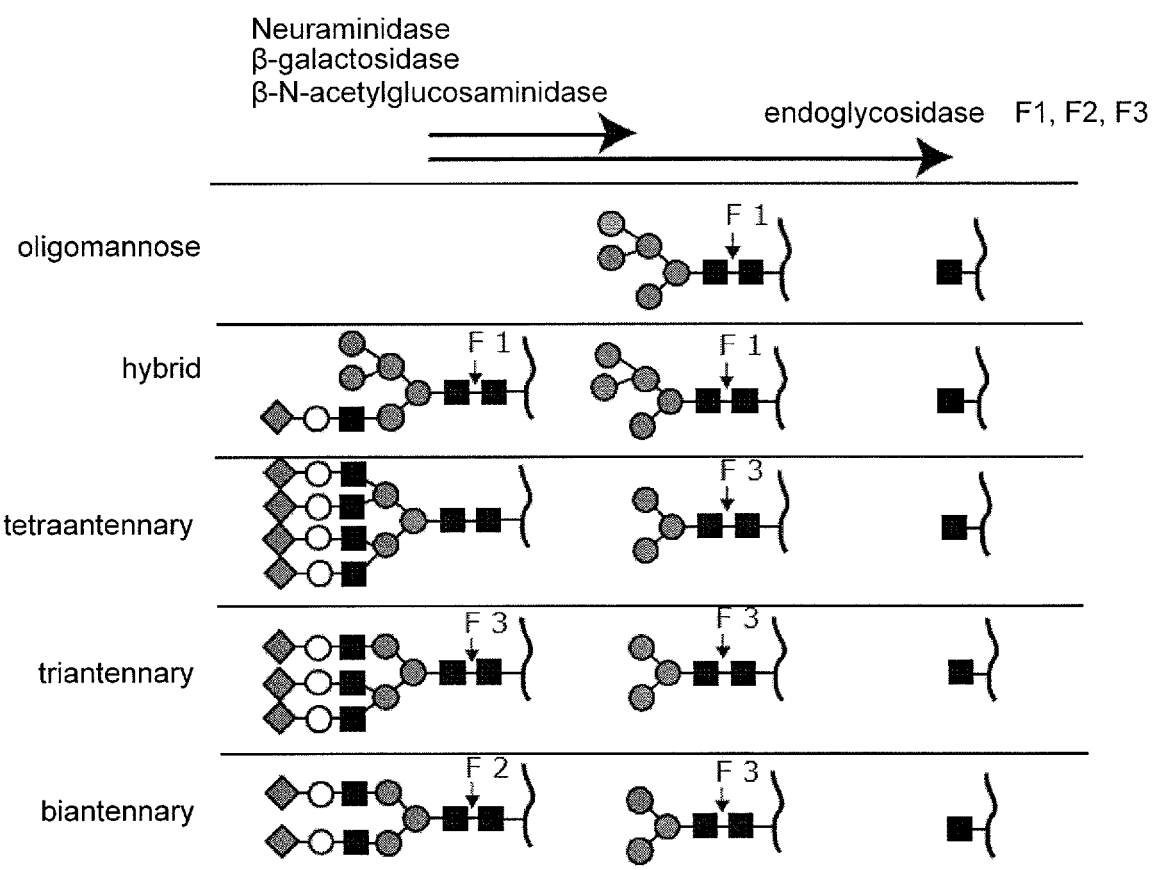
FIG. 5 illustrates actions of endo-β-N-acetylglucosaminidases used for cleaving sugar chains from glycopeptides while leaving GlcNAc on the Asn residue, and other glycosidases.

The system for analyzing N-linked sugar chain(s) according to the present invention will be described with reference to the drawings. FIGS. 1 and 2 illustrate the system for analyzing N-linked sugar chain(s) according to the first embodiment. FIGS. 3 and 4 illustrate the system for analyzing N-linked sugar chain(s) according to the second embodiment. Configurations that are common between FIGS. 1 and 3 are given the same numerical symbols.

The system 100 for analyzing N-linked sugar chain(s) according to the first embodiment shown in FIG. 1 is an apparatus for performing the method of analyzing N-linked sugar chain(s) according to the first embodiment of the present invention described above, and comprises a preliminary liquid chromatography/mass spectrometry data acquisition unit 10, a glycosylation site determination unit 12, a retention time and m/z estimation unit 14, a main analysis unit 16, an input unit 20, and an output unit 30. The main analysis unit 16 comprises a unit 161 for acquisition of liquid chromatography/mass spectrometry data of the main analysis sample, a target peak selection unit 162, and a sugar chain structure determination unit 163. The broken arrows indicate the flow of the sample and the solid arrows indicate the flow of the electrical signal.

The input unit 20 is a means for inputting information involved in the operation of the sugar chain analysis system 100. Conventionally known input means such as a keyboard can be preferably used. The output unit 30 outputs analysis results to a display device such as a monitor. The output unit 30 can output results from glycosylation site determination and sugar chain structure determination, as well as results of steps processed by the apparatus.

The preliminary liquid chromatography/mass spectrometry data acquisition unit 10 obtains chromatogram, mass spectrum, and product ion spectrum from a sugar chain-cleaved peptide sample prepared from a glycopeptide-containing sample which contains fragmented glycoprotein having N-linked sugar chain(s) by cleaving off the sugar chain(s) while leaving one GlcNAc residue (optionally, one Fuc residue is bound to said GlcNAc) on the Asn residue of the peptide by reaction with an endo-β-N-acetylglucosaminidase(s). Details on the preliminary liquid chromatography/mass spectrometry analysis are as explained hereinabove for the preliminary liquid chromatography/mass spectrometry step in the analysis method of the present invention.

The sugar chain-cleaved peptide sample to be subjected to preliminary liquid chromatography/mass spectrometry is prepared by the glycoprotein fragmentation step and the sugar chain cleavage step in the above-described analysis method of the present invention. Although a step of concentrating glycopeptides is also shown in FIG. 1, concentration of glycopeptides may optionally be carried out as explained hereinabove for the glycoprotein fragmentation step.

A sugar chain-cleaved peptide sample prepared outside the sugar chain analysis system 100 may be input to a liquid chromatography/mass spectrometry machine by a system user. Or, the system 100 may be configured to also perform the glycoprotein fragmentation step and sugar chain cleavage step.

In the latter case, the sugar chain analysis system 100 further comprises a glycoprotein fragmentation unit and a sugar chain cleavage unit, and optionally a glycopeptide concentration unit. A glycoprotein sample is added to a sample input port of the glycoprotein fragmentation unit by the user. In the glycoprotein fragmentation unit, the glycoprotein sample is fragmented by treatment with enzymes such as trypsin and Asp-N, or by other known fragmentation method. The fragmented glycoprotein sample (glycopeptide-containing sample) optionally undergoes a glycopeptide concentration treatment by a glycopeptide concentration unit, and part of the sample is added to the sugar chain cleavage unit. A remainder (all or a part of the remainder may be used) is temporarily stocked as a sample for the main analysis. In the glycopeptide concentration unit, glycopeptides are separated, recovered, and concentrated by a conventional method such as hydrophilic interaction chromatography with cellulose. In the sugar chain cleavage unit, a sugar chain-cleaved peptide sample is prepared by treating the glycopeptide-containing sample with one or two or more endo-β-N-acetylglucosaminidases to cleave off the sugar chain(s) while leaving one GlcNAc residue (one Fuc residue may be bound to the GlcNAc) on the Asn residue of the peptide. This sugar chain-cleaved peptide sample is added into a liquid chromatography/mass spectrometry machine, and then chromatogram and mass spectrum data are obtained by the preliminary liquid chromatography/mass spectrometry data acquisition unit 10.

The glycosylation site determination unit 12 performs MS/MS ion search or de novo sequencing, taking into account the GlcNAc or GlcNAc-Fuc modification on the Asn residue, to determine a glycosylation site in the glycopeptide. Details on the glycosylation site determination are as explained hereinabove for the glycosylation site determination step in the analysis method of the present invention. When the original glycoprotein has N-linked sugar chains at a plurality of positions in the molecule, each glycosylation site is determined by performing MS/MS ion search or de novo sequencing for each of GlcNAc- or GlcNAc-Fuc-binding peptides having different peptide moieties.

The retention time and m/z estimation unit 14 estimates the retention time in liquid chromatography and the m/z of a precursor ion(s) of the glycopeptide before the sugar chain cleavage based on the results obtained from the preliminary liquid chromatography/mass spectrometry and the MS/MS ion search or de novo sequencing. Details on the estimation step are as explained hereinabove for the step of estimating the retention time and m/z in the analysis method of the present invention. When estimating the liquid chromatography retention time, the system user may input the Δt value via the input unit 20. When the original glycoprotein has N-linked sugar chains at a plurality of positions in the molecule, the liquid chromatography retention time and the m/z of a precursor ion(s) in the main analysis are estimated for each of GlcNAc- or GlcNAc-Fuc-binding peptides having different peptide sequences.

In the main analysis unit 16, the glycopeptide sample that does not undergo sugar chain cleavage with an endo-β-N-acetylglucosaminidase(s) is used as a main analysis sample to perform a main analysis. When the glycopeptide sample is prepared outside the sugar chain analysis system 100, the glycopeptide sample is put into an liquid chromatography/mass spectrometry machine by the system user after completion of the preliminary liquid chromatography/mass spectrometry. When the system is configured to also perform a sample preparation step such as glycoprotein fragmentation, a glycopeptide-containing sample without sugar chain cleavage (main analysis sample) which is temporarily stocked in the system is put into an liquid chromatography/mass spectrometry machine by the system after completion of the preliminary liquid chromatography/mass spectrometry.

First, the unit 161 for acquisition of liquid chromatography/mass spectrometry data of the main analysis sample obtains a chromatogram, and a mass spectrum of a fraction at the estimated retention time, from the main analysis sample. More specifically, the unit 161 for acquisition of liquid chromatography/mass spectrometry data of the main analysis sample first obtains liquid chromatogram, and then a fraction at the retention time that has been estimated by the retention time and m/z estimation unit 14 is subjected to mass spectrometry to obtain a mass spectrum of the fraction.

Next, the target peak selection unit 162 selects a precursor ion peak(s) to be analyzed from the obtained mass spectrum of the fraction based on the m/z estimation result.

Then, the sugar chain structure determination unit 163 performs precursor ion-selected mass spectrometry (product ion scan) for the selected target peak(s) to determine the sugar chain structure.

When the original glycoprotein has N-linked sugar chains at a plurality of positions, liquid chromatography/mass spectrometry and precursor ion-selected mass spectrometry are performed for each of glycopeptides having different peptide sequences present in the glycopeptide-containing sample for the main analysis, using the estimation results for the retention time and m/z, to determine the sugar chain structure on each of the glycopeptides.

The system 100 for analyzing N-linked sugar chain(s) according to the second embodiment shown in FIG. 3 is an apparatus for performing the method of analyzing N-linked sugar chain(s) according to the second embodiment of the present invention described above. The configuration of the system is basically the same as the system according to the first embodiment shown in FIG. 1, except that the main analysis unit 16 further comprises a sugar chain quantification unit 164.

In the system 100 according to the second embodiment, a sugar chain-cleaved sample is used for preliminary liquid chromatography/mass spectrometry, and also utilized as an internal standard in the main analysis. As explained for the analysis method according to the second embodiment, a sugar chain-cleaved peptide sample from which undeglycosylated glycopeptides are removed is preferably used as an internal standard.

Also in the second embodiment, the sugar chain analysis system 100 may be configured so that a sugar chain-cleaved peptide sample and an internal standard are prepared outside the system and then the system user puts the sugar chain-cleaved peptide sample into a liquid chromatography/mass spectrometry machine and adds the internal standard to a main analysis sample. Or, the system 100 may be configured to also perform the glycoprotein fragmentation, sugar chain cleavage, preparation of internal standard, and addition of the internal standard to a main analysis sample.

In the latter configuration, as in the system according to the first embodiment, the system 100 may comprise a glycoprotein fragmentation unit and a sugar chain cleavage unit, and optionally a glycopeptide concentration unit, as well as further optionally an internal standard preparation unit. In this case, the sample after undergoing the sugar chain cleavage in the sugar chain cleavage unit is partly subjected to preliminary liquid chromatography/mass spectrometry, and a remainder is provided to the internal standard preparation unit. In the internal standard preparation unit, a treatment for removing glycopeptides whose sugar chains are not cleaved off from the sugar chain-cleaved peptide sample is performed, for example, by a method of adding cold acetone to the sugar chain-cleaved peptide sample and precipitating glycopeptides whose sugar chains are not cleaved off to separate them, or by a method of adsorbing and removing the sugar chain-noncleaved glycopeptides using hydrophilic interaction chromatography. Or, the sugar chain cleavage unit may further carry out removal of sugar chain-noncleaved glycopeptides from the sugar chain-cleaved peptide sample, and then the sugar chain-cleaved peptide sample after the removal treatment may be partly subjected to preliminary liquid chromatography/mass spectrometry, and a remainder may be used as the internal standard.

Processes up until the process carried out by the sugar chain structure determination unit 163 are the same as in the system according to the first embodiment except that an internal standard is added to the main analysis sample.

In the sugar chain quantification unit 164, sugar chains present on the glycosylation site are relatively quantified by obtaining extracted ion chromatograms of the internal standard and each glycopeptide, and calculating the relative intensity of each glycopeptide relative to the internal standard. Details are as explained for the sugar chain quantification step in the analysis method according to the second embodiment of the present invention. A graph of the calculation results of the relative intensity are optionally created, and outputted from the output unit 30 to display the results on a display device.

The present invention also provides a program(s) for analyzing N-linked sugar chain(s) of glycoprotein, the program(s) causing one or more computers to function as: a preliminary liquid chromatography/mass spectrometry data acquisition unit; a glycosylation site determination unit; a retention time and m/z estimation unit; a main analysis unit comprising a unit for acquisition of liquid chromatography/mass spectrometry data of the main analysis sample, a target peak selection unit, and a sugar chain structure determination unit; and an output unit. The program(s) is/are for causing a computer(s) to function as the system according to the first embodiment.

The present invention further provides a program(s) for analyzing N-linked sugar chain(s) of glycoprotein, the program(s) causing one or more computers to function as: a preliminary liquid chromatography/mass spectrometry data acquisition unit; a glycosylation site determination unit; a retention time and m/z estimation unit; a main analysis unit comprising a unit for acquisition of liquid chromatography/mass spectrometry data of the main analysis sample (a sugar chain-cleaved peptide sample is added to the main analysis sample as an internal standard), a target peak selection unit, a sugar chain structure determination unit, and a sugar chain quantification unit; and an output unit. The program(s) is/are for causing a computer(s) to function as the system according to the second embodiment.

The present invention also provides an internal standard peptide for use in quantitative analysis of a glycopeptide contained in a tryptic digest of an IgG antibody. The internal standard peptide is composed of a peptide consisting of the amino acid sequence of EEQYNSTYR (SEQ ID NO: 1), EEQFNSTFR (SEQ ID NO: 2), EEQYNSTFR (SEQ ID NO: 3) or EEQFNSTYR (SEQ ID NO: 4), wherein one GlcNAc residue, or one GlcNAc residue with one Fuc residue bound thereto, is bound to the asparagine residue of the peptide. One having the peptide sequence of EEQYNSTYR (SEQ ID NO: 1) can be used as an internal standard for quantitative analysis of IgG1 antibody glycopeptides. One having the peptide sequence of EEQFNSTFR (SEQ ID NO: 2) can be used as an internal standard for quantitative analysis of IgG2 antibody glycopeptides. One having the peptide sequence of EEQYNSTFR (SEQ ID NO: 3) can be used as an internal standard for quantitative analysis of IgG3 antibody glycopeptides. One having the peptide sequence of EEQFNSTYR (SEQ ID NO: 4) can be used as an internal standard for quantitative analysis of IgG4 antibody glycopeptides. The internal standard peptides can be used for sugar chain analysis of various IgG antibodies, preferably various human IgG antibodies. The term "human IgG antibody" includes not only IgG antibodies isolated from human and IgG antibodies produced using human cell lines, but also IgG antibodies produced using non-human animals genetically engineered to produce a human antibody.

An internal standard for use in mass spectrometry for quantitative analysis of sugar chains of an IgG antibody can be produce by fragmenting an IgG antibody to obtain a peptide mixture, separating and recovering glycopeptides from the peptide mixture, allowing the glycopeptides to react with an endo-β-N-acetylglucosaminidase(s), and then removing glycopeptides whose sugar chains are not cleaved off. When trypsin is used for the fragmentation of an IgG antibody, the obtained internal standard peptide becomes an internal standard for quantitative analysis of N-linked sugar chain(s) in a glycopeptide sample prepared from a tryptic digest of an IgG antibody. When another enzyme, for example Asp-N, is used for the fragmentation of an IgG antibody, the obtained internal standard peptide becomes an internal standard for quantitative analysis of N-linked sugar chain(s) in a glycopeptide sample prepared from an Asp-N digest of an IgG antibody. The method of removing sugar chain-noncleaved glycopeptides is as described above. As also described above, internal standard peptides are required to be prepared using the same subtypes of IgG antibodies as the IgG antibody to be analyzed.

EXAMPLES

The present invention will now be described in detail with reference to Examples. However, the present invention is not limited to the following Examples.

Example 1 (First Embodiment)

(1) Preparation of Test Sample

A certain IgG1 antibody (certain mAb) therapeutic candidate, which was an N-linked glycoprotein, was used as a glycoprotein sample. First, 100 μg of the glycoprotein sample was dissolved in 100 μg of 50 mM tris(hydroxymethyl)aminomethane and 2 M urea, pH 8.0. Then, 1 μg of 1 M dithiothreitol was added and left to stand at room temperature for 1 hour to reduce the glycoprotein. Thereafter, 2.8 μg of 1 M iodoacetic acid was added and the mixture was left to stand in the dark for 1 hour for alkylation. The alkylation was then stopped by addition of 1 μg of 1 M dithiothreitol.

(2) Protein Fragmentation

To the alkylated sample, 100 μL of water and then 2 μg of trypsin were added, and the mixture was incubated for 16 hours at 37° C. to digest and fragment the glycoprotein. Next, this tryptic digest was subjected to hydrophilic interaction chromatography with cellulose, thereby separating and recovering glycopeptides from the tryptic digest and concentrating the glycopeptides, to obtain a glycopeptide sample.

(3) Cleavage of Sugar Chains

Half of the glycopeptide sample was subjected to sugar chain cleavage, and the remaining half was used as a main analysis sample. The half volume of the glycopeptide sample was treated with 0.001 unit of Endo F2 and 0.001 unit of Endo F3 for 16 hours at 37° C. to cleave off each sugar chain while leaving the reducing terminal GlcNAc on the peptide.

(4) Preliminary LC/MS/MS and MS/MS Ion Search

The sample after the sugar chain cleavage was subjected to LC/MS/MS, to carry out MS/MS ion search taking into account the Asn-GlcNAc modification.

<Instruments Used and Analysis Conditions>

1. The sample obtained by cleaving off sugar chains while leaving the reducing terminal GlcNAc on peptides was dried, and then dissolved in 25 μL of 0.1% formic acid aqueous solution.

2. A nano liquid chromatograph (EASY-nLC 1000; Thermo Scientific) equipped with a trap column (PepMap100 C18 3 μm, diameter 75 μm×length 20 mm; Thermo Scientific, MA, USA) and an analytical column (Nano HPLC capillary column; Nikkyo Technos, Tokyo, Japan) was connected to a hybrid quadrupole Orbitrap mass spectrometer (Q Exactive; Thermo Scientific). To the trap column, 5 μL of the dissolved sample was injected. After desalting, the sample was separated in the analytical column. The sample separation was carried out using 0.1% formic acid aqueous solution as Solvent A and 0.1% formic acid-acetonitrile as Solvent B, with a linear gradient from 0% Solvent B to 35% Solvent B over 0 min to 40 min, and a linear gradient from 35% Solvent B to 100% Solvent B over 40 min to 45 min. The positive ion mode (applied voltage 2,000 V) was used throughout the measurement.

Figure 6A:
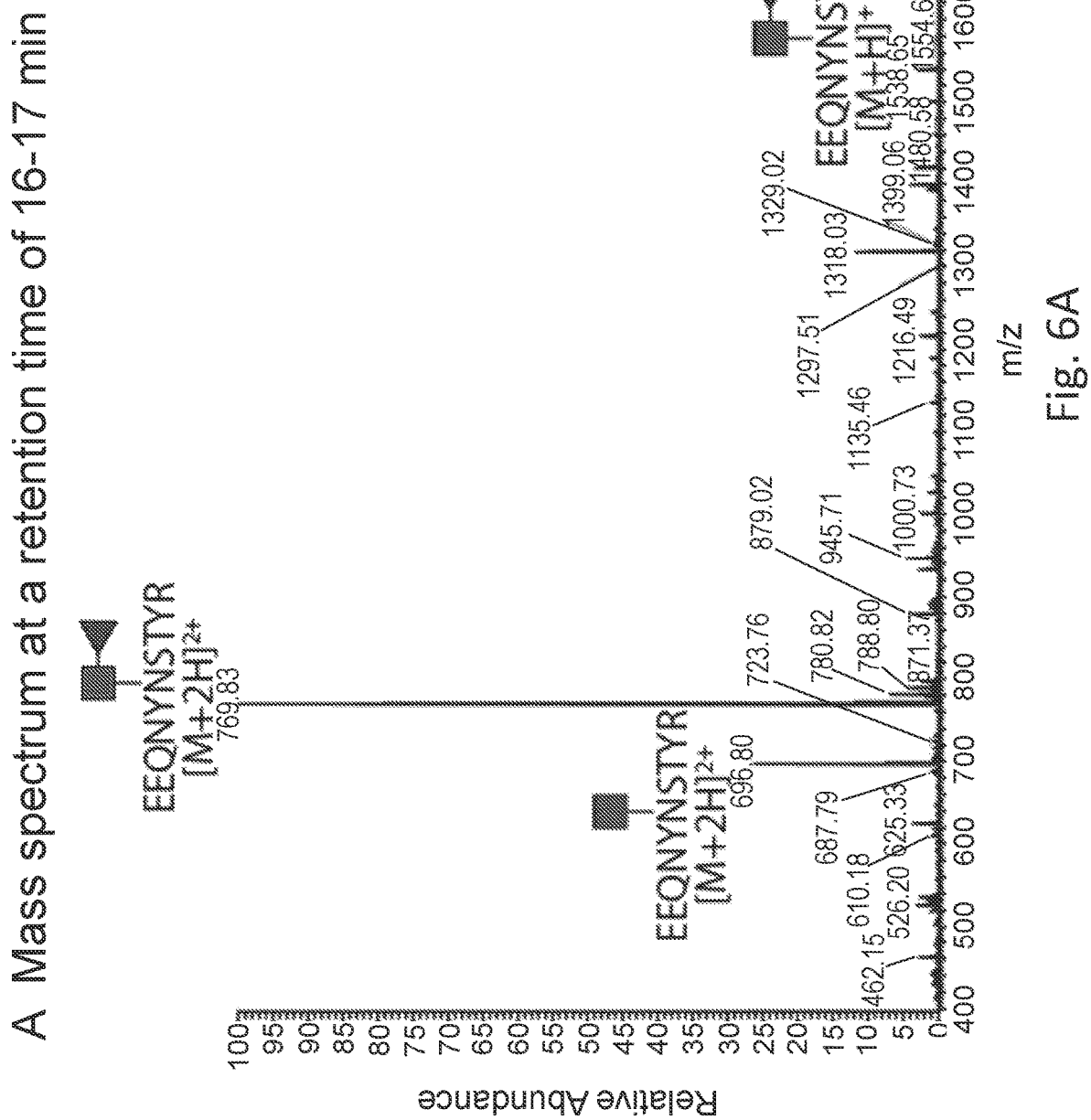
FIGS. 6A, 6B, and 6C show a mass spectrum and extracted ion chromatograms of the peptides whose sugar chains were cleaved off while leaving GlcNAc or GlcNAc-Fuc thereon, prepared from glycopeptides derived from a certain IgG1 antibody drug candidate (certain mAb).
Figure 6B:
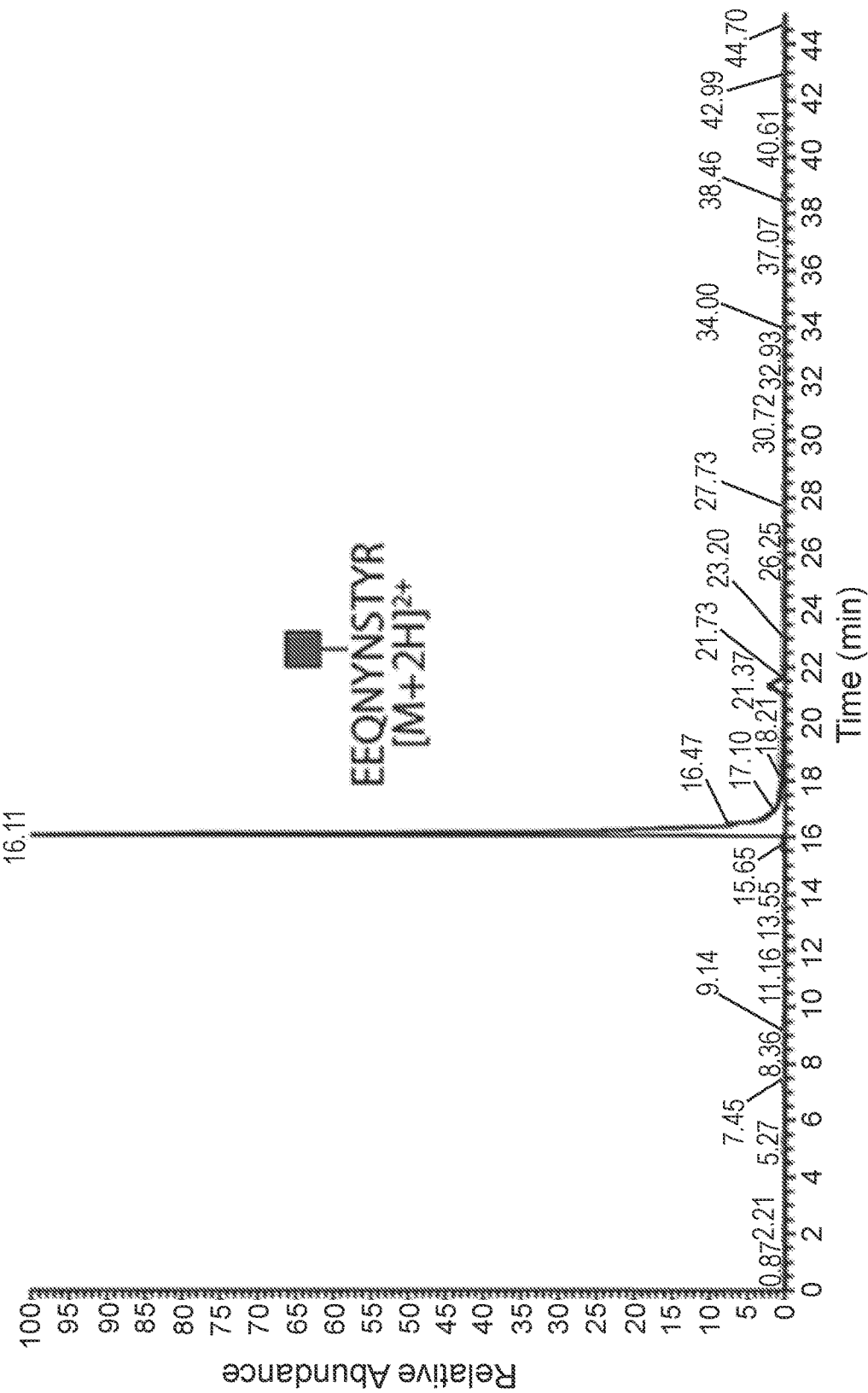
Figure 6C:
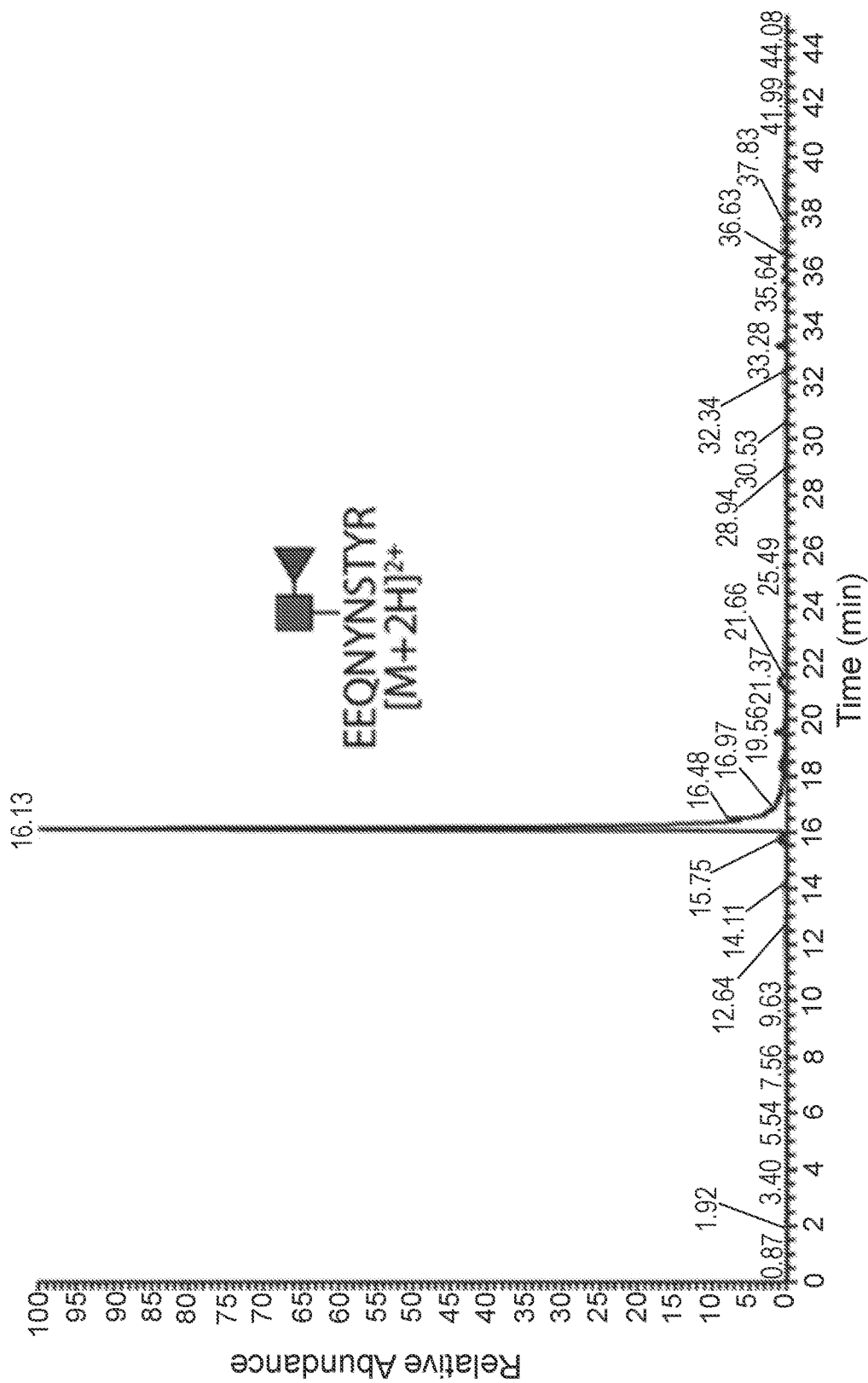

As a result, a peptide composed of the peptide sequence of EEQYNSTYR (SEQ ID NO: 1) in which the Asn is modified with GlcNAc or GlcNAc+Fuc was determined. It was revealed that the chromatography retention time ($Rt_{Peptide+GlcNAc}$) of this peptide was 16.1 min, and that the monoisotopic mass $[M+H]^+$ of this peptide was 1189.51+203.0794=1392.5894 (in the case of GlcNAc modification) or 1189.51+203.0794+146.0579=1538.6473 (in the case of GlcNAc+Fuc modification) (FIG. 6).

(5) Estimation of the Retention Time and m/z of Glycopeptides in the Main Analysis The retention time and the mass-to-charge ratios (m/z) of the glycopeptides when the remainder of the glycopeptide sample was subjected to the main analysis were estimated.

The retention time was estimated using the Formula 1 described above, with Δt set to 2 min. As a result, the retention time of the glycopeptides in the main analysis were estimated at 14.1 min to 18.1 min.

Estimates of the m/z of the glycopeptides were calculated using a method in which monoisotopic masses of sugar chains that could be attached to proteins in the form of N-linked sugar chain were comprehensively considered from a sugar chain database Glycome DB (http://glycome-db.org). Estimation results were as follows: $[M+2H]^{2+}$: 1041.418, 1114.446, ..., 1317.526, 1398.552, ...; $[M+3H]^{3+}$: 694.614, 743.300, ..., 878.687, 932.704, ....

(6) Main Analysis of Glycopeptide Sample

The remaining half of the glycopeptide sample in which sugar chains were not cleaved off was subjected to LC/MS/MS.

<Instruments Used and Analysis Conditions>

1. The sample obtained by cleaving off sugar chains while leaving the reducing terminal GlcNAc on peptides was dried, and then dissolved in 25 μL of 0.1% formic acid aqueous solution.

2. A nano liquid chromatograph (EASY-nLC 1000; Thermo Scientific) equipped with a trap column (PepMap100 C18 3 μm, diameter 75 μm×length 20 mm; Thermo Scientific, MA, USA) and an analytical column (Nano HPLC capillary column; Nikkyo Technos, Tokyo, Japan) was connected to a hybrid quadrupole Orbitrap mass spectrometer (Q Exactive; Thermo Scientific). To the trap column, 5 μL of the dissolved sample was injected. After desalting, the sample was separated in the analytical column. The sample separation was carried out using 0.1% formic acid aqueous solution as Solvent A and 0.1% formic acid-acetonitrile as Solvent B, with a linear gradient from 0% Solvent B to 35% Solvent B over 0 min to 40 min, and a linear gradient from 35% Solvent B to 100% Solvent B over 40 min to 45 min. The positive ion mode (applied voltage 2,000 V) was used throughout the measurement.

Figure 7A:
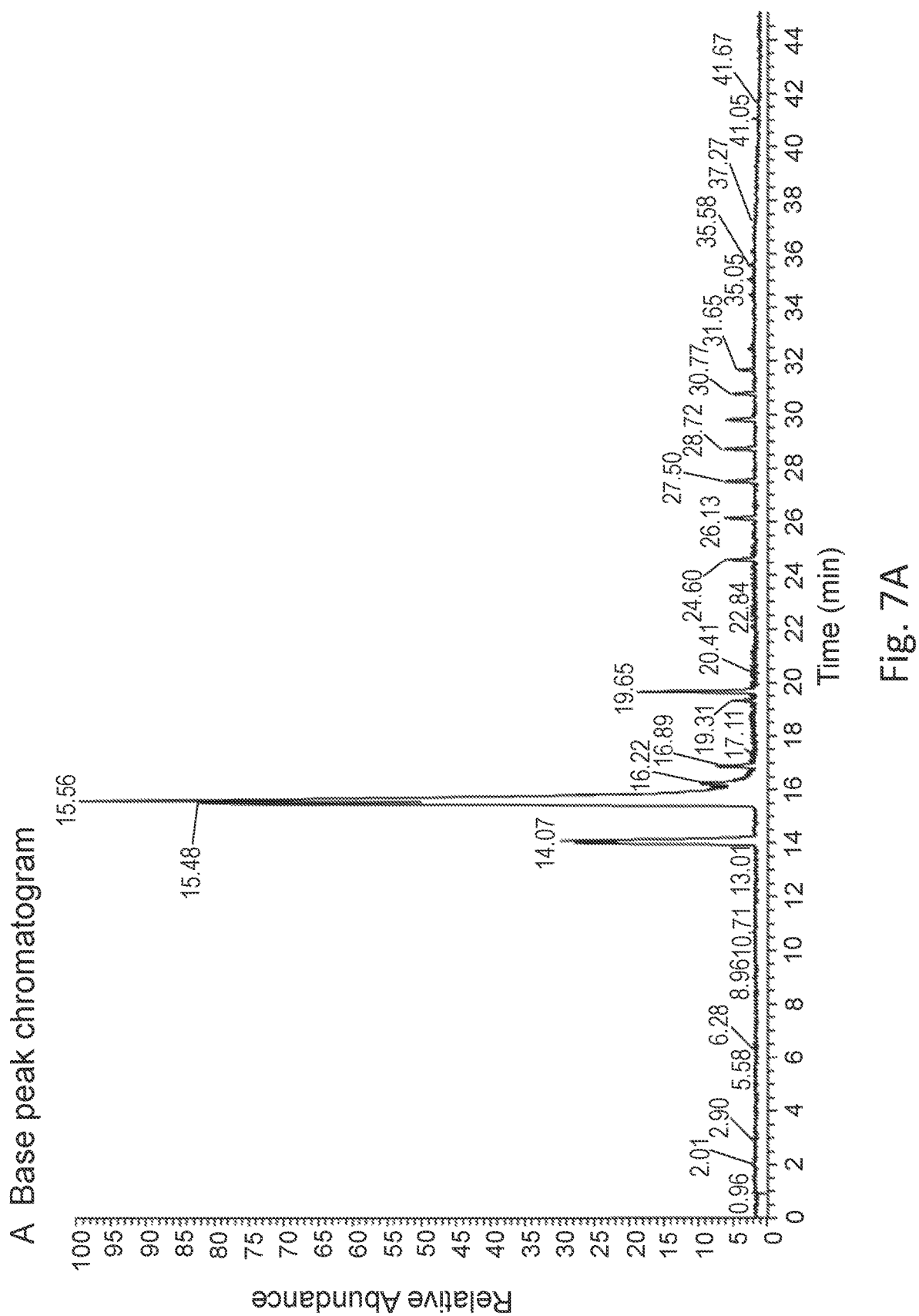
FIGS. 7A and 7B show a base peak chromatogram and a main peak-integrated mass spectrum observed from 15 to 17 min of the glycopeptides derived from a certain mAb (main analysis sample). It is apparent that the glycopeptides were eluted at retention times very close to the retention times shown in FIGS. 6A-6C.
Figure 7B:
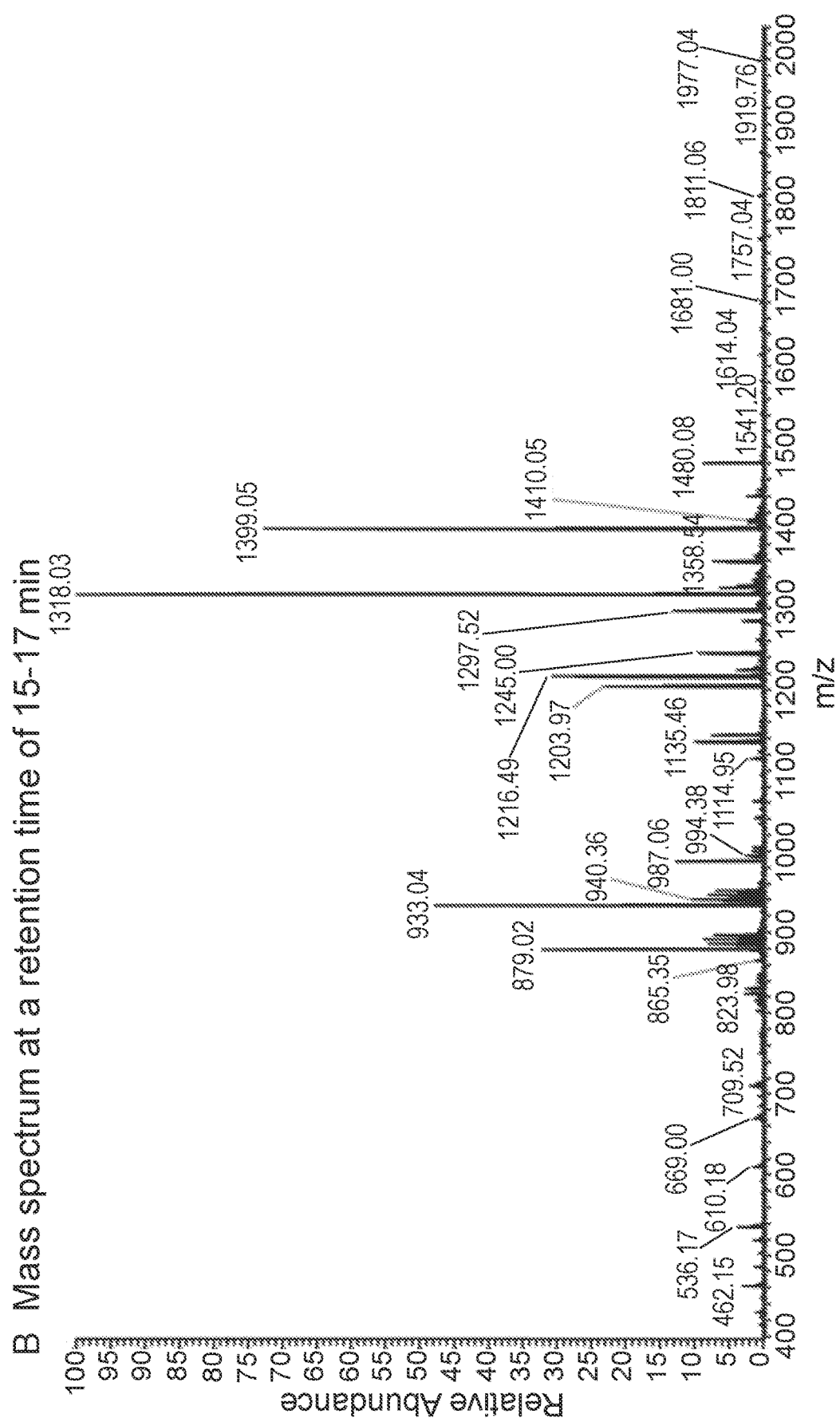

FIG. 7A shows the base peak chromatogram of the glycopeptide sample. As estimated preliminarily, a base peak appeared at the retention time from 15 to 17 min, and thus this fraction was subjected to mass spectrometry. As a result, as shown in FIG. 7B, glycopeptide peaks such as m/z 1317.526, 1398.552, 878.687, and 932.704 were observed as estimated by the preliminary prediction of m/z. These peaks are subjected to analysis by precursor ion-selected product ion scan, so that the glycopeptide structure of interest can be effectively determined. Known scoring algorithms such as Sequest, MASCOT, and X!Tandem may be used to determine the structure of the glycopeptide.

Figure 8:
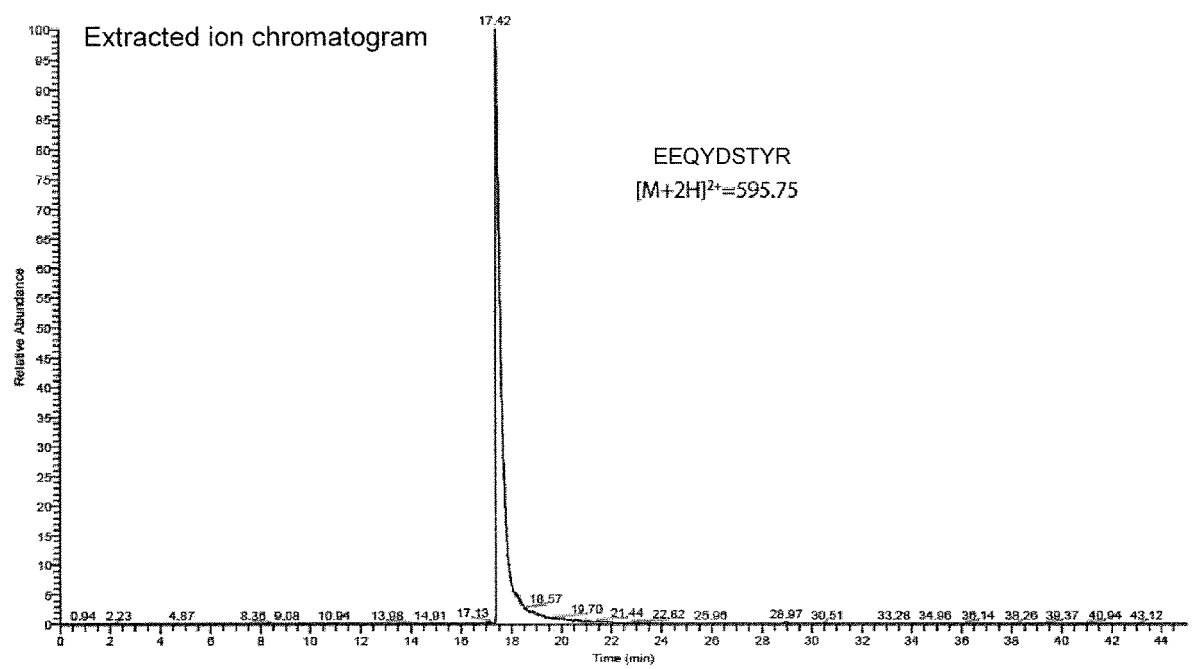
FIG. 8 shows an extracted ion chromatogram of a sample prepared by subjecting the glycopeptides derived from a certain mAb to cleavage by a conventional PNGase F treatment. It is apparent that there is a large difference in elution time from that of the main analysis sample. It is apparent that the sample prepared by conventional treatment was eluted at a position distant from the elution time of the glycopeptide shown in FIGS. 7A-7B, as compared with the peptides whose sugar chains were cleaved off while leaving GlcNAc thereon shown in FIGS. 6A-6C.

FIG. 8 shows an extracted ion chromatogram obtained by a conventional method, i.e., by cleaving off sugar chains from the glycopeptide sample obtained in (2) with PNGase F treatment to convert Asn into Asp (the peptide sequence was changed from EEQYNSTYR to EEQYDSTYR), and then subjecting the resultant to LC/MS/MS. When compared with the elution time of the peptide sample in which sugar chains were cleaved off while leaving a GlcNAc on the peptide (FIG. 6) and the elution time of the glycopeptide sample without sugar chain cleavage (FIG. 7), the PNGase F-treated sample was eluted at a distant position. Since the conventional method using PNGase F treatment increases the difference in the retention time due to the conversion from Asn to Asp as demonstrated herein, it can be seen that there is great significance in using peptides whose sugar chains are cleaved off while leaving a GlcNAc thereon.

Example 2 (Second Embodiment)

(1) Preparation of Test Samples

A certain mAb and human myeloma-derived IgG1 antibody, which were N-linked glycoproteins, were used as glycoprotein samples. First, 100 μg of each of the samples was dissolved in 100 μg of 50 mM tris(hydroxymethyl)aminomethane and 2 M urea, pH 8.0. Then, 1 μg of 1 M dithiothreitol was added and left to stand at room temperature for 1 hour to reduce the glycoprotein. Thereafter, 2.8 μg of 1 M iodoacetic acid was added and the mixtures were left to stand in the dark for 1 hour for alkylation. The alkylation was then stopped by addition of 1 μg of 1 M dithiothreitol.

(2) Digestion of Proteins

To the alkylated samples, 100 μL of water and then 2 μg of trypsin were added, and the mixtures were incubated for 16 hours at 37° C. to digest and fragment the glycoprotein, thereby obtaining peptide samples containing glycopeptides.

(3) Cleavage of Sugar Chains (Preparation of Internal Standards)

Half of the peptide sample derived from human myeloma-derived IgG1 was subjected to hydrophilic interaction chromatography with cellulose, thereby separating and recovering glycopeptides from the peptide sample, to obtain a glycopeptide sample derived from human myeloma-derived IgG1. The glycopeptide sample was treated with 0.001 unit of Endo F2 and 0.001 unit of Endo F3 for 16 hours at 37° C. to cleave off each sugar chain while leaving the reducing terminal GlcNAc on the peptide.

In order to remove unreacted glycopeptides from sugar chain-cleaved peptides, hydrophilic interaction chromatography with cellulose was used for the removal of the unreacted glycopeptides. This sample was used not only as a sample for preliminary LC/MS/MS for estimating the elution time and m/z of a target glycopeptide in the main analysis, but also as an internal standard in the main analysis. Since the certain mAb was also an IgG1 antibody and had the same peptide sequence around a glycosylation site as human myeloma-derived IgG1, this sample was also used as an internal standard in the main analysis of the certain mAb.

(4) Preliminary LC/MS/MS Analysis

In order to estimate the elution time and m/z of a target glycopeptide in the main analysis, the above-described sugar chain-cleaved sample (internal standard substance) prepared from a human myeloma-derived IgG1 sample was subjected to LC/MS/MS. Conditions of LC/MS/MS were the same as in Example 1. Since the peptide sequence and the glycosylation site had been already identified in the above-described Example 1, the step of MS/MS ion search taking into account the Asn-GlcNAc modification was omitted.

Figure 9B:
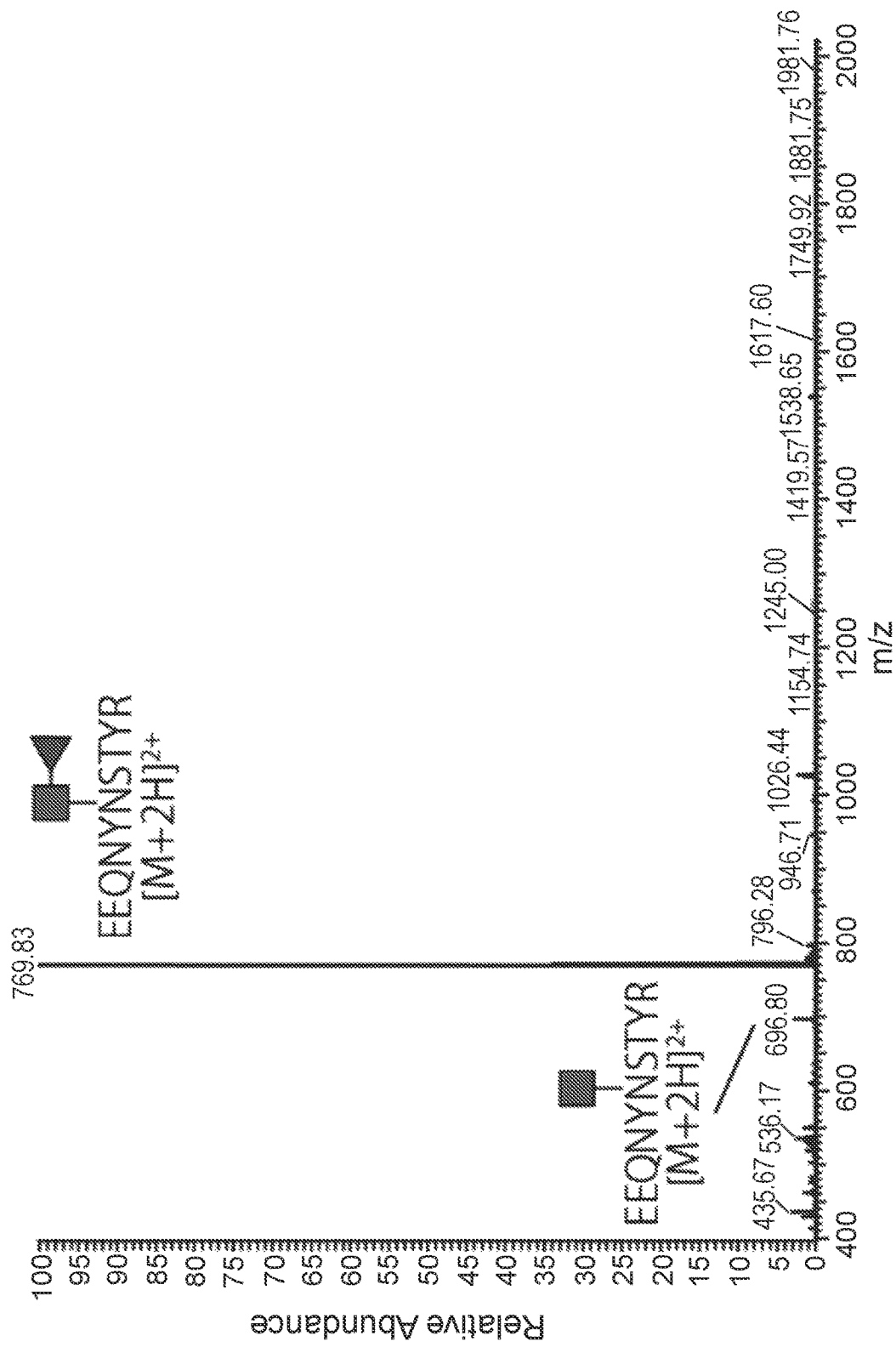

FIG. 9 shows the base peak chromatogram and mass spectrum of the internal standard substance. It can be seen that sugar chains are cleave off, with a GlcNAc or GlcNAc+Fuc left on peptides, and that the internal standard does not contain undeglycosylated impurity. The chromatography retention time ($Rt_{Peptide+GlcNAc}$) of the internal standard substance was 10.52 min (FIG. 9A). The m/z ($[M+2H]^{2+}$) were 769.83 for the peptide with GlcNAc+Fuc modification, and 696.80 for the peptide with GlcNAc modification (FIG. 9B).

(5) Estimation of the Retention Time and m/z of Glycopeptides in the Main Analysis The retention time and the mass-to-charge ratios (m/z) of the glycopeptides when samples containing a tryptic digest of certain mAb or human myeloma-derived IgG1 (peptide samples) were subjected to the main analysis were estimated.

The retention time was estimated using the Formula 1 described above, with Δt set to 0.5 min. As a result, retention time of the glycopeptides in the main analysis was estimated at 10.02 min to 11.02 min.

Estimates of the m/z of the glycopeptides were calculated based on the results of [M+2H]$^{2+}$ shown in FIG. 9B, using a method in which monoisotopic masses of sugar chains that could be attached to proteins in the form of N-linked sugar chain were comprehensively considered from a sugar chain database Glycome DB (http://glycome-db.org). Estimation results were as follows: [M+2H]$^{2+}$: 1203.97, 1245.00, 1318.03, . . . , 1399.05, . . . , 1480.08, . . . , [M+3H]$^{3+}$: . . . , 879.02, . . . , 933.04, . . . .

(6) Main Analysis of Tryptic Digest Samples
(6-1) Determination of Structures of Sugar Chains A certain amount of internal standard was added to the samples containing a tryptic digest of certain mAb or human myeloma-derived IgG1, and the mixtures were subjected to LC/MS/MS. The main analysis was carried out with the concentration of glycopeptides in the tryptic digest sample omitted in this Example 2, but may be carried out using a sample containing concentrated glycopeptides as in Example 1.

<Instruments Used and Analysis Conditions>
1. Five micrograms of internal standard in which sugar chains were cleaved off while leaving the reducing terminal GlcNAc on the peptides was added to 50 µg of each sample containing a tryptic digest of certain mAb or human myeloma-derived IgG1 and the total volume of each sample was adjusted to 50 µL.
2. A nano liquid chromatograph (EASY-nLC 1000; Thermo Scientific) equipped with a trap column (PepMap100 C18 3 µm, diameter 75 µm×length 20 mm; Thermo Scientific, MA, USA) and an analytical column (Nano HPLC capillary column; Nikkyo Technos, Tokyo, Japan) was connected to a hybrid quadrupole Orbitrap mass spectrometer (Q Exactive; Thermo Scientific). To the trap column, 1 µL of the sample to which the internal standard was added was injected. After desalting, the sample was separated in the analytical column. The sample separation was carried out using 0.1% formic acid aqueous solution as Solvent A and 0.1% formic acid-acetonitrile as Solvent B, with a linear gradient from 0% Solvent B to 35% Solvent B over 0 min to 10 min, and a linear gradient from 35% Solvent B to 100% Solvent B over 10 min to 12 min. The positive ion mode (applied voltage 2,000 V) was used throughout the measurement.

Figure 10A:
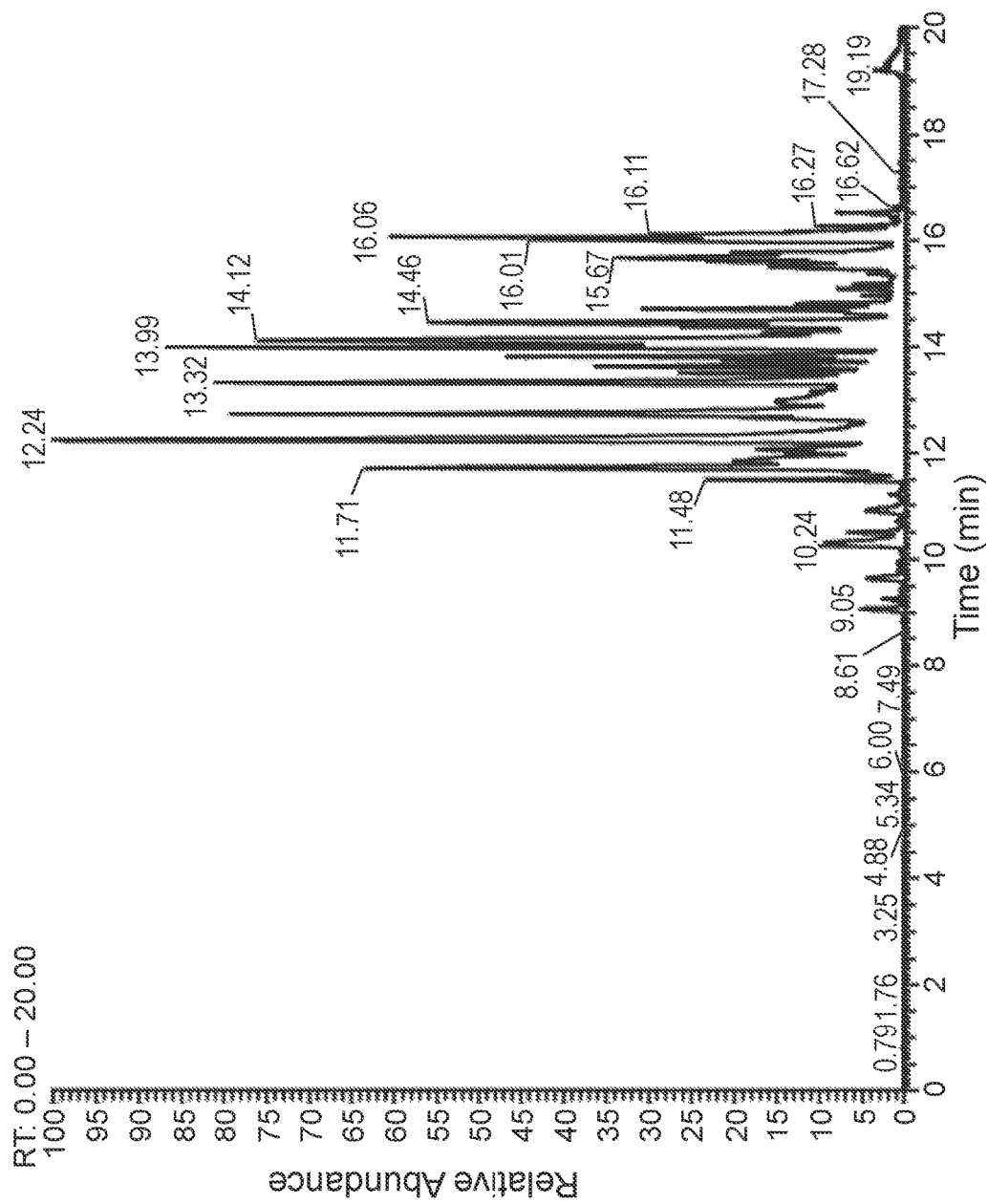
FIGS. 10A and 10B show the base peak chromatogram obtained from liquid chromatography/mass spectrometry of tryptic digests of a certain mAb and a human myeloma-derived IgG1 to each of which an internal standard was added.
Figure 10B:
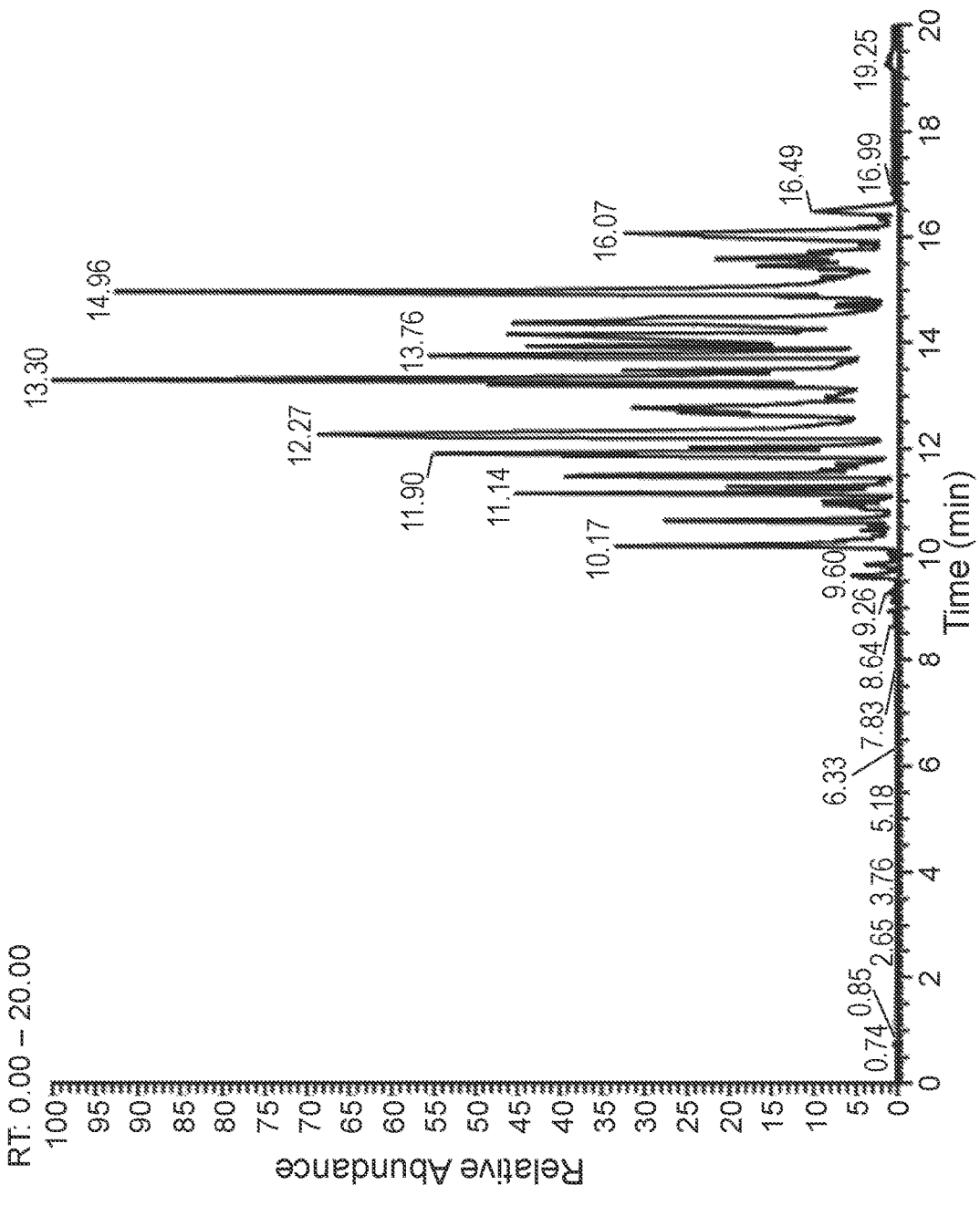

FIGS. 10A and 10B show the base peak chromatograms of two tryptic digest samples. Based on the estimation result for the retention time, a fraction at the retention time from 10 to 11 min was subjected to mass spectrometry.

Figure 11:
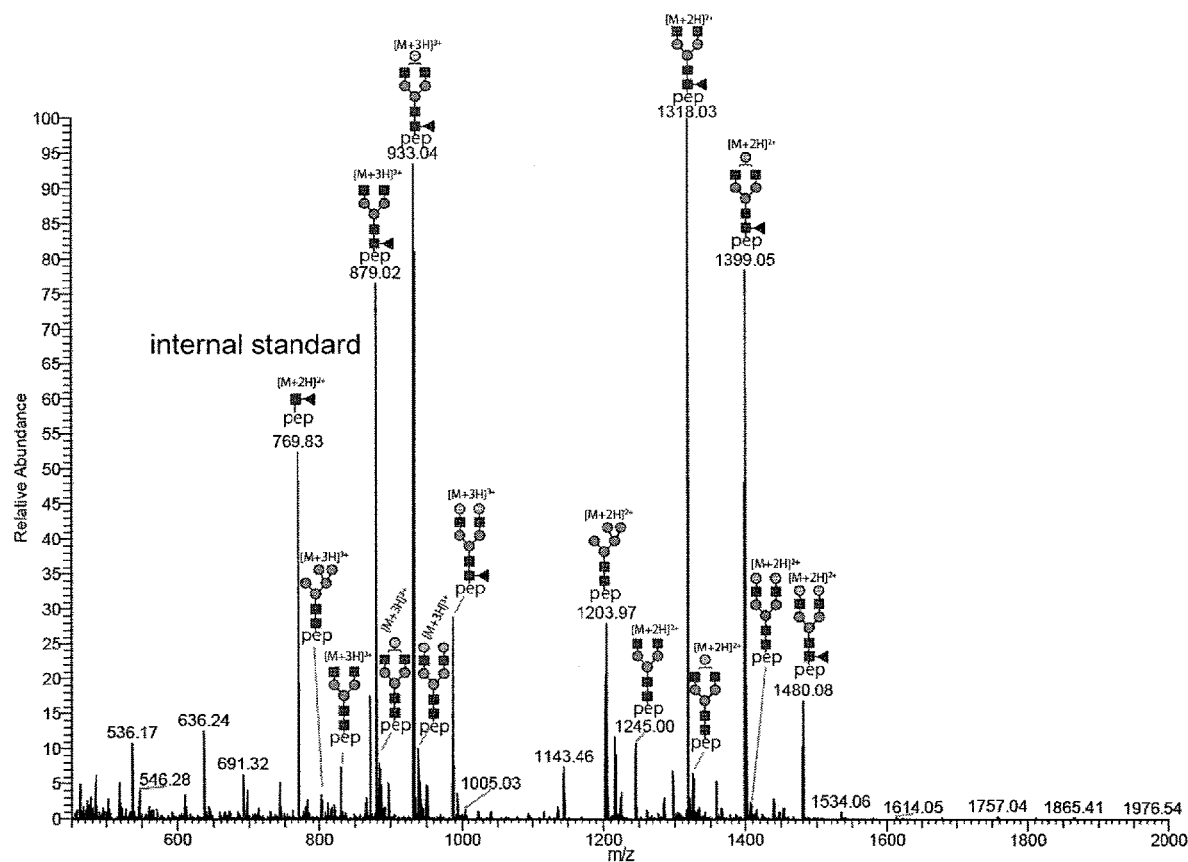
FIG. 11 shows a mass spectrum of a sample containing a tryptic digest of a certain mAb and an internal standard added thereto, at the retention time from 10 min to 11 min. Peaks of the internal standard substance and glycopeptides derived from the certain mAb can be observed.

FIG. 11 shows a mass spectrum of a sample containing a tryptic digest of a certain mAb (FIG. 10A) at the retention time from 10 min to 11 min. As estimated by the preliminary prediction of m/z, glycopeptide peaks such as m/z 879.02, 933.04, 1203.97, 1245.00, 1318.03, 1399.05, and 1480.08 were observed. These glycopeptide peaks were subjected to analysis by precursor ion-selected product ion scan, so that the structure of each glycopeptide was determined as shown in FIG. 11 (pep=EEQYNSTYR; each sugar chain was bound to the N). Similarly, for the human myeloma-derived IgG1, a mass spectrum at the retention time from 10 to 11 min was obtained, and then each glycopeptide peak was subjected to analysis by precursor ion-selected product ion scan, to determine the structures of the glycopeptides (figure omitted).

(6-2) Relative Quantification of Sugar Chains

Figure 12:
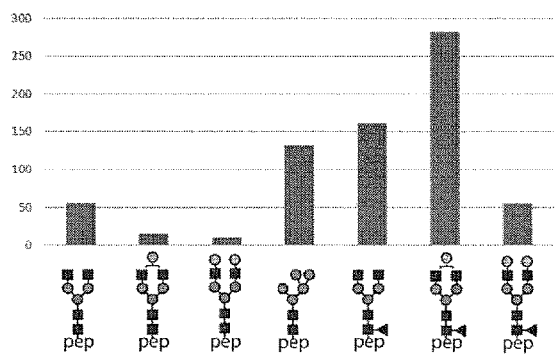
FIG. 12 shows the results of glycosylation site-specific sugar chain quantification for a certain mAb and a human myeloma-derived IgG1 obtained by comparative quantification using samples to which an internal standard was added.
Figure 12:
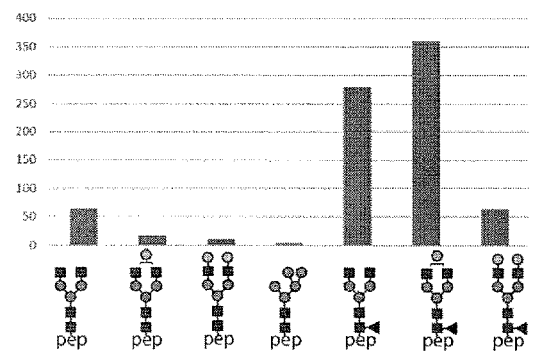
Figure 13A:
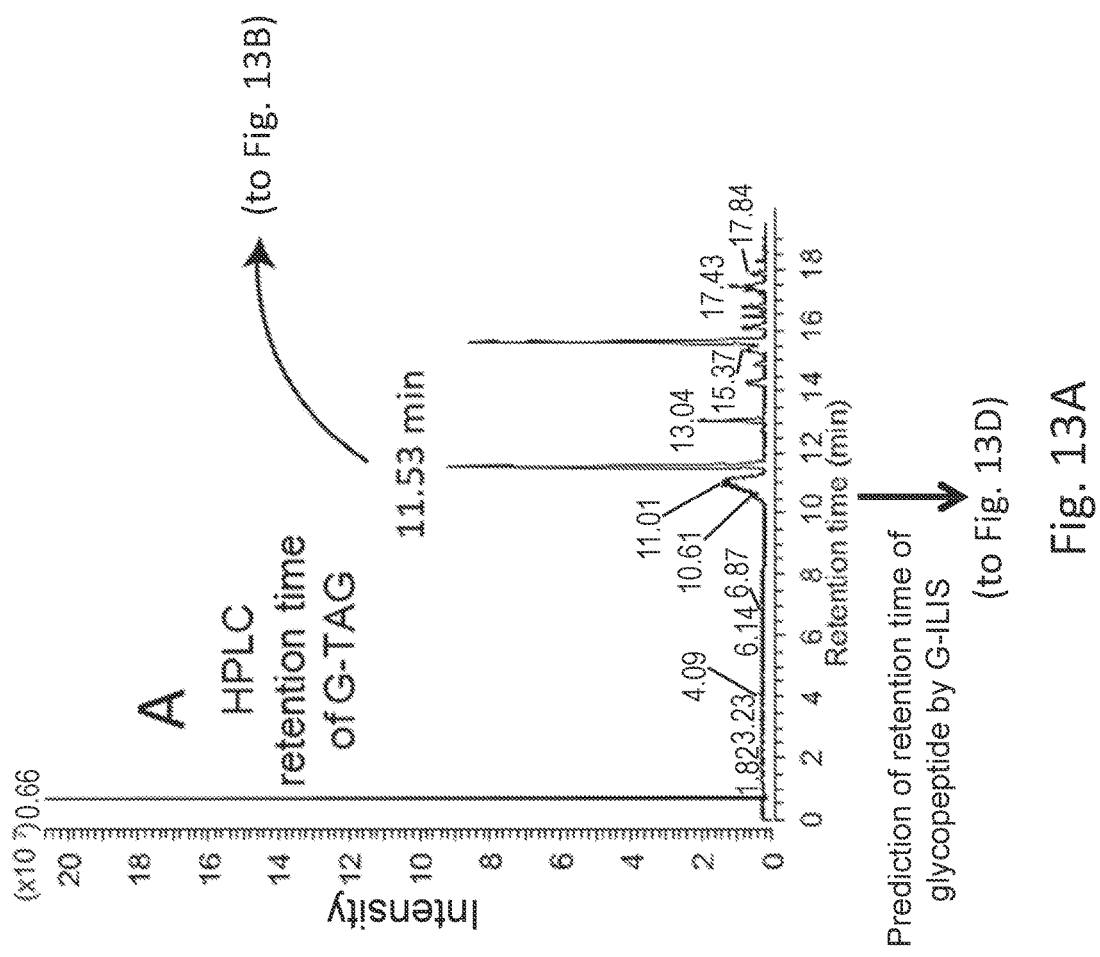
FIGS. 13A, 13B, 13C, 13D, 13E, and 13F show results of Analysis Example 1 in which sugar chains of IgG1, as one example of antibody therapeutics, were analyzed according to the method of the present invention.
Figure 13B:
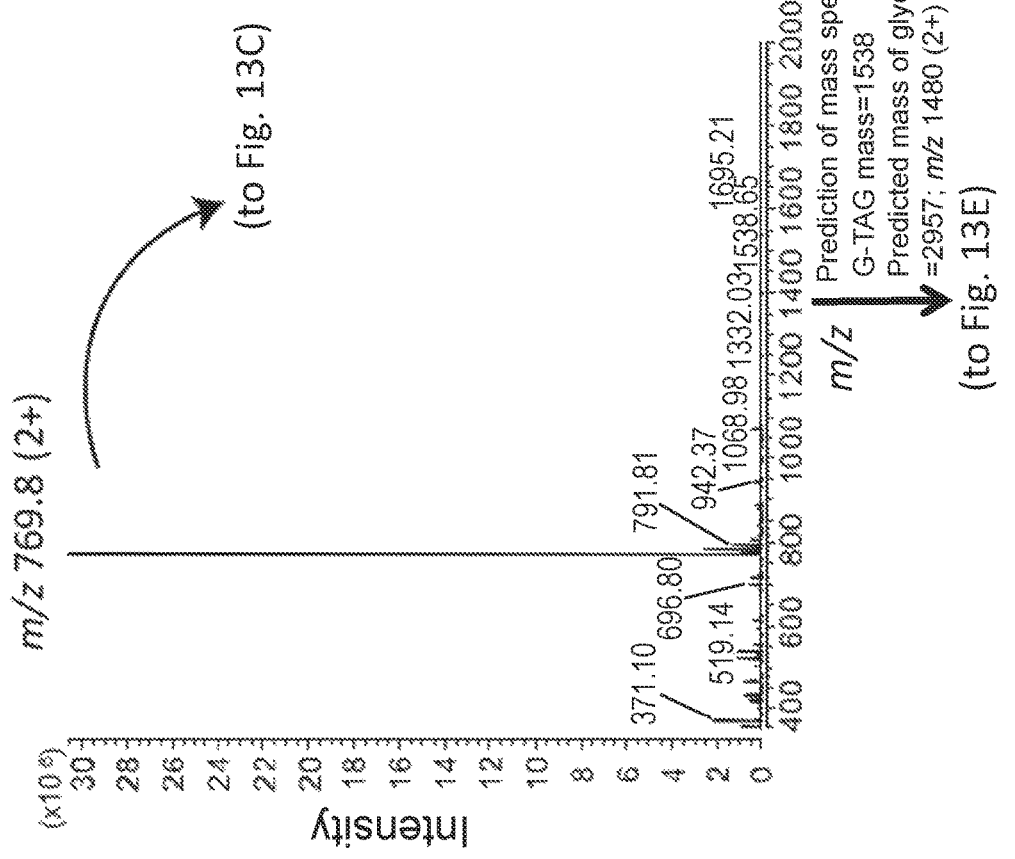
Figure 13C:
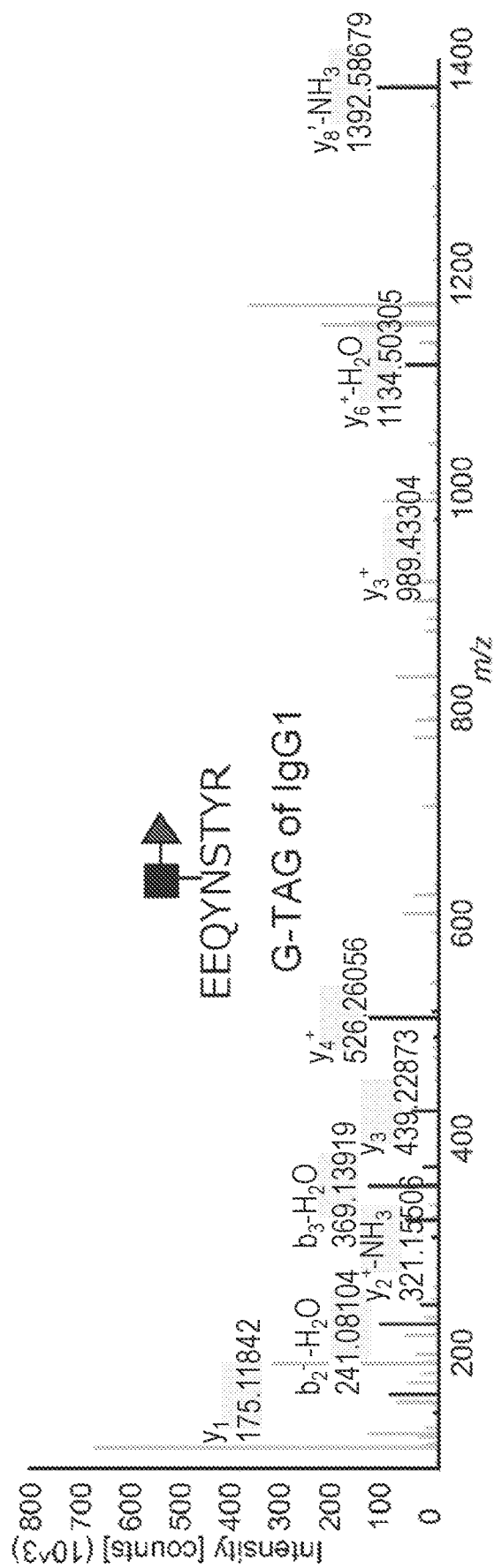
Figure 13D:
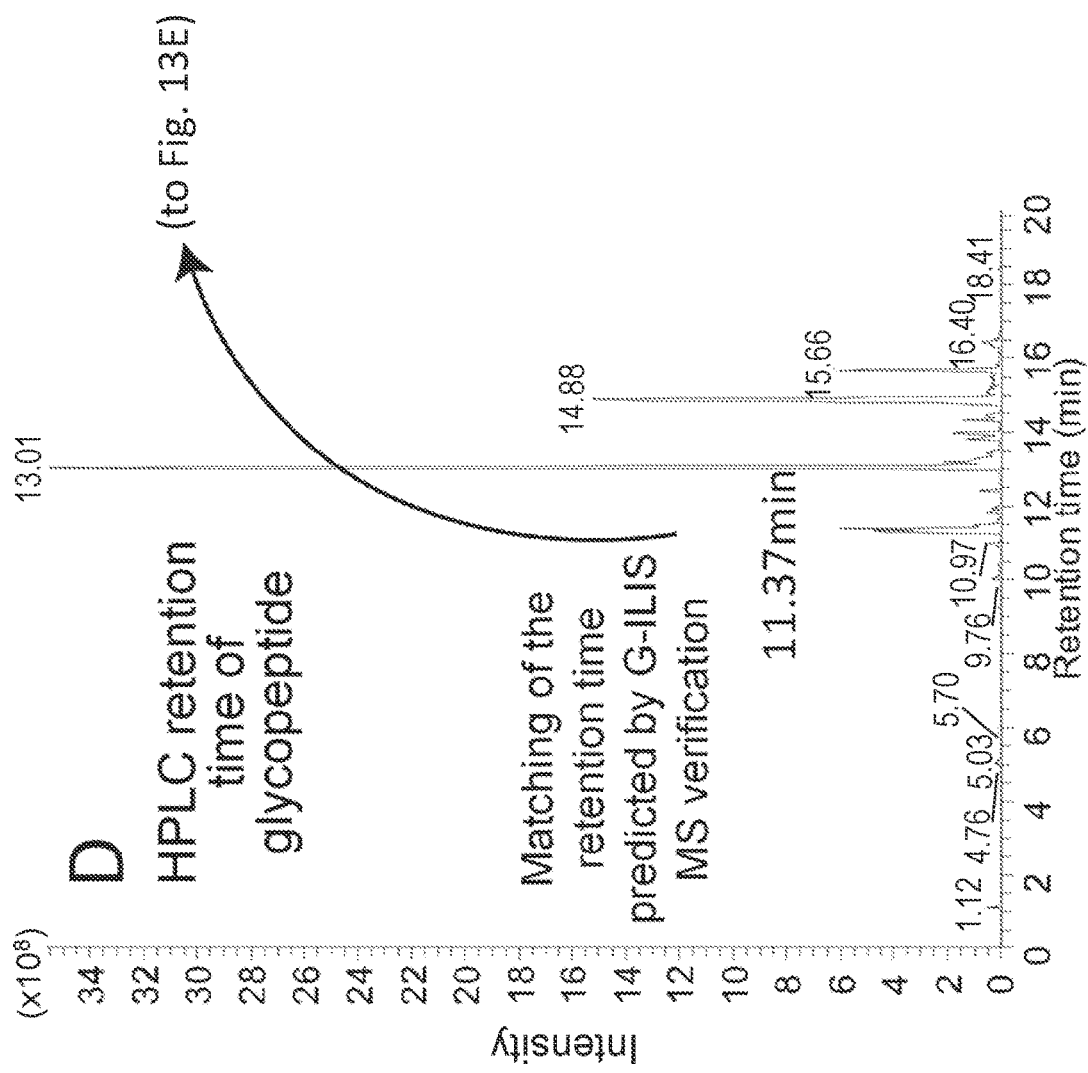
Figure 13E:
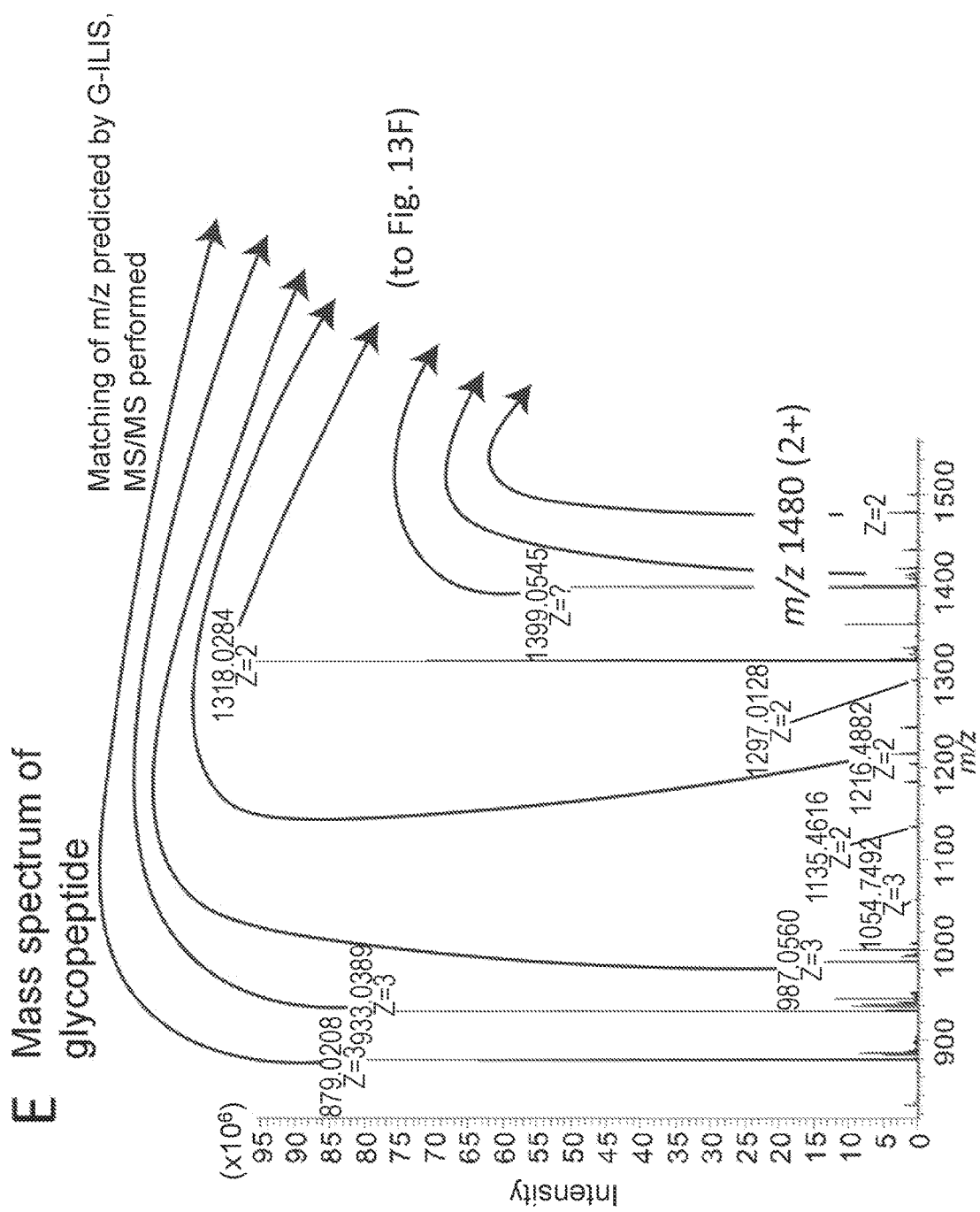
Figure 13F:
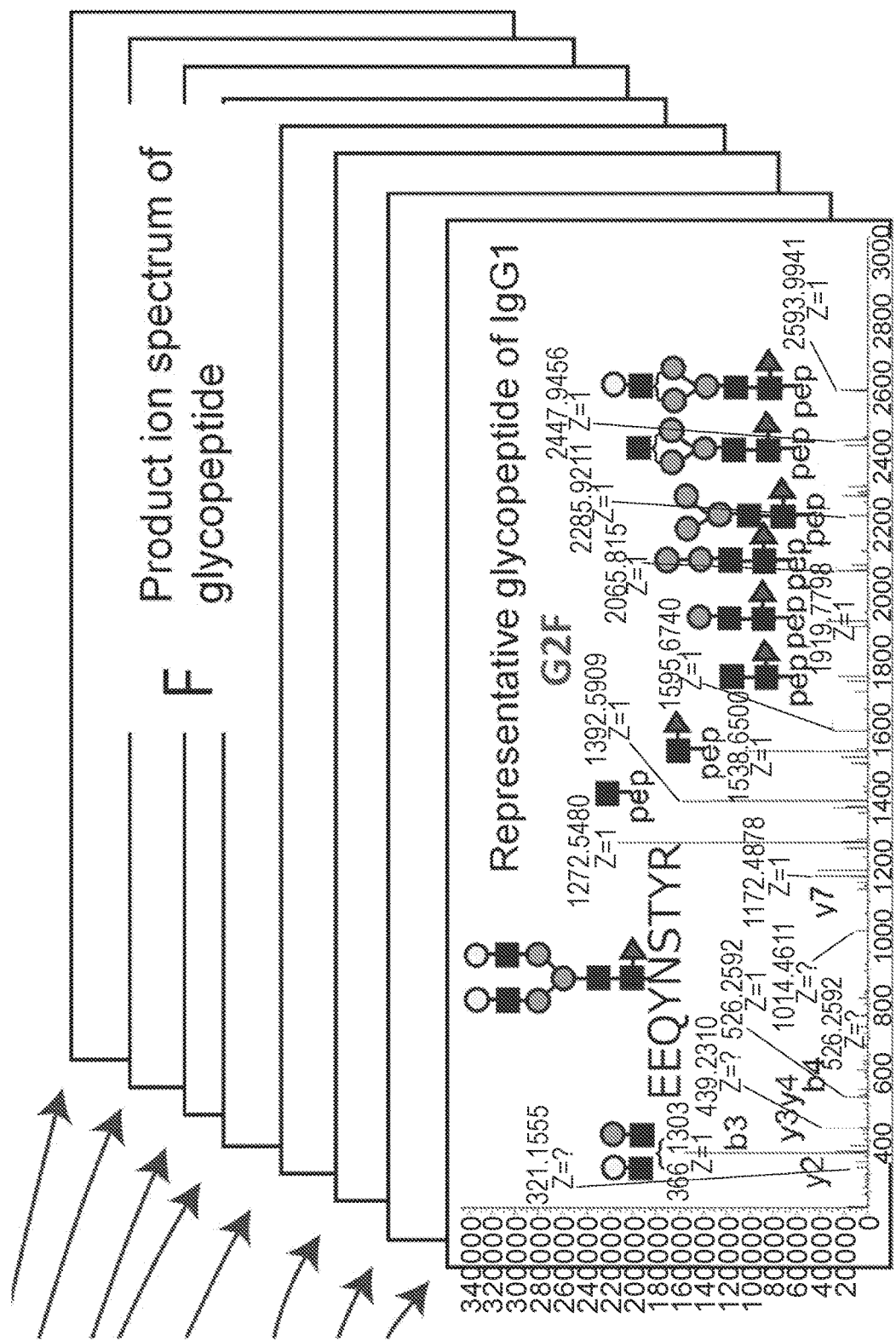

Next, sugar chains at the glycosylation site were relatively quantified. Extracted ion chromatograms of the internal standard (m/z 769.83) and glycopeptides (e.g., m/z 879.02, 933.04) were generated. Then, each peak area was calculated, and the peak area of each glycopeptide was divided by the peak area of the internal standard and multiplied by 100, to obtain a comparative quantification result of sugar chains at the glycosylation site, for each of the certain mAb and human myeloma-derived IgG1, as shown in FIG. 12.

Example 3: Analysis Examples of Model Glycoproteins

Analysis examples in which several types of model glycoproteins were analyzed by the method for sugar chain analysis of the present invention are shown. In the following analysis examples, a step of estimating the retention time and m/z of glycopeptides before the sugar chain cleavage based on the preliminary LC/MS/MS results and carrying out LC/MS/MS or LC/MS$^n$ of glycopeptides before the sugar chain cleavage based on the estimation results is expressed as G-ILIS (Glycopeptide-inclusion list data-dependent acquisition MS).

Analysis Example 1: IgG1 (An Example of Antibody Therapeutics)

Sugar chains of IgG1 (human antibody) different from the IgG1 antibody used in Examples 1 and 2 were analyzed by the following procedure. The basic operations were performed in the same manner as in Example 1.

(Preliminary LC/Mass Spectrometry)

A glycopeptide-concentrated sample obtained by recovering glycopeptides from a tryptic digest of IgG1 was treated with endoglycosidases F1 to F3, to prepare a sample containing peptides whose sugar chains were cleaved off while leaving one GlcNAc or GlcNAc-Fuc residue on the asparagine residue (which sample is hereinafter referred to as G-TAG). G-TAG was subjected to LC/MS/MS to obtain base peak chromatogram, mass spectrum and product ion spectrum of G-TAG.

(G-ILIS)

Based on the retention time and the mass of G-TAG obtained in the preliminary LC/mass spectrometry, the retention time and the m/z of glycopeptides before the sugar chain cleavage were estimated, and the estimates of m/z (calculated in a similar manner as in Example 1) were listed. List-dependent LC/MS/MS (G-ILIS) was carried out under the same conditions as the preliminary LC/mass spectrometry to obtain base peak chromatogram, mass spectrum, and product ion spectrum of IgG1 glycopeptides and determine the sugar chain structures.

Analysis Conditions:
NanoLC, EASY-nLC™ 1000 (Thermo Fisher Scientific, Waltham, Mass.); trap column, Acclaim™ PepMap™ 100 C18 (3 µm, 0.075 mm×10 mm; Thermo Fisher Scientific); analytical column, NTCC-360/75-3-125 (C18, particle diameter 3 µm, 0.075 mm×125 mm; Nikkyo Technos); hybrid quadrupole-orbitrap mass spectrometer, Q Exactive™ (Thermo Fisher Scientific); elution condition: a linear gradient of solution A (0.1% (v/v) formic acid/water) and solution B (0.1% (v/v) formic acid/acetonitrile) at 300 nL/min (0-15 min, 0-35% solution B; 15-20 min, 35-100% solution B.

The analysis results are shown in FIG. 13. The upper panels (A to C) show results of LC/MS/MS (preliminary LC/mass spectrometry) of G-TAG. The retention time of G-TAG was 11.53 min. A mass spectrum peak around this retention time (m/z 769.8 (2+), matching with calculated mass was verified) was extracted, and a product ion spectrum was obtained. Then, MS/MS ion search taking into account the GlcNAc or GlcNAc-Fuc modification on the Asn residue was performed to identify the glycosylation site and the amino acid sequence of the IgG1-derived G-TAG.

The lower panels (D to F) in FIG. 13 are the results of G-ILIS. Based on the retention time (A) and the mass (B) of G-TAG, the retention time and the m/z of IgG1-derived glycopeptides before the sugar chain cleavage were estimated, and the estimates of m/z were listed. In the base peak chromatogram (D) of IgG1-derived glycopeptides before the sugar chain cleavage, a peak of the target glycopeptide was observed at 11.37 min (within the range calculated by setting Δt to 0.5 min in the above-described Formula 1), which was very close to the retention time of G-TAG. A peak matching with the m/z estimate was observed in the mass spectrum (E) of the fraction at around 11.37 min, demonstrating that the m/z of the glycopeptides could be predicted from the analysis results of G-TAG. By using each glycopeptide whose m/z matched with the estimated m/z found in the mass spectrum shown in panel E as a precursor ion, the product ion spectra were obtained. As a result, as shown in panel F, the sugar chain structure of each glycopeptide could be determined (panel F shows a product ion spectrum and fragment assignments for glycopeptides bound with G2F, a representative sugar chain of IgG1).

Analysis Example 2: Ribonuclease B (an Example of High-Mannose Glycosylated Proteins)

In the same manner as in Analysis Example 1, sugar chains of ribonuclease B (RNase B) (bovine pancreatic: SIGMA-ALDRICH) were analyzed.

Figure 14A:
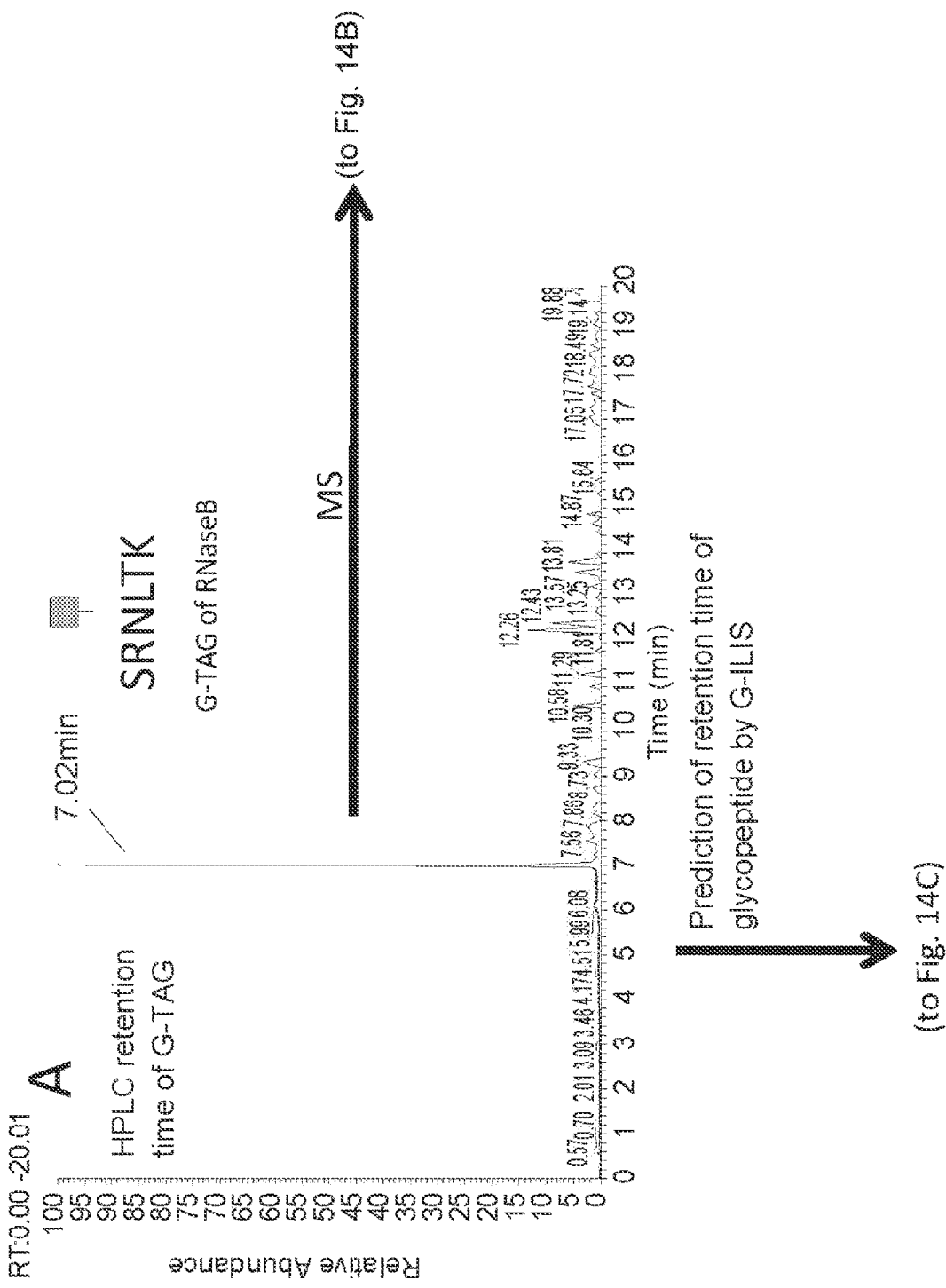
Figure 14B:
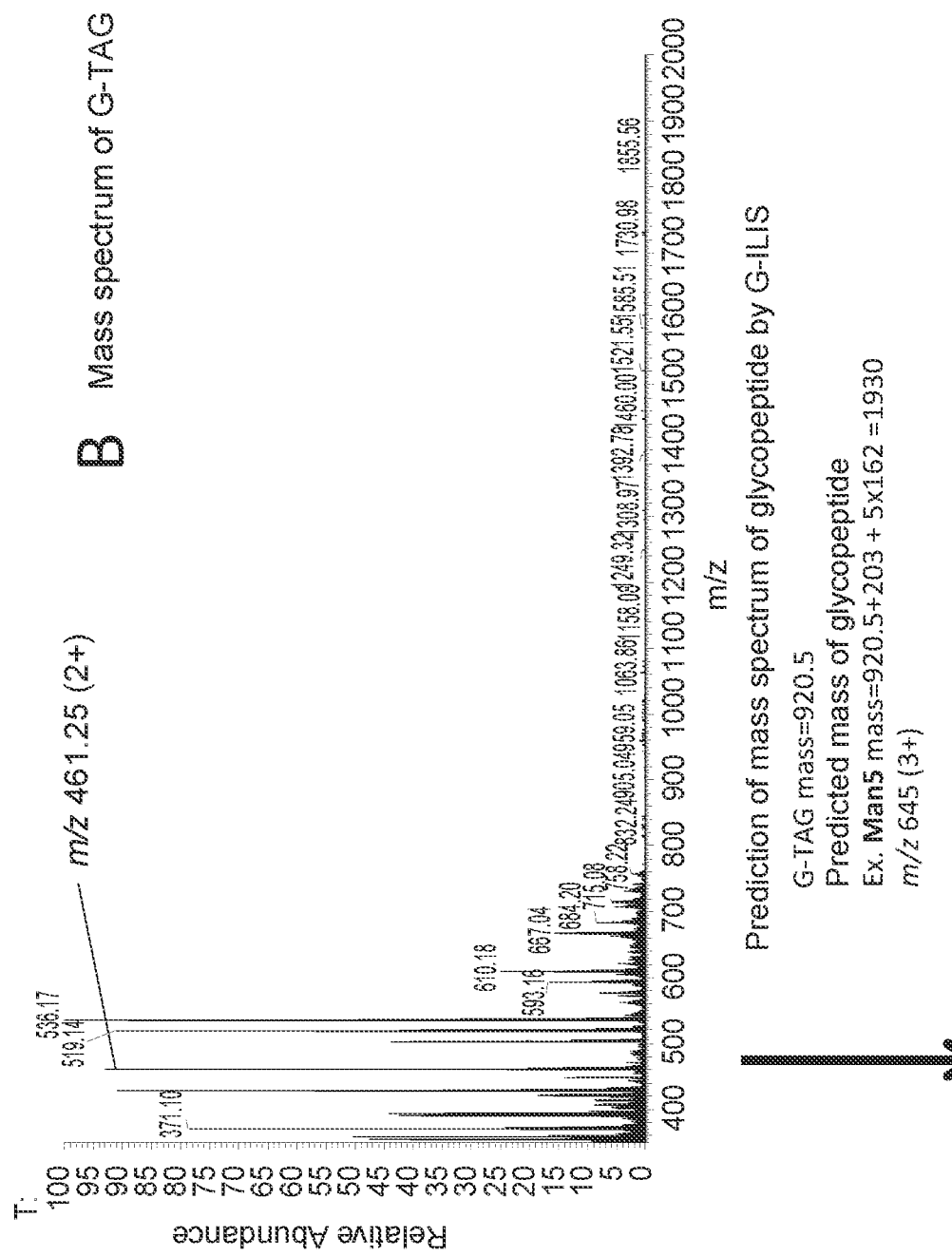
Figure 14D:
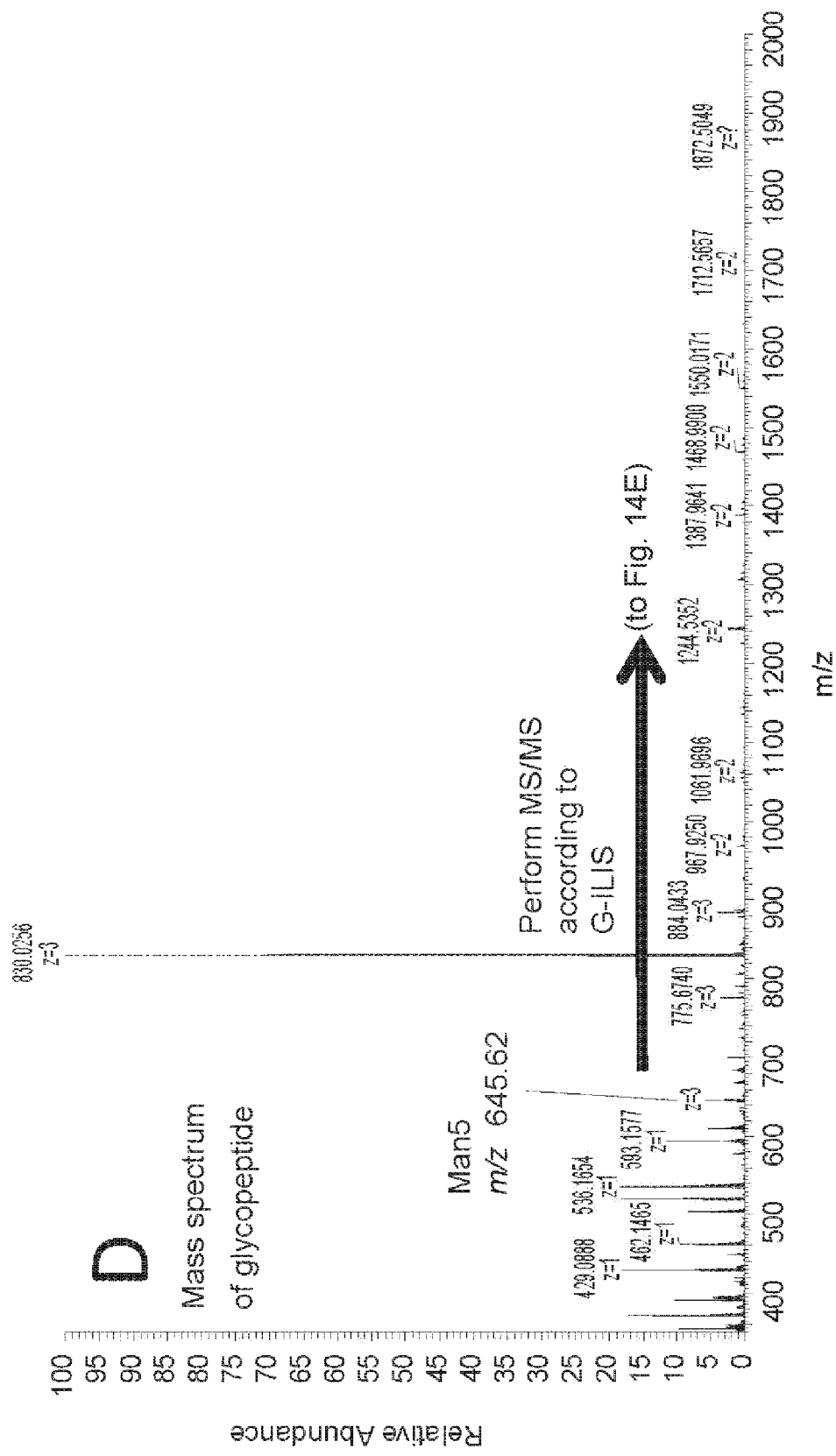

The results are shown in FIG. 14. The upper panels (A and B) show results of LC/MS/MS (preliminary LC/mass spectrometry) of G-TAG. The lower panels (C to E) show results of G-ILIS. The retention time of RNase B-derived G-TAG was 7.02 min (A). In the extracted ion chromatogram (C) of RNase B-derived glycopeptides before the sugar chain cleavage, a peak of the target glycopeptide was observed at 7.26 min (within the range calculated by setting Δt to 0.5 min in the above-described Formula 1), which was very close to the retention time of G-TAG. A peak matching with the m/z estimate was observed in the mass spectrum (D) of the fraction at around the retention time of 7.26 min. Thus it was also confirmed in this Analysis Example that the m/z of the glycopeptides could be predicted from the analysis results of G-TAG. By using each glycopeptide whose m/z matched with the estimated m/z found in the mass spectrum shown in panel D as a precursor ion, the product ion spectrum was obtained. As a result, as shown in panel E, the sugar chain structure of each glycopeptide could be determined (panel E shows a product ion spectrum and fragment assignments for glycopeptides bound with Man5, a representative sugar chain of RNase B).

Thus, as demonstrated above, the sugar chains of ribonuclease B, a glycoprotein having high mannose type sugar chains, could also be analyzed by the method of the present invention.

Analysis Example 3: Transferrin (an Example of Sialylated Complex Biantennary Glycosylated Proteins)

In the same manner as in Analysis Example 1, sugar chains of transferrin (TO (human; SIGMA-ALDRICH) were analyzed.

Figure 15B:
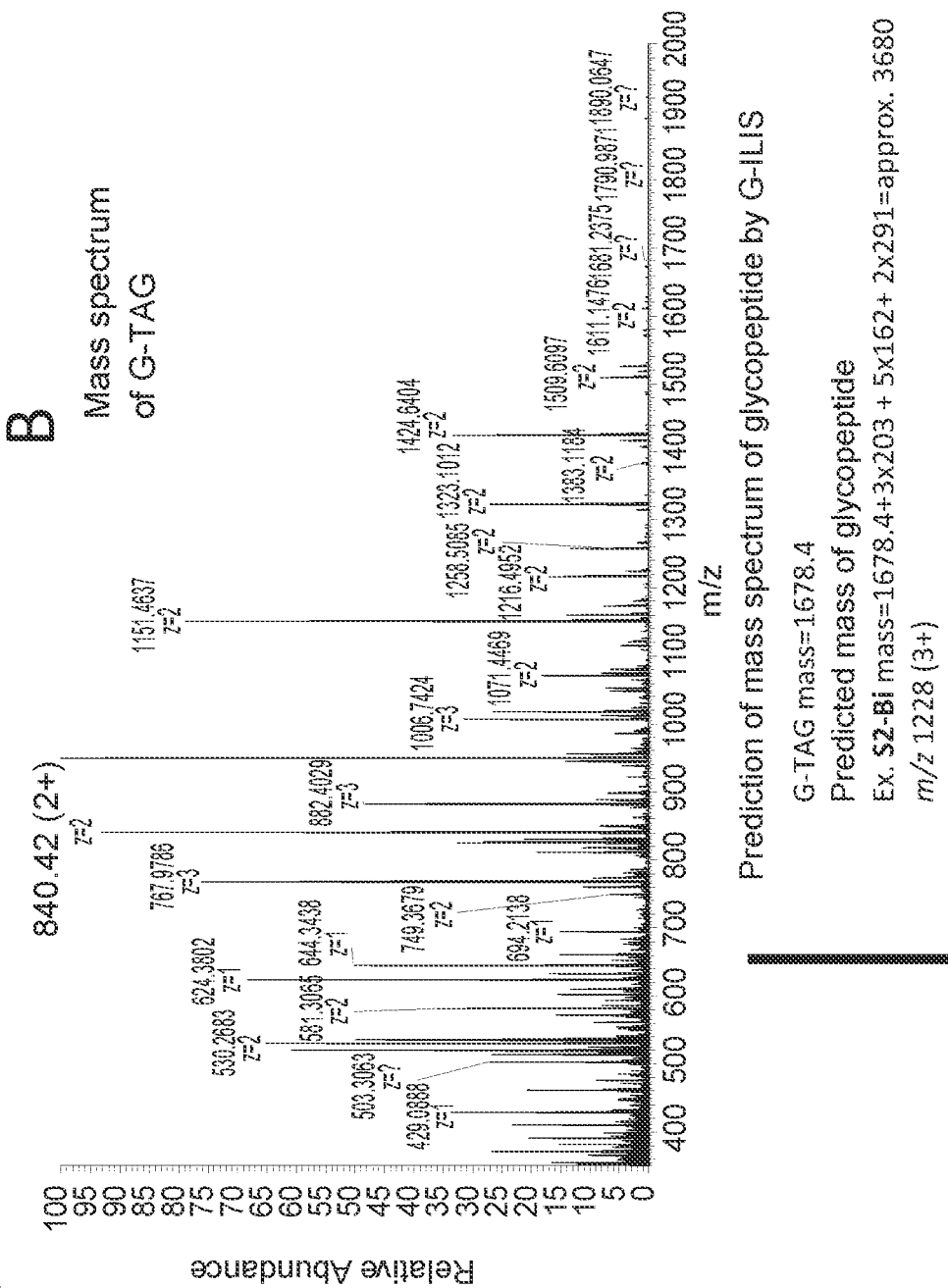
Figure 15E:
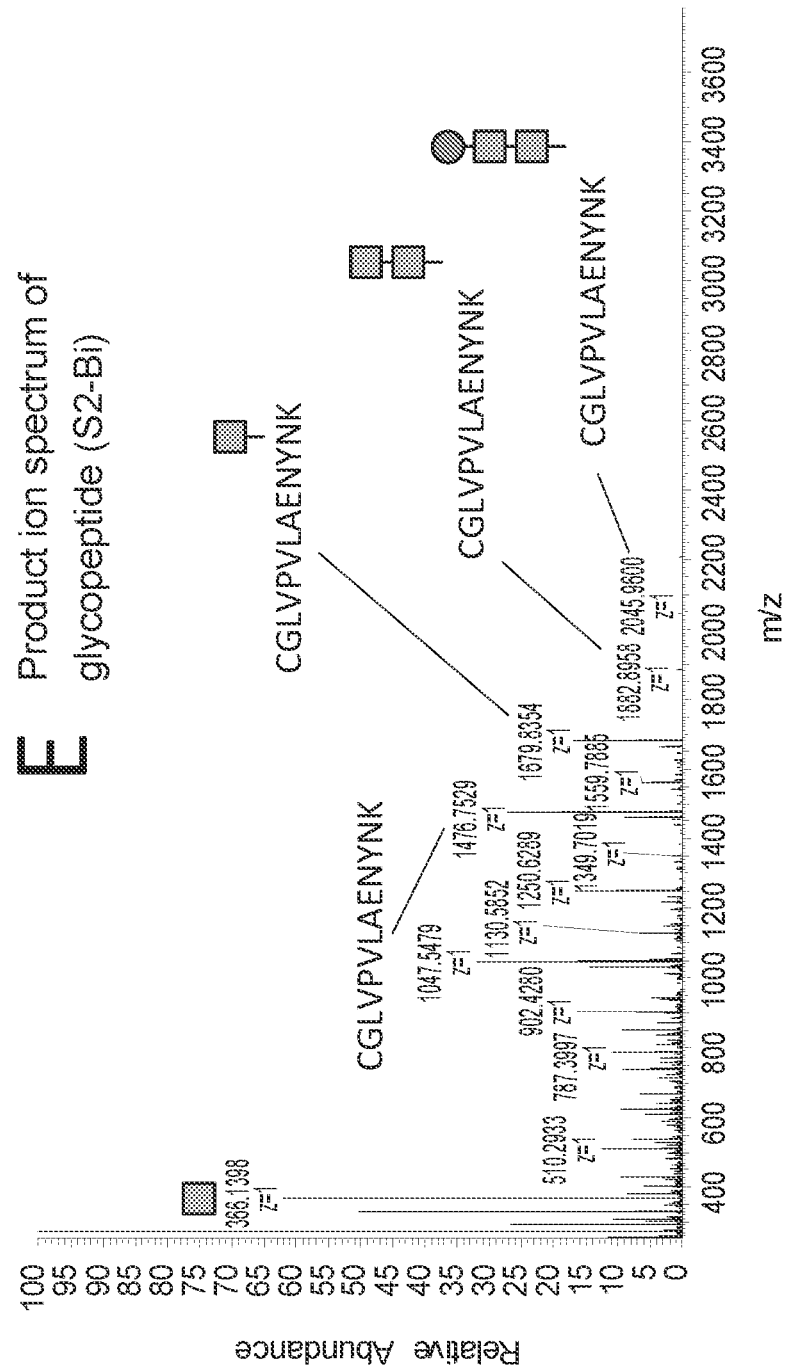
Figures 1, 16A:
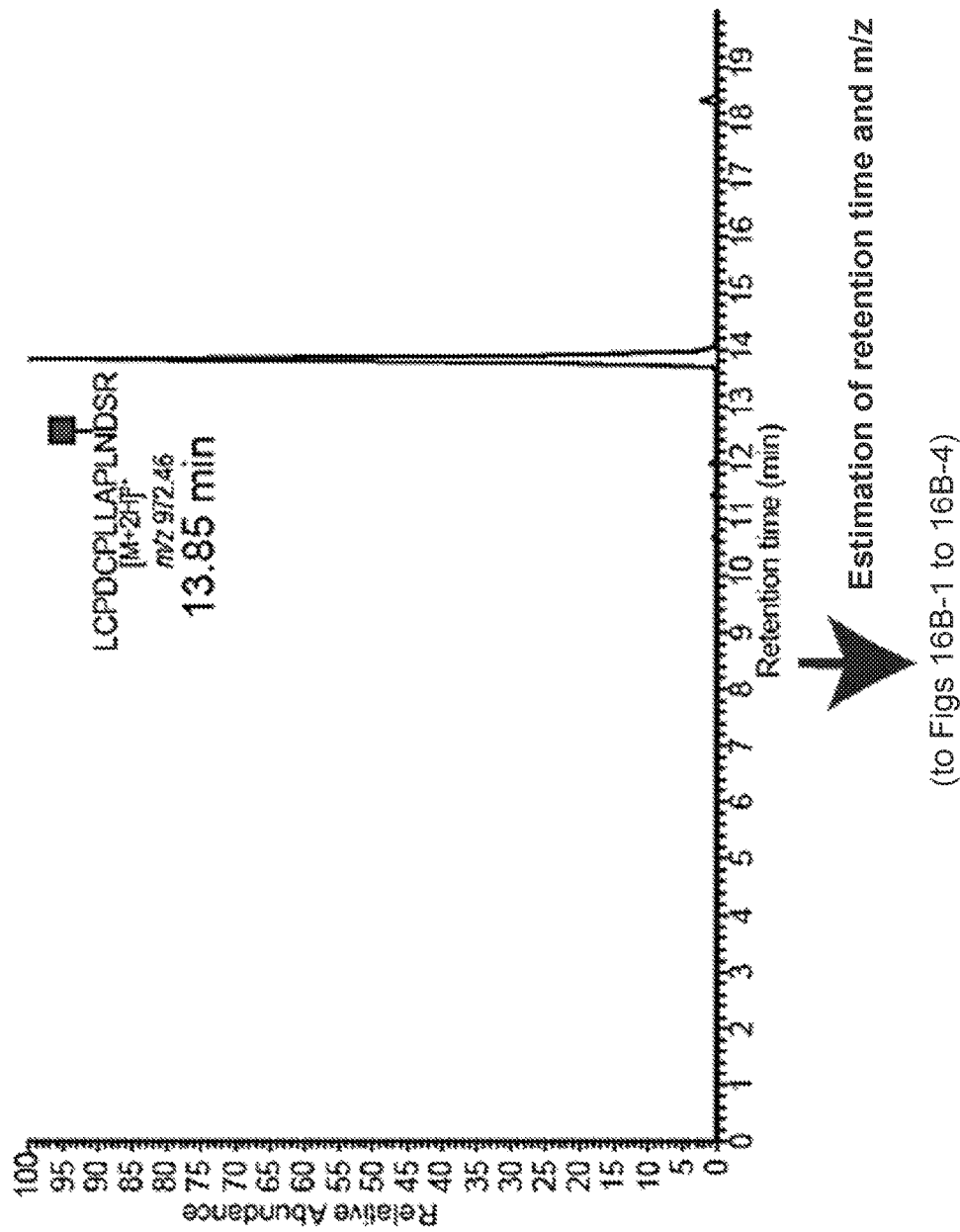
Figures 2, 16A:
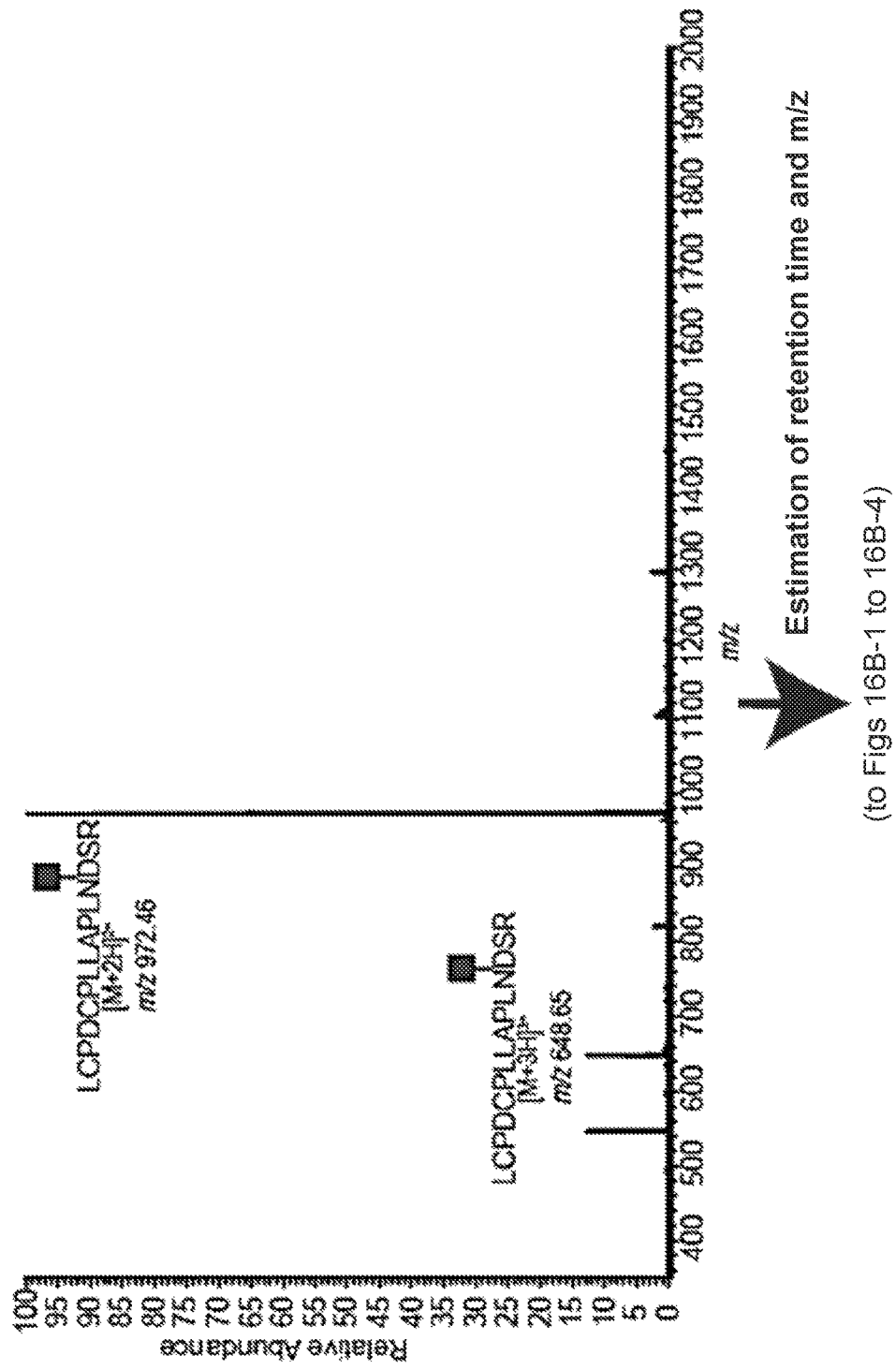
Figures 3, 16A:
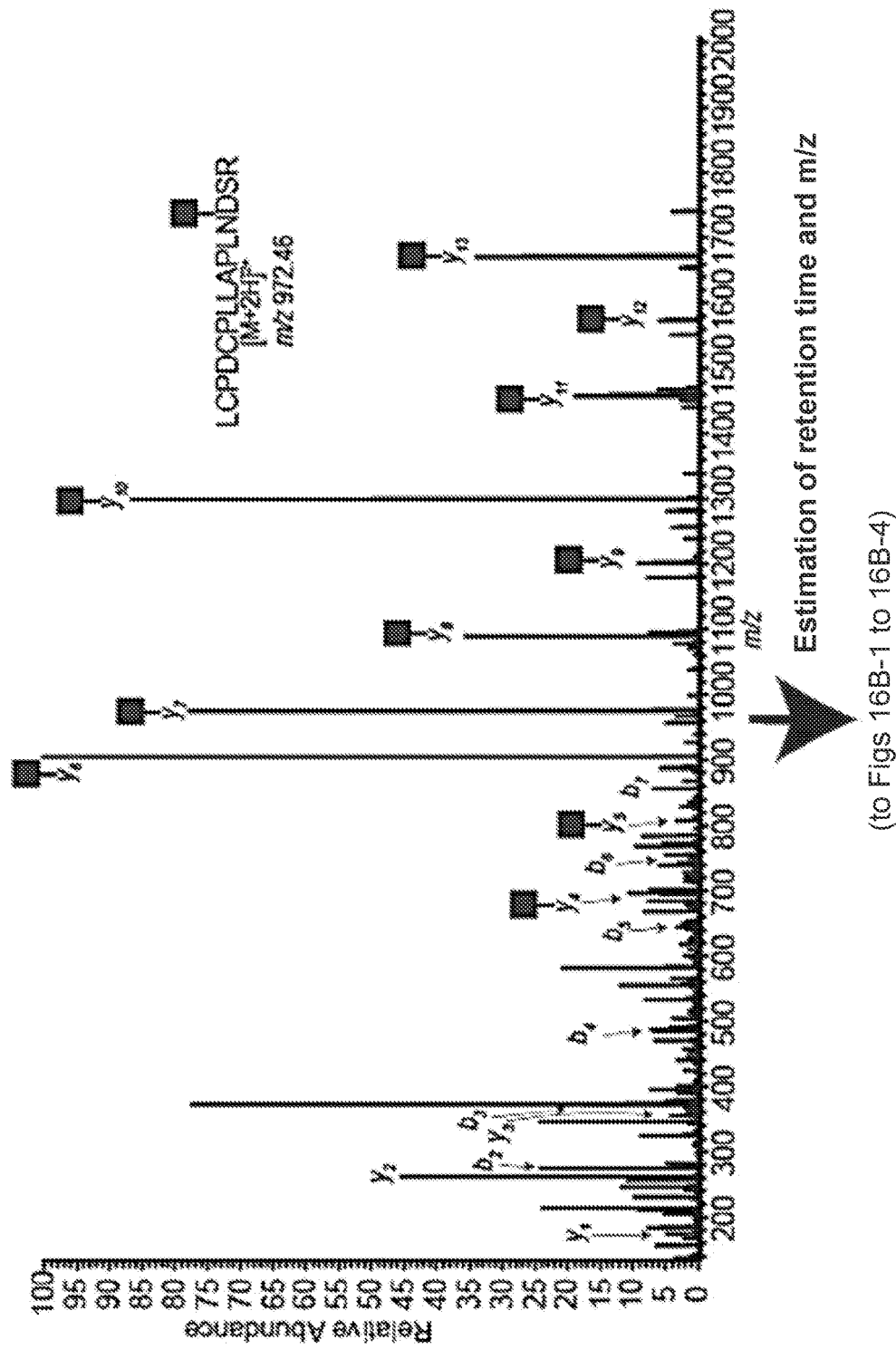
Figures 1, 16B:
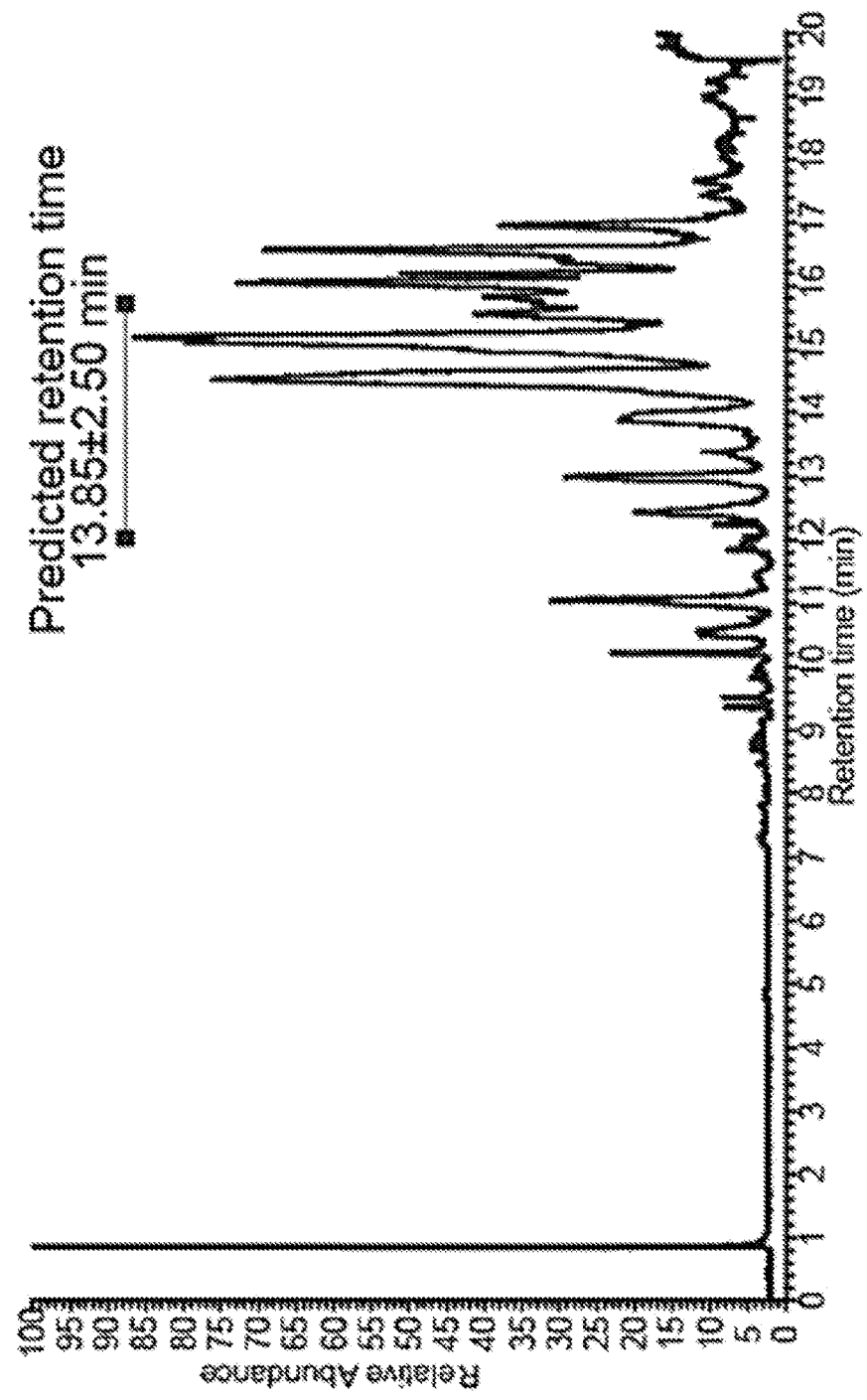
Figure 16B:
Figure 4:
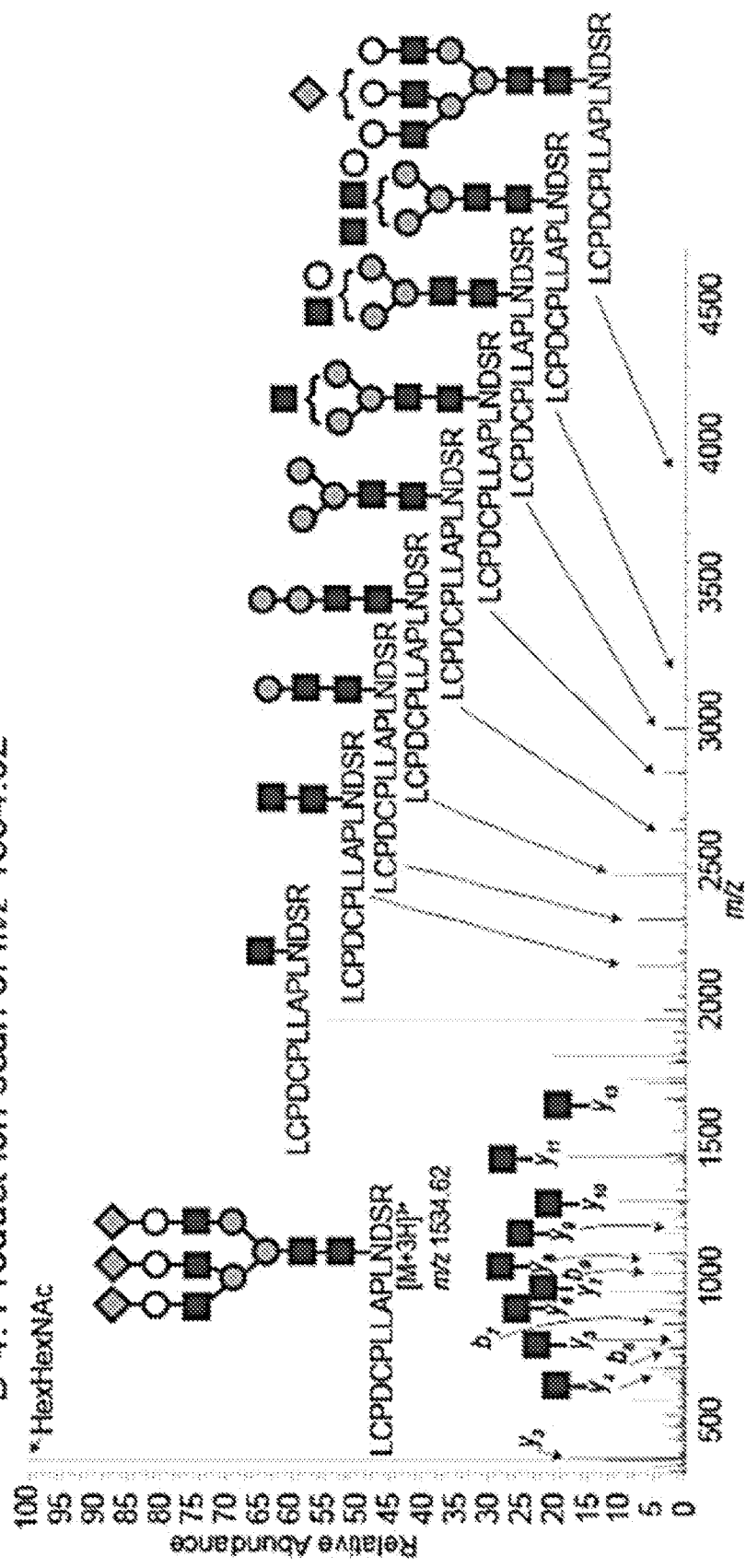
Figures 1, 17A:
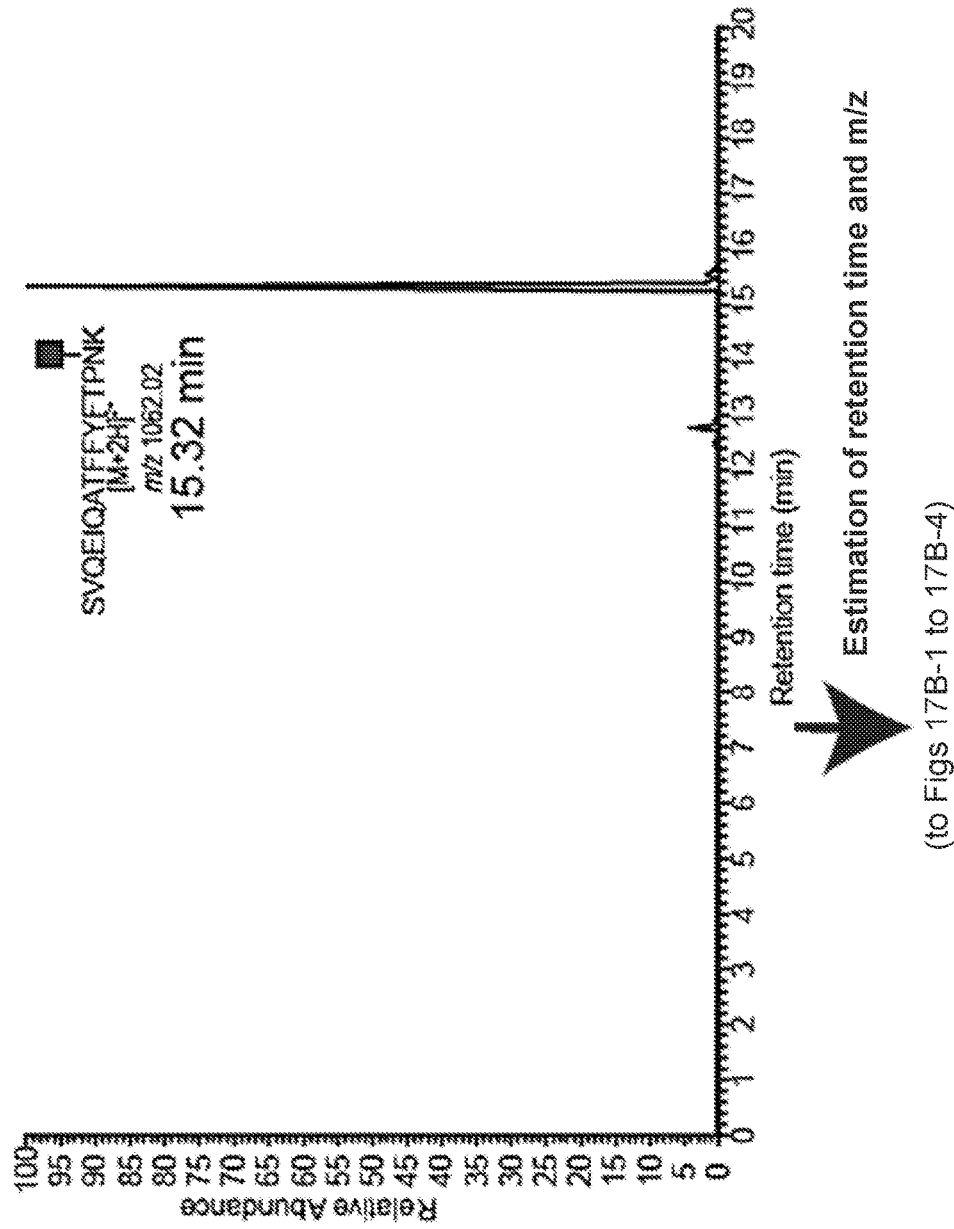
Figures 2, 17A:
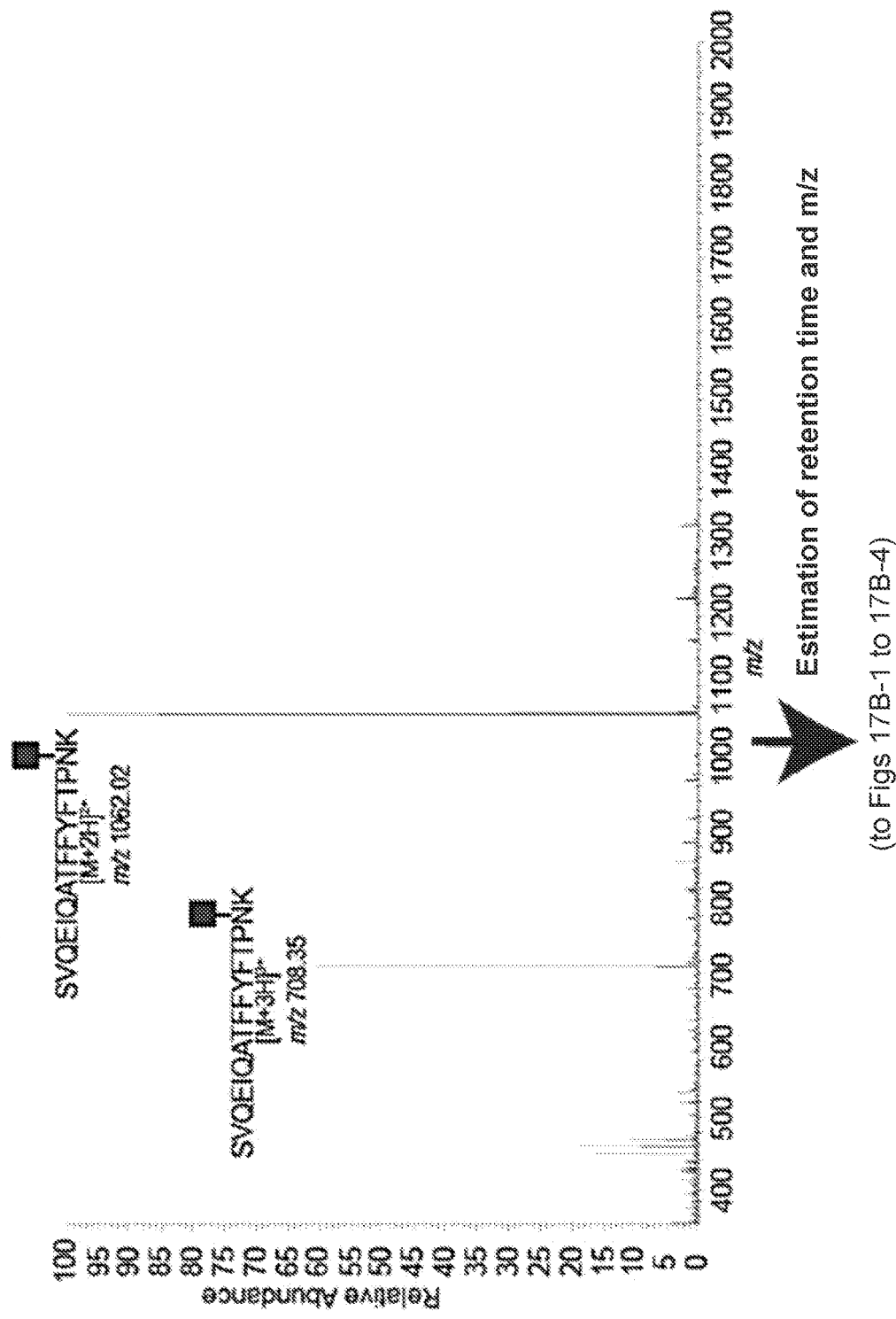
Figures 3, 17A:
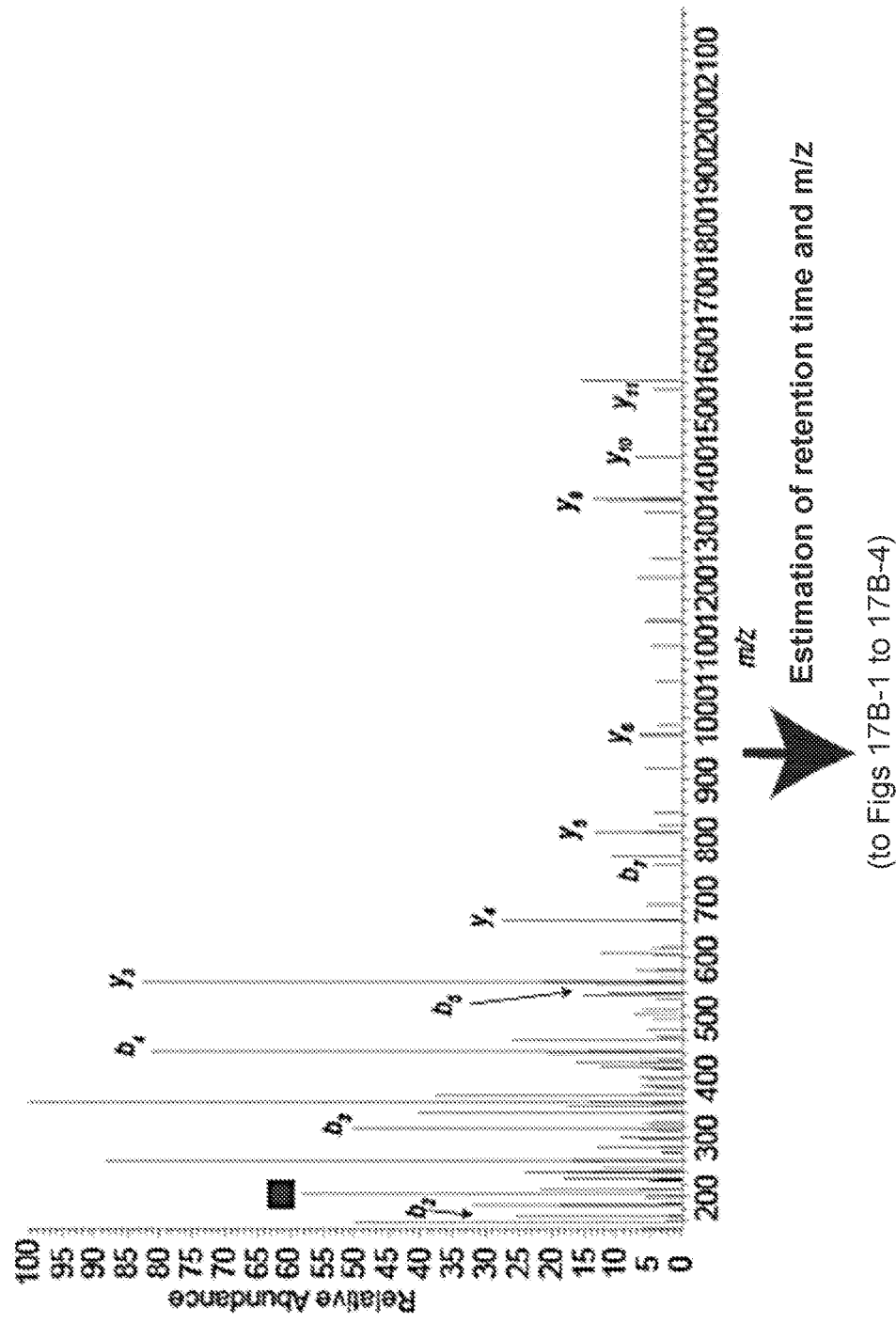
Figures 1, 17B:
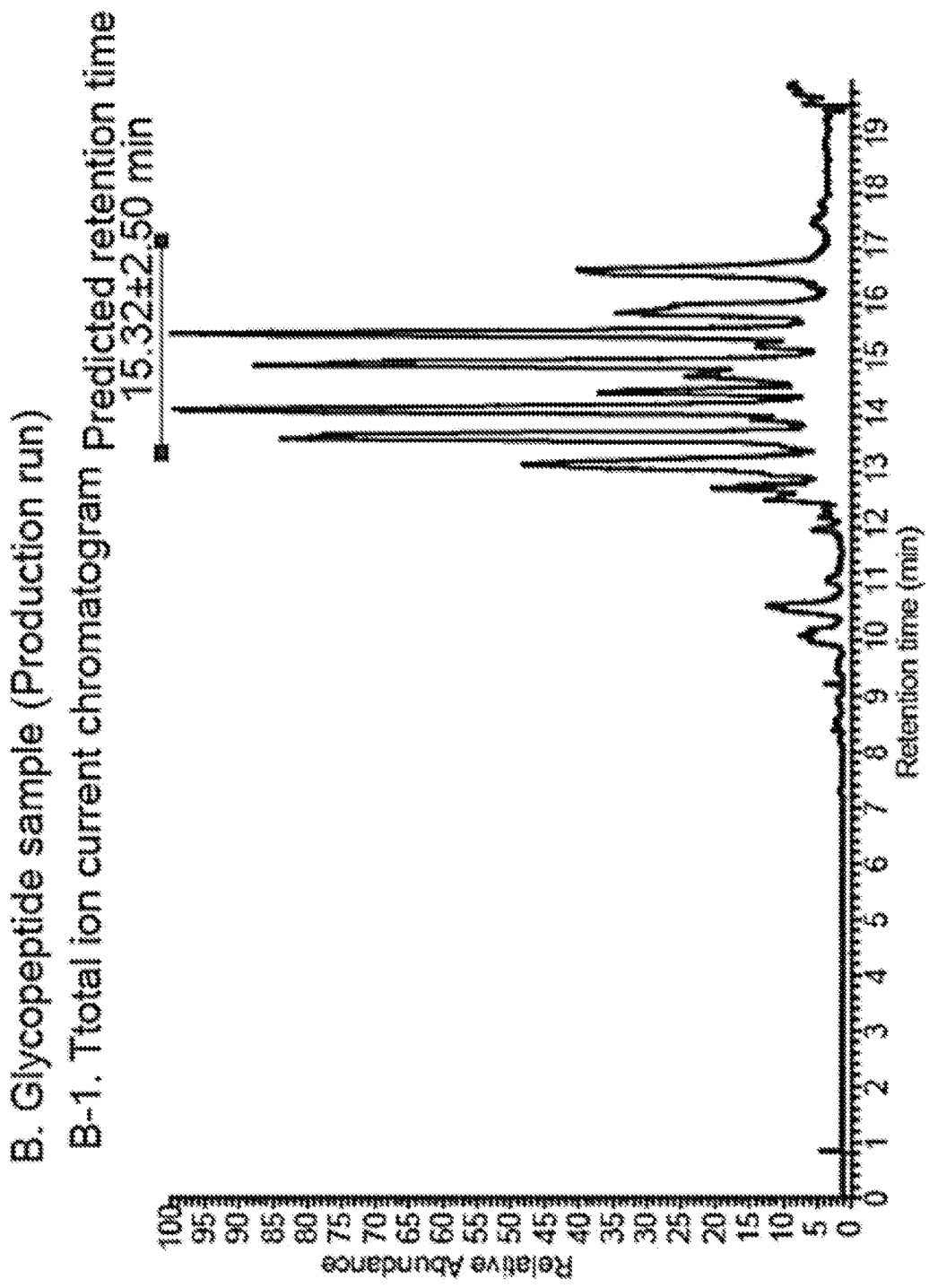
Figures 2, 17B:
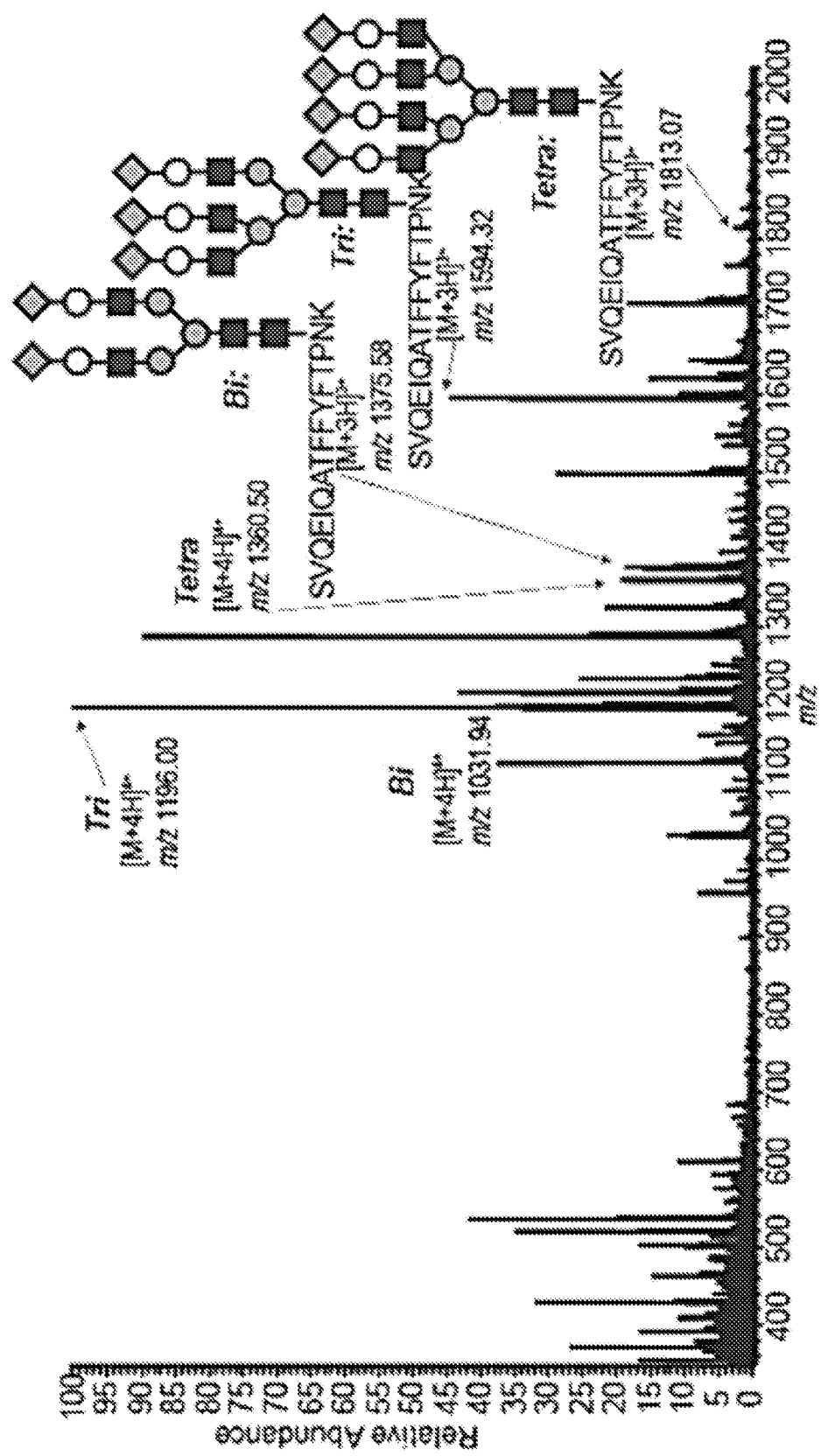
Figures 3, 17B:
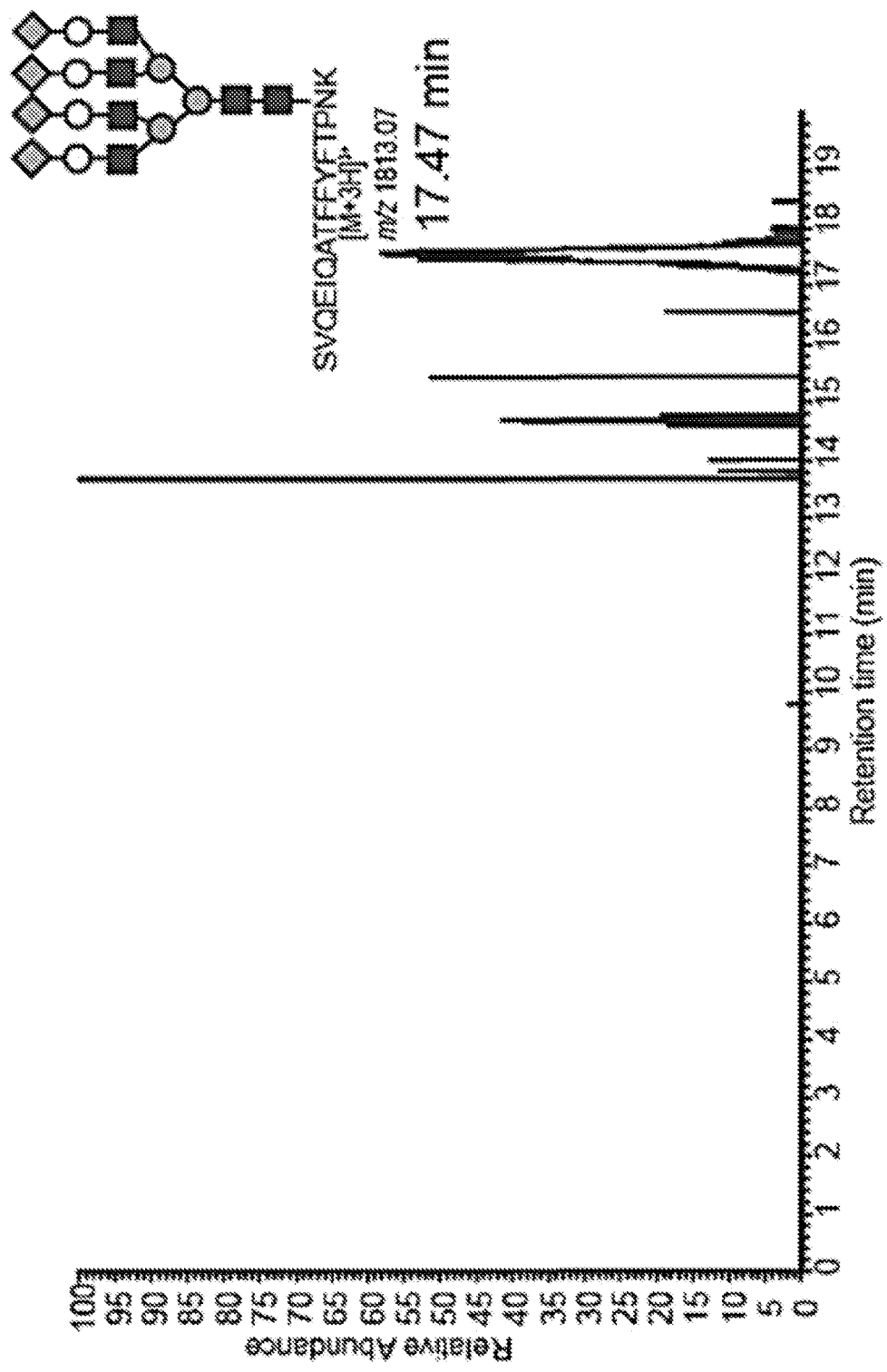
Figures 4, 17B:
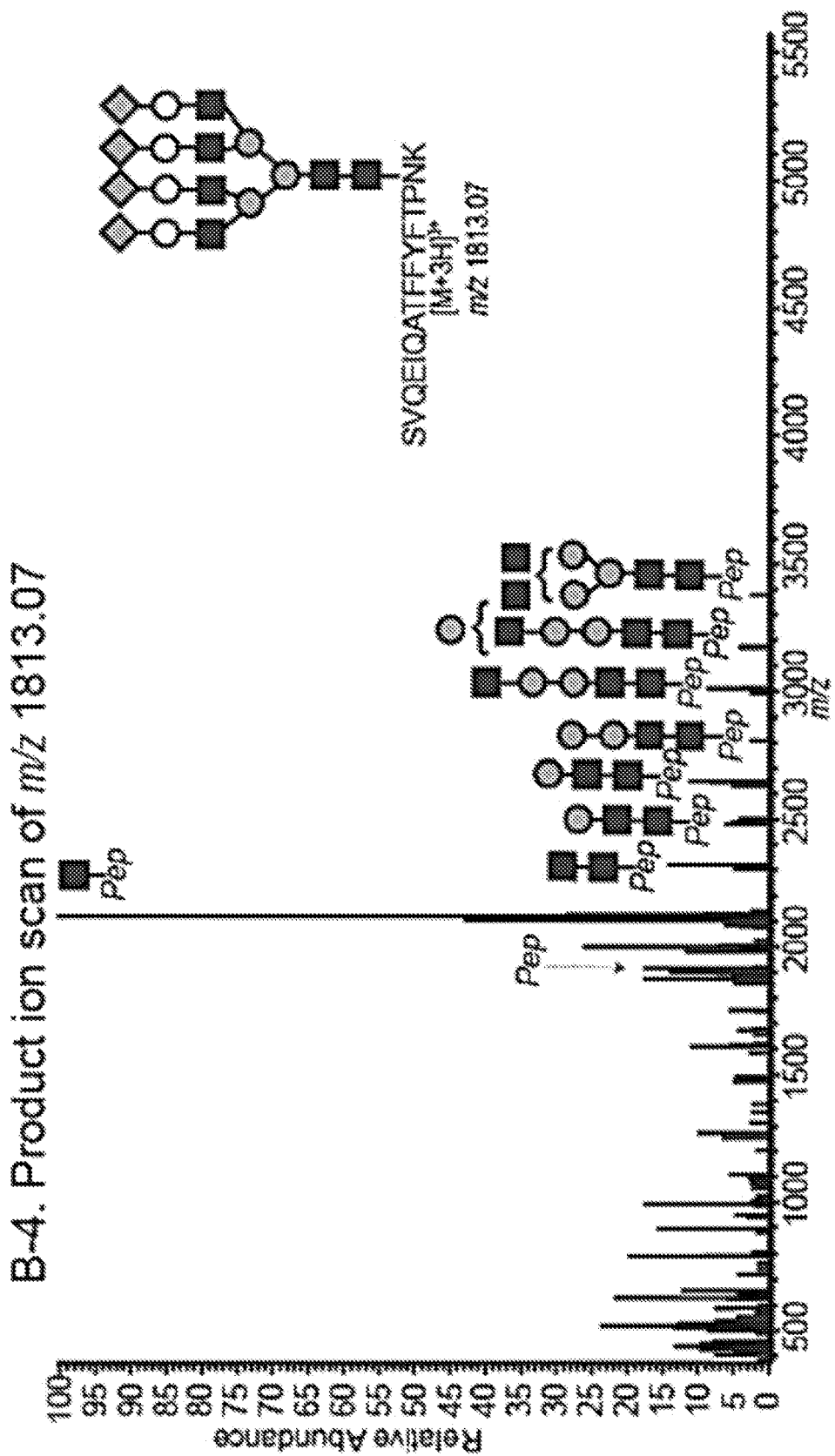

The results are shown in FIG. 15. The upper panels (A and B) show results of LC/MS/MS (preliminary LC/mass spectrometry) of G-TAG. The lower panels (C to E) show results of G-ILIS. The retention time of Tf-derived G-TAG having the sequence CGLVPVLAENYNK was 13.41 min (A). In the extracted ion chromatogram (C) of Tf-derived glycopeptides before the sugar chain cleavage which had the sequence CGLVPVLAENYNK, a peak of the target glycopeptide was observed at 14.12 min (within the range calculated by setting Δt to 1 min in the above-described Formula 1), which was very close to the retention time of G-TAG. A peak matching with the m/z estimate was observed in the mass spectrum (D) of the fraction at around the retention time of 14.12 min. Thus it was also confirmed in this Analysis Example that the m/z of the glycopeptides could be predicted from the analysis results of G-TAG. By using each glycopeptide whose m/z matched with the estimated m/z found in the mass spectrum shown in panel D as a precursor ion, the product ion spectrum was obtained. As a result, as shown in panel E, the sugar chain structure of each glycopeptide could be determined (panel E shows a product ion spectrum and fragment assignments for glycopeptides bound with disialo biantennary (S2-Bi), a representative sugar chain of Tf).

Thus, as demonstrated above, the sugar chains of transferrin, a glycoprotein having complex sugar chains comprising sialic acid, could also be analyzed by the method of the present invention.

Analysis Examples 4 and 5: Fetuin and α1-Acid Glycoprotein

As additional analysis examples of sialylated complex glycosylated proteins, sugar chains of fetuin that has a triantennary sugar chain (derived from fetal bovine serum; SIGMA-ALDRICH) and al-acid glycoprotein that has a tetraantennary sugar chain (derived from human plasma; SIGMA-ALDRICH) were analyzed in the same manner as in Analysis Example 1.

The analysis results for sugar chains of fetuin are shown in FIG. 16. The upper panels (A-1 to A-3) show results of LC/MS/MS (preliminary LC/mass spectrometry) of G-TAG having the sequence LCPDCPLLAPLNDSR. The middle and lower panels (B-1 to B-4) show results of G-ILIS. The retention time of fetuin-derived G-TAG was 13.85 min (A-1). From this retention time, the retention time of the glycopeptide before the sugar chain cleavage was estimated to be 13.85±2.50 min. In the total ion current chromatogram of glycopeptide fraction (B-1), many peaks were detected in the range of 13.85±2.50 min. In fact, in the range from 14.61 to 15.19 min, peaks of glycopeptides that had the sequence LCPDCPLLAPLNDSR and matched with the m/z estimates were observed (B-2). It was again confirmed by this analysis example that the retention time and m/z of glycopeptides could be predicted from the result of the G-TAG analysis.

The analysis results for sugar chains of α1-acid glycoprotein are shown in FIG. 17. The upper panels (A-1 to A-3) show results of LC/MS/MS (preliminary LC/mass spectrometry) of G-TAG having the sequence SVQEIQATFFYFTPNK. The middle and lower panels (B-1 to B-4) show results of G-ILIS. The retention time of α1-acid glycoprotein-derived G-TAG was 15.32 min (A-1). From this retention time, the retention time of the glycopeptide before the sugar chain cleavage was estimated to be 15.32±2.50 min. In the total ion current chromatogram of glycopeptide fraction (B-1), many peaks were observed in the range of 15.32±2.50 min. In fact, in the range from 15.83 to 17.75 min, peaks matching with the m/z estimates were observed (B-2). It was again confirmed by this analysis example that the retention time and m/z of glycopeptides could be predicted from the result of the G-TAG analysis.

Thus, as demonstrated above, the sugar chains of fetuin and α1-acid glycoprotein, glycoproteins having sialylated complex sugar chains different from that of transferrin, could also be analyzed by the method of the present invention.

DESCRIPTION OF SYMBOLS

100: system for analyzing a sugar chain(s) of the present invention
10: preliminary liquid chromatography/mass spectrometry data acquisition unit
12: glycosylation site determination unit
14: retention time and m/z estimation unit
16: main analysis unit
161: unit for acquisition of liquid chromatography/mass spectrometry data of a main analysis sample
162: target peak selection unit
163: sugar chain structure determination unit
164: sugar chain quantification unit
20: input unit
30: output unit

The invention claimed is:

1. A method of analyzing N-linked sugar chain(s) of glycoprotein, comprising:
- a glycoprotein fragmentation step of fragmenting glycoprotein having N-linked sugar chain(s) to obtain a glycopeptide-containing sample;
- a sugar chain cleavage step of allowing a part of the glycopeptide-containing sample to react with an endo-β-N-acetylglucosaminidase(s) and cleaving the β-1,4 linkage in chitobiose present at a junction between each sugar chain and an asparagine (Asn) residue, thereby cleaving off the sugar chain(s) while leaving one N-acetylglucosamine (GlcNAc) residue on the Asn residue of the peptide, wherein, optionally, one fucose (Fuc) residue is bound to said GlcNAc;
- a preliminary liquid chromatography/mass spectrometry step of subjecting a sugar chain-cleaved peptide sample obtained in the sugar chain cleavage step to liquid chromatography/mass spectrometry to obtain chromatogram, mass spectrum and product ion spectrum;
- a glycosylation site determination step of performing MS/MS ion search or de novo sequencing taking into account the GlcNAc or GlcNAc-Fuc modification on the Asn residue to determine the glycosylation site in the glycopeptide;
- a retention time and m/z estimation step of estimating the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing; and
- a main analysis step of subjecting the remainder of the glycopeptide-containing sample to liquid chromatography/mass spectrometry, selecting the precursor ion peak(s) to be analyzed based on the results of estimation of the retention time and m/z, and performing precursor ion-selected mass spectrometry for the selected peak(s) to determine the sugar chain structure of the glycopeptide.

2. The method according to claim 1, wherein the endo-β-N-acetylglucosaminidase(s) comprise(s) one or two or more selected from Endo F1, Endo F2, Endo F3, Endo M, Endo H and Endo S.

3. The method according to claim 1, wherein a sample in which glycopeptides are concentrated by removing peptides to which no sugar chains are bound is used as the glycopeptide sample.

4. The method according to claim 1, further comprising adding, as an internal standard, the sugar chain-cleaved peptide sample obtained in the sugar chain cleavage step to the remainder of the glycopeptide-containing sample, and performing the main analysis step to relatively quantify sugar chains present on the glycosylation site.

5. The method according to claim 4, wherein a sugar chain-cleaved peptide sample from which glycopeptides whose sugar chains are not cleaved off are removed is used as the internal standard.

6. The method according to claim 5, wherein removal of glycopeptides whose sugar chains are not cleaved off is carried out by a method of adding cold acetone to a sugar chain-cleaved peptide sample and precipitating the glycopeptides whose sugar chains are not cleaved off to separate them, or by adsorbing and removing the glycopeptides whose sugar chains are not cleaved off by hydrophilic interaction chromatography.

7. A system for analyzing N-linked sugar chain(s) of glycoprotein, comprising:
    a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one N-acetylglucosamine (GlcNAc) residue on the Asn residue of the peptide, wherein, optionally, one Fuc residue is bound to said GlcNAc by reaction with an endo-β-N-acetylglucosaminidase(s);
    a glycosylation site determination unit that performs MS/MS ion search or de novo sequencing taking into account the GlcNAc or GlcNAc-Fuc modification on the Asn residue to determine the glycosylation site in the glycopeptide;
    a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;
    a main analysis unit that performs main analysis on a main analysis sample, which is the glycopeptide-containing sample before the sugar chain cleavage; and
    an output unit that outputs analysis results,
    wherein said main analysis unit comprises:
        a unit for acquisition of liquid chromatography/mass spectrometry data of the main analysis sample that acquires chromatogram of the main analysis sample and mass spectrum of a fraction at the estimated retention time;
        a target peak selection unit that selects a precursor ion peak(s) to be analyzed from said mass spectrum of the fraction at the estimated retention time based on the m/z estimation result; and
        a sugar chain structure determination unit that acquires precursor ion-selected mass spectrometry data for the selected target peak(s) and determines the sugar chain structure of the glycopeptide.

8. A system for analyzing N-linked sugar chain(s) of glycoprotein, comprising:
    a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one N-acetylglucosamine (GlcNAc) residue on the Asn residue of the peptide by reaction with an endo-β-N-acetylglucosaminidase(s), wherein, optionally, one Fuc residue is bound to said GlcNAc;
    a glycosylation site determination unit that performs MS/MS ion search or de novo sequencing taking into account the GlcNAc or GlcNAc-Fuc modification on the Asn residue to determine the glycosylation site in the glycopeptide;
    a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;
    a main analysis unit that performs main analysis on a main analysis sample, which is the glycopeptide-containing sample before the sugar chain cleavage; and
    an output unit that outputs analysis results,
    wherein said main analysis unit comprises:
        a unit for acquisition of liquid chromatography/mass spectrometry data of the main analysis sample that acquires chromatogram of the main analysis sample to which the sugar chain-cleaved peptide sample is added as an internal standard, and mass spectrum of a fraction at the estimated retention time;
        a target peak selection unit that selects a precursor ion peak(s) to be analyzed from said mass spectrum of the fraction at the estimated retention time based on the m/z estimation result;
        a sugar chain structure determination unit that acquires precursor ion-selected mass spectrometry data for the selected target peak(s) and determines the sugar chain structure of the glycopeptide; and
        a sugar chain quantification unit that relatively quantifies sugar chains present on the glycosylation site by obtaining extracted ion chromatograms of the internal standard and each glycopeptide and calculating the relative intensity of each glycopeptide relative to the internal standard.

9. A program(s) for analyzing N-linked sugar chain(s) of glycoprotein, said program(s) causing one or more computers to function as:
    a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one N-acetylglucosamine (GlcNAc) residue on the Asn residue of the peptide by reaction with an endo-β-N-acetylglucosaminidase(s), wherein, optionally, one Fuc residue is bound to said GlcNAc;
    a glycosylation site determination unit that performs MS/MS ion search or de novo sequencing taking into account the GlcNAc or GlcNAc-Fuc modification on the Asn residue to determine the glycosylation site in the glycopeptide;
    a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;
    a main analysis unit that performs main analysis on a main analysis sample, which is the glycopeptide-containing sample not subjected to sugar chain cleavage treatment with an endo-β-N-acetylglucosaminidase(s); and
    an output unit that outputs analysis results,
    wherein said main analysis unit comprises:
        a unit for acquisition of liquid chromatography/mass spectrometry data of the main analysis sample that acquires chromatogram of the main analysis sample and mass spectrum of a fraction at the estimated retention time;
        a target peak selection unit that selects a precursor ion peak(s) to be analyzed from said mass spectrum of the fraction at the estimated retention time based on the m/z estimation result; and a sugar chain structure determination unit that acquires precursor ion-selected mass spectrometry data for the selected target peak(s) and determines the sugar chain structure of the glycopeptide.

10. A program(s) for analyzing N-linked sugar chain(s) of glycoprotein, said program(s) causing one or more computers to function as:

a preliminary liquid chromatography/mass spectrometry data acquisition unit that acquires chromatogram, mass spectrum and product ion spectrum of a sugar chain-cleaved peptide sample, said sample being prepared from a glycopeptide-containing sample which contains fragmented glycoprotein having N-linked sugar chain(s) by cleaving off the sugar chain(s) while leaving one N-acetylglucosamine (GlcNAc) residue on the Asn residue of the peptide by reaction with an endo-β-N-acetylglucosaminidase(s), wherein, optionally, one Fuc residue is bound to said GlcNAc;

a glycosylation site determination unit that performs MS/MS ion search or de novo sequencing taking into account the GlcNAc or GlcNAc-Fuc modification on the Asn residue to determine the glycosylation site in the glycopeptide;

a retention time and m/z estimation unit that estimates the retention time in liquid chromatography and the m/z of a precursor ion(s) of the glycopeptide before the sugar chain cleavage from the results obtained from the preliminary liquid chromatography/mass spectrometry and the MS/MS ion search or de novo sequencing;

a main analysis unit that performs main analysis on a main analysis sample, which is the glycopeptide-containing sample before the sugar chain cleavage; and an output unit that outputs analysis results, wherein said main analysis unit comprises:

a unit for acquisition of liquid chromatography/mass spectrometry data of the main analysis sample that acquires chromatogram of the main analysis sample to which the sugar chain-cleaved peptide sample is added as an internal standard, and mass spectrum of a fraction at the estimated retention time;

a target peak selection unit that selects a precursor ion peak(s) to be analyzed from said mass spectrum of the fraction at the estimated retention time based on the m/z estimation result;

a sugar chain structure determination unit that acquires precursor ion-selected mass spectrometry data for the selected target peak(s) and determines the sugar chain structure of the glycopeptide; and a sugar chain quantification unit that relatively quantifies sugar chains present on the glycosylation site by obtaining extracted ion chromatograms of the internal standard and each glycopeptide and calculating the relative intensity of each glycopeptide relative to the internal standard.

* * * * *